United States Patent
Kehler et al.

(10) Patent No.: US 10,689,379 B2
(45) Date of Patent: Jun. 23, 2020

(54) PYRAZOLO[3,4-B]PYRIDINES AND IMIDAZO[1,5-B]PYRIDAZINES AS PDE1 INHIBITORS

(71) Applicant: H. Lundbeck A/S, Valby (DK)

(72) Inventors: Jan Kehler, Valby (DK); Lars Kyhn Rasmussen, Valby (DK); Morten Langgård, Valby (DK); Mikkel Jessing, Valby (DK); Paulo Jorge Vieira Vital, Valby (DK); Karsten Juhl, Valby (DK); Mauro Marigo, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/424,585

(22) Filed: May 29, 2019

(65) Prior Publication Data

US 2019/0352302 A1 Nov. 21, 2019

Related U.S. Application Data

(63) Continuation of application No. 15/849,798, filed on Dec. 21, 2017, now Pat. No. 10,351,561.

(30) Foreign Application Priority Data

Dec. 22, 2016 (DK) .................................. 2016 00784
Jul. 6, 2017 (DK) .................................. 2017 00404

(51) Int. Cl.
| | |
|---|---|
| *A61K 31/4162* | (2006.01) |
| *A61K 31/4188* | (2006.01) |
| *A61K 31/437* | (2006.01) |
| *A61K 31/5025* | (2006.01) |
| *C07D 471/04* | (2006.01) |
| *C07D 487/04* | (2006.01) |
| *C07D 519/00* | (2006.01) |
| *A61K 31/4745* | (2006.01) |
| *A61K 31/502* | (2006.01) |
| *A61K 31/506* | (2006.01) |
| *A61P 25/28* | (2006.01) |
| *A61P 25/18* | (2006.01) |
| *A61P 25/00* | (2006.01) |
| *A61P 25/16* | (2006.01) |

(52) U.S. Cl.
CPC ........ *C07D 471/04* (2013.01); *A61K 31/4745* (2013.01); *A61K 31/502* (2013.01); *A61K 31/506* (2013.01); *A61P 25/00* (2018.01); *A61P 25/16* (2018.01); *A61P 25/18* (2018.01); *A61P 25/28* (2018.01); *C07D 487/04* (2013.01); *C07D 519/00* (2013.01)

(58) Field of Classification Search
CPC ............ A61K 31/4162; A61K 31/4188; A61K 31/437; A61K 31/5025; C07D 471/04; C07D 487/04
See application file for complete search history.

(56) References Cited

U.S. PATENT DOCUMENTS

| | | | |
|---|---|---|---|
| 10,034,861 | B2 | 7/2018 | Kehler et al. |
| 10,351,561 | B2 | 7/2019 | Kehler et al. |
| 2016/0083391 | A1 | 3/2016 | Burdi et al. |
| 2016/0083400 | A1 | 3/2016 | Burdi et al. |
| 2018/0000786 | A1 | 1/2018 | Kehler et al. |
| 2018/0179200 | A1 | 6/2018 | Kehler et al. |
| 2019/0105302 | A1 | 4/2019 | Kehler et al. |
| 2019/0185489 | A1 | 6/2019 | Juhl et al. |
| 2019/0194189 | A1 | 6/2019 | Juhl et al. |

FOREIGN PATENT DOCUMENTS

| | | |
|---|---|---|
| WO | WO 2006/044821 A1 | 4/2006 |
| WO | WO 2008/070095 A1 | 6/2008 |
| WO | WO 2008/111010 A1 | 9/2008 |
| WO | WO 2010/065153 A1 | 6/2010 |
| WO | WO 2013/142307 A1 | 9/2013 |
| WO | WO 2016/042775 A1 | 3/2016 |
| WO | WO 2016/055618 A1 | 4/2016 |
| WO | WO 2016/147659 A1 | 9/2016 |
| WO | WO 2016/170064 A1 | 10/2016 |

(Continued)

OTHER PUBLICATIONS

U.S. Appl. No. 15/637,920, filed Jun. 29, 2017, Granted, U.S. Pat. No. 10,034,861.
U.S. Appl. No. 16/033,395, filed Jul. 12, 2018, Published, 2019-0185489.
U.S. Appl. No. 15/849,798, filed Dec. 21, 2017, Granted, U.S. Pat. No. 10,351,561.
U.S. Appl. No. 16/217,754, filed Dec. 12, 2018, Published, 2019-0185489.
U.S. Appl. No. 16/218,019, filed Dec. 12, 2018, Published, 2019-0194189.
PCT/EP2017/066255, Aug. 27, 2017, International Search Report and Written Opinion.
PCT/EP2017/083721, Feb. 7, 2018, International Search Report and Written Opinion.

(Continued)

*Primary Examiner* — Brenda L Coleman
(74) *Attorney, Agent, or Firm* — Wolf, Greenfield & Sacks, P.C.

(57) ABSTRACT

The present invention provides compounds of formula (I) that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

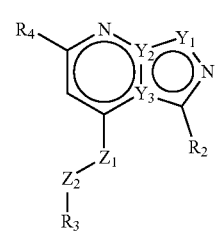

14 Claims, No Drawings

(56) References Cited

FOREIGN PATENT DOCUMENTS

| WO | WO 2017/172795 A1 | 10/2017 |
| WO | WO 2018/007249 A2 | 1/2018 |

OTHER PUBLICATIONS

PCT/EP2018/085798, Feb. 13, 2019, International Search Report and Written Opinion.
PCT/EP2018/085728, Feb. 11, 2019, International Search Report and Written Opinion.
International Search Report and Written Opinion dated Aug. 25, 2017 for Application No. PCT/EP2017/066255.
International Search Report and Written Opinion dated Feb. 7, 2018 for Application No. PCT/EP2017/083721.
International Search Report and Written Opinion dated Feb. 13, 2019 for Application No. PCT/EP2018/085798.
International Search Report and Written Opinion dated Feb. 11, 2019 for Application No. PCT/EP2018/085728.
Bernard et al., Transcriptional architecture of the primate neocortex. Neuron. Mar. 22, 2012;73(6):1083-99.
Blokland et al., PDE Inhibition and Cognition Enhancement. Expert Opinion Thera. Patents. 2012; 22(4):349-354.
Francis et al., Mammalian cyclic nucleotide phosphodiesterases: molecular mechanisms and physiological functions. Physiol Rev. Apr. 2011;91(2):651-90.
Medina, Therapeutic Utility of Phosphodiesterase Type I Inhibitors in Neurological Conditions. Front Neurosci. 2011; 5: 21.
Yamamoto et al., The effects of a novel phosphodiesterase 7A and -4 dual inhibitor, YM-393059, on T-cell-related cytokine production in vitro and in vivo. Eur J Pharmacol. Jul. 10, 2006;541(1-2):106-14.

PYRAZOLO[3,4-B]PYRIDINES AND IMIDAZO[1,5-B]PYRIDAZINES AS PDE1 INHIBITORS

CROSS-REFERENCE TO RELATED APPLICATIONS

This application is a continuation application of U.S. application Ser. No. 15/849,798, filed Dec. 21, 2017 (allowed), which claims priority to Danish Application No. PA201600784, filed Dec. 22, 2016, and Danish Application No. PA201700404, filed Jul. 6, 2017, the entire contents of which are hereby incorporated herein by reference.

FIELD OF THE INVENTION

The present invention provides compounds that are PDE1 enzyme inhibitors and their use as medicaments, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of cN-concentrations in all cells, and their varied regulatory mechanisms provide for integration and crosstalk with myriads of signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, PDE1 represents an interesting regulatory link between cyclic nucleotides and intracellular $Ca^{2+}$.

The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain contains two $Ca^{2+}$/CaM binding domains and two phosphorylation sites and different splice variants have different variations of the N-terminal domain, which can give proteins with different amino acid sequence with different biochemical functions. PDE1 is a dual substrate PDE and the PDE1C-subtype has equal activity towards cAMP and cGMP (Km≈1-3 µM), whereas the subtypes PDE1A and PDE1B have a preference for cGMP (Km for cGMP≈1-3 µM and for cAMP≈10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messenger's cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5 (February), 21) has suggested the potential for the therapeutic use of PDE1 inhibitors in neurological diseases, like e.g. Alzheimer's, Parkinson's and Huntington's Diseases and in psychiatric disorders like e.g. Attention Deficit Hyperactivity Disorder (ADHD), depression, anxiety, narcolepsy, cognitive impairment and cognitive impairment associated with schizophrenia (CIAS) and in restless leg syndrome. There have also been patent applications claiming that PDE1 inhibitors are useful in diseases that may be alleviated by the enhancement of progesterone-signalling such as female sexual dysfunction (e.g. WO 2008/070095).

Various chemical structures with PDE1 inhibiting activity have been identified. For example, WO 2016/055618 discloses triazolopyrazinones as PDE1 inhibitors; WO 2016/042775, US 2016/0083391 and US 2016/0083400 disclose tricyclic lactams as PDE1 inhibitors; WO 2016/147659 and WO 2016/170064 discloses imidazotriazinones as PDE1 inhibitors; and WO 2016/174188 discloses imidazopyrazinones as PDE1 inhibitors.

Current treatments for neurodegenerative and/or psychiatric disorders are not efficacious in all patients. Hence, there remains a need for alternative methods of treatment of such diseases and for this purpose PDE1 inhibitors may be a good alternative. The present invention discloses new pyrazolo[3, 4-b]pyridines and imidazo[1,5-b]pyridazines with PDE1 inhibitor activity and good physicochemical properties as PDE1 inhibitors.

SUMMARY OF THE INVENTION

PDE1 enzymes are expressed in the Central Nervous System (CNS), making this gene family an attractive source of new targets for the treatment of psychiatric and neurodegenerative disorders.

Accordingly, the present invention relates to compounds of formula (I)

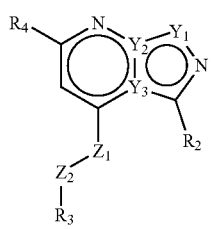

wherein
Z1 is selected from NH, $CH_2$, O and S;
Z2 is selected from NH, $CH_2$, O and S;
with the proviso that at least one of Z1 and Z2 is $CH_2$;
R1 is selected from the group consisting of hydrogen, linear or branched $C_{1-4}$ alkyl and saturated monocyclic $C_{3-4}$ cycloalkyl, wherein said linear or branched $C_{1-4}$ alkyl and saturated monocyclic $C_{3-4}$ cycloalkyl can be optionally substituted with one or more halogen;
R2 is selected from the group consisting of linear or branched $C_{1-6}$ alkyl, saturated monocyclic $C_{3-6}$ cycloalkyl, oxetanyl, tetrahydrofuranyl and tetrahydropyranyl, all of which can optionally be substituted with one or more halogen;
R3 is a 5- or 6-membered heteroaryl, which can optionally be substituted with one or more substituents selected from linear or branched $C_{1-4}$ alkyl, linear or branched $C_{1-4}$ alkoxy and halogen, wherein said linear or branched $C_{1-4}$ alkyl and linear or branched $C_{1-4}$ alkoxy can be optionally substituted with one or more halogen, or
R3 is a 9-membered bicyclic heteroaryl, which can optionally be substituted with one or more substituents selected from linear or branched $C_{1-4}$ alkyl, linear or branched $C_{1-4}$ alkoxy and halogen, wherein said linear or branched $C_{1-4}$ alkyl and linear or branched $C_{1-4}$ alkoxy can be optionally substituted with one or more halogen;
R4 is a 5- or 6-membered heteroaryl, which can optionally be substituted with one or more substituents selected from linear or branched $C_{1-4}$ alkyl, linear or branched $C_{1-4}$ alkoxy and halogen, wherein said linear or branched $C_{1-4}$ alkyl and linear or branched $C_{1-4}$ alkoxy can be optionally substituted with one or more halogen, or
R4 is a phenyl, which can optionally be substituted with one or more substituents selected from linear or branched $C_{1-4}$ alkyl, linear or branched $C_{1-4}$ alkoxy and halogen, wherein said linear or branched $C_{1-4}$ alkyl and linear or branched $C_{1-4}$ alkoxy can be optionally substituted with one or more halogen, or
R4 is a pyridinone, which can optionally be substituted with one or more substituents selected from linear or branched $C_{1-4}$ alkyl, linear or branched $C_{1-4}$ alkoxy and halogen, wherein said linear or branched $C_{1-4}$ alkyl and linear or branched $C_{1-4}$ alkoxy can be optionally substituted with one or more halogen; or
R4 is a 9-membered bicyclic heteroaryl, which can optionally be substituted with one or more substituents selected from linear or branched $C_{1-4}$ alkyl, linear or branched $C_{1-4}$ alkoxy and halogen, wherein said linear or branched $C_{1-4}$ alkyl and linear or branched $C_{1-4}$ alkoxy can be optionally substituted with one or more halogen;
or a pharmaceutically acceptable salt thereof.

Reference to compounds encompassed by the present invention includes the free base and pharmaceutically acceptable salts of the compounds, such as acid addition salts of the compounds, racemic mixtures of the compounds, or the corresponding enantiomer and/or optical isomer of the compounds for which this is relevant, and polymorphic and amorphic forms of compounds of the present invention and of pharmaceutically acceptable salts of said compounds, as well as tautomeric forms the compounds for which this is relevant. Furthermore, the compounds of the present invention and pharmaceutically acceptable salts thereof may potentially exist in unsolvated as well as in solvated forms with pharmaceutically acceptable solvents such as water, ethanol and the like. Both solvated and unsolvated forms of the compounds and pharmaceutically acceptable salts thereof are encompassed by the present invention.

In one embodiment, the invention relates to a compound according to formula (I) or a pharmaceutically acceptable salt thereof for use in therapy.

In one embodiment, the invention relates to a compound according to formula (I) or a pharmaceutically acceptable salt thereof, for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

In one embodiment, the invention relates to a pharmaceutical composition comprising a compound according formula (I) or a pharmaceutically acceptable salt thereof, and one or more pharmaceutically acceptable carrier and/or excipient.

In one embodiment, the invention relates to a method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to formula (I) or a pharmaceutically acceptable salt thereof, to a patient in need thereof.

In one embodiment, the invention relates to the use of a compound according to formula (I) or a pharmaceutically acceptable salt thereof, in the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

Definitions

Pde1 Enzymes:

The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.

Pde1 Inhibitors:

In the context of the present invention, a compound is considered to be a PDE1 inhibitor if the amount required to reach the IC50 level of any of the three PDE1 isoforms is 10 micro molar or less, such as less than 9 micro molar, such as 8 micro molar or less, such as 7 micro molar or less, such as 6 micro molar or less, such as 5 micro molar or less, such as 4 micro molar or less, such as 3 micro molar or less. For preferred compounds of the invention, the required amount of PDE1 inhibitor required to reach the IC50 level is 2 micro molar or less, such as 1 micro molar or less, in particular 500 nM or less.

Preferred compounds of the invention exhibit selectivity towards the PDE1B isoform meaning that said compounds are stronger as PDE1B inhibitors than as PDE1A and/or PDE1C inhibitors. In preferred embodiments, said compounds are at least two-fold stronger, three-fold stronger, four-fold stronger, five-fold stronger or ten-fold stronger as PDE1B inhibitors than as PDE1A and/or PDE1C inhibitors. In more preferred embodiments, said compounds are at least fifteen-fold stronger or twenty-fold stronger as PDE1B inhibitors than as PDE1A and/or PDE1C inhibitors. In preferred embodiments, the required amount of PDE1 inhibitor required to reach the IC50 level of PDE1B is 400 nM or less, such as 300 nM or less, 200 nM or less, 100 nM or less, or 50 nM or less, for example 25 nM or less. Selectivity towards the PDE1B isoform may prevent potentially unwanted effects associated with PDE1A and/or PDE1C inhibition.

Substituents:

In the present context, "optionally substituted" means that the indicated moiety may or may not be substituted, and when substituted it is mono-, di-, or tri-substituted. It is understood that where no substituents are indicated for an "optionally substituted" moiety, then the position is held by a hydrogen atom.

As used in the context of the present invention, the terms "halo" and "halogen" are used interchangeably and refer to fluorine, chlorine, bromine or iodine. In a preferable embodiment, "halogen" refers to fluorine.

A given range may interchangeably be indicated with "-" (dash) or "to", e.g. the term "$C_{1-4}$ alkyl" is equivalent to "$C_1$ to $C_4$ alkyl".

The terms "$C_{1-3}$ alkyl", "$C_{1-4}$ alkyl", "$C_{1-5}$ alkyl" and "$C_{1-6}$ alkyl" refer to a linear (i.e. unbranched) or branched saturated hydrocarbon having 1, 2, 3, 4, 5, or 6 carbon atoms. Examples of such groups include, but are not limited to, methyl, ethyl, 1-propyl, 2-propyl, 1-butyl, 2-butyl, 2-methyl-2-propyl, 2-methyl-1-butyl, n-hexyl.

The term "$C_{1-4}$ alkoxy" refers to a moiety of the formula —OR', wherein R' indicates $C_{1-4}$ alkyl as defined above.

The term saturated monocyclic $C_{3-6}$ cycloalkyl refers to cyclopropyl, cyclobutyl, cyclopentyl and cyclohexyl. $C_{3-4}$ cycloalkyl refers to cyclopropyl and cyclobutyl.

The term "5-membered heteroaryl" refers to a 5-membered aromatic monocyclic ring containing 1 to 4 carbon atoms and one or more heteroatoms selected from oxygen, nitrogen and sulfur. Examples include, but are not limited to pyrazolyl, imidazolyl, oxazolyl, oxadiazolyl, triazolyl, tetrazolyl, thiazolyl, thiophenyl, isoxazolyl and thiadiazolyl.

The term "6-membered heteroaryl" refers to a 6-membered aromatic monocyclic ring containing 1 to 5 carbon atoms and one or more nitrogen atoms. Particular mention is made of pyridyl, pyrimidinyl, pyrazinyl and pyridazinyl.

The term "9-membered bicyclic heteroaryl" refers to a moiety consisting of a 6-membered aromatic ring and a 5-membered aromatic ring fused together to give a 9-membered bicyclic aromatic moeity. The 9-membered bicyclic heteroaryl consists of carbon and one or more heteroatoms selected from oxygen, nitrogen and sulfur. Particular mention is made of benzoxazol, imidazo[1,5-a]pyridine and imidazo[1,2-a]pyridine.

Isomeric and Tautomeric Forms

Where compounds of the present invention contain one or more chiral centres reference to any of the compounds will, unless otherwise specified, cover the enantiomerically or diastereomerically pure compound as well as mixtures of the enantiomers or diastereomers in any ratio.

When a compound with a chiral centre is denoted with the prefix (−) or (+) it is understood that said compound could be either the S-enantiomer or the R-enantiomer. I.e. a compound with the prefix (−) could be either the S-enantiomer or the R-enantiomer and a compound with the prefix (+) could be either the S-enantiomer or the R-enantiomer. When both enantiomer the (−) and the (+) compound have been exemplified for a compound it follows that one is the S-enantiomer and the other is the R-enantiomer. It follows that if for example compound Example 47 can be determined to be the R-enantiomer, then compound Example 48 will be the S-enantiomer and vice versa.

The absolute stereochemistry for a compound of the invention can be determined by X-ray crystallography or vibrational circular dichroism.

Furthermore, some of the compounds of the present invention may exist in different tautomeric forms and it is intended that any tautomeric forms that the compounds are able to form are included within the scope of the present invention.

Pharmaceutically Acceptable Salts:

The compounds of this invention are generally utilized as the free substance or as a pharmaceutically acceptable salt thereof. When a compound of formula (I) contains a free base, such salts are prepared in a conventional manner by treating a solution or suspension of a free base of formula (I) with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid.

Additional examples of useful acids to form pharmaceutically acceptable salts can be found e.g. in Stahl and Wermuth (Eds) "Handbook of Pharmaceutical salts. Properties, selection, and use", Wiley-VCH, 2008.

Therapeutically Effective Amount:

In the present context, the term "therapeutically effective amount" of a compound means an amount sufficient to cure, alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Combinations

In one embodiment of the invention, the compound of formula (I) is for use as stand-alone treatment as the sole active compound.

In another embodiment of the invention, the compound of formula (I) may be used in combination with a second compound, wherein said second compound is selected from the following: a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

In yet another embodiment of the invention, the compound of formula (I) may be used in combination with a second compound, wherein said second compound is a compound that is useful in the treatment of a psychiatric disorder.

The terms "combined use", "in combination with" and "a combination of" and the like as used herein in the context of the method of the invention comprising the combined administration of therapeutically effective amounts of a compound of formula (I), and another pharmaceutically active compound, is intended to mean the administration of a compound of formula (I) simultaneously or sequentially, in any order, together with said second compound.

The two compounds may be administered simultaneously or with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more of said second compound when treatment with a compound of formula (I) is initiated. In other instances, the patient may already be in treatment with a compound of formula (I) when treatment with one or more of said second compound is initiated. In other instances, the treatment with a compound of formula (I) and treatment with one or more of said second compound is initiated at the same time.

Compounds for Combination Treatment

In the context of the invention, compounds to be used in combination with a compound of formula (I) in the treatment of a neurodegenerative disorder, are selected from for example a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

In the context of the invention, compounds to be used in combination with a compound of formula (I) in the treatment of a psychiatric and/or cognitive disorder, is a compound with a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor. Examples of such compounds includes clozapine, risperidone, paliperidone, olanzapine, quetiapine, amisulpride, ziprasidone, aripiprazole, brexpiprazole, asenapine, haloperidol, iloperidone, lurasidone, chlorpromazine, blonanserin, perphenazine, levomepromazine, sulpiride, fluphenazine, zuclopenthixol, flupenthixol and cariprazine.

Administration Routes

Pharmaceutical compositions comprising a compound of the present invention either as the sole active compound or in combination a second compound defined above, may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (I), such as one of the compound examples disclosed in the Experimental Section herein. The present invention also provides a process for making a pharmaceutical composition comprising a compound of formula (I). The pharmaceutical compositions according to the invention may be formulated with pharmaceutically acceptable excipients in accordance with conventional techniques such as those disclosed in Remington, "The Science and Practice of Pharmacy", 22$^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

DETAILED DESCRIPTION OF THE INVENTION

The present inventors have identified compounds that are PDE1 inhibitors, and as such are useful to treat neurodegenerative and psychiatric disorders. The present invention thus provides compounds of formula (I) that are effective in inhibiting PDE1 for use as a medicament in the treatment of a mammal, preferably a human.

The invention provides a compound of formula (I) or a pharmaceutically acceptable salt thereof, as well as a pharmaceutical composition containing such a compound, for use in the treatment of a brain disease which could be a neurodegenerative disorder or a psychiatric disorder. In a preferred embodiment, the neurodegenerative disorder is selected from the group consisting of Alzheimer's Disease, Parkinson's Disease and Huntington's Disease. In another preferred embodiment, the psychiatric disorder is selected from the group consisting of Attention Deficit Hyperactivity Disorder (ADHD), depression, anxiety, narcolepsy, cognitive impairment and cognitive impairment associated with schizophrenia (CIAS). Other brain disorders could be e.g. restless leg syndrome.

This invention further provides a method of treating a brain disease which could be a neurodegenerative or a psychiatric disorder, which method comprises administering to said mammal a pharmaceutically effective amount of a compound of formula (I) or a pharmaceutically acceptable salt thereof. Examples of neurodegenerative disorders that can be treated according to the present invention include Alzheimer's Disease, Parkinson's Disease and Huntington's Disease, which method comprises administering to the subject a therapeutically effective amount of a compound of formula (I). Examples of psychiatric disorders that can be treated according to the present invention include Attention Deficit Hyperactivity Disorder (ADHD), depression, narcolepsy, cognitive impairment and cognitive impairment associated with schizophrenia (CIAS). Other brain disorders to be treated could be e.g. restless leg syndrome.

EMBODIMENTS OF THE INVENTION

In the following, embodiments of the invention are disclosed. The first embodiment is denoted E1, the second embodiment is denoted E2 and so forth E1. A compound of formula (I)

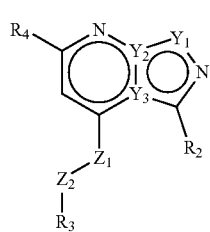

wherein
Y1=N—R1, Y2=C and Y3=C, or
Y1=C—R1, Y2=N and Y3=C;
Z1 is selected from NH, CH$_2$, O and S;
Z2 is selected from NH, CH$_2$, O and S;
with the proviso that at least one of Z1 and Z2 is CH$_2$;
R1 is selected from the group consisting of hydrogen, linear or branched C$_{1-4}$ alkyl and saturated monocyclic C$_{3-4}$ cycloalkyl, wherein said linear or branched C$_{1-4}$ alkyl and saturated monocyclic C$_{3-4}$ cycloalkyl can be optionally substituted with one or more halogen;
R2 is selected from the group consisting of linear or branched C$_{1-6}$ alkyl, saturated monocyclic C$_{3-6}$ cycloalkyl, oxetanyl, tetrahydrofuranyl and tetrahydropyranyl, all of which can optionally be substituted with one or more halogen;
R3 is a 5- or 6-membered heteroaryl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen, or
R3 is a 9-membered bicyclic heteroaryl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen;
R4 is a 5- or 6-membered heteroaryl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen, or
R4 is a phenyl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen, or
R4 is a pyridinone, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen; or
R4 is a 9-membered bicyclic heteroaryl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen;
or a pharmaceutically acceptable salt thereof.

E2. The compound according to embodiment 1 of formula (I)

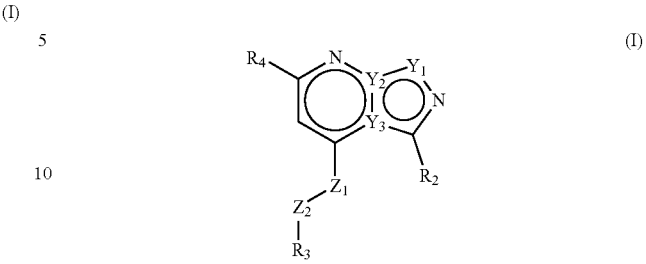

wherein
Y1=N—R1, Y2=C and Y3=C, or
Y1=C—R1, Y2=N and Y3=C;
Z1 is selected from NH, CH$_2$, O and S;
Z2 is selected from NH, CH$_2$, O and S;
with the proviso that at least one of Z1 and Z2 is CH$_2$;
R1 is selected from the group consisting of hydrogen, linear or branched C$_1$-C$_4$ alkyl and saturated monocyclic C$_3$-C$_4$ cycloalkyl, wherein said linear or branched C$_1$-C$_4$ alkyl and saturated monocyclic C$_3$-C$_4$ cycloalkyl can be optionally substituted with one or more halogen;
R2 is selected from the group consisting of linear or branched C$_1$-C$_6$ alkyl, saturated monocyclic C$_3$-C$_6$ cycloalkyl, oxetanyl, tetrahydrofuranyl and tetrahydropyranyl, all of which can optionally be substituted with one or more halogen;
R3 is a 5- or 6-membered heteroaryl, which can optionally be substituted with one or more substituents selected from linear or branched C$_1$-C$_4$ alkyl, linear or branched C$_1$-C$_4$ alkoxy and halogen, wherein said linear or branched C$_1$-C$_4$ alkyl and linear or branched C$_1$-C$_4$ alkoxy can be optionally substituted with one or more halogen;
R4 is a 5- or 6-membered heteroaryl, which can optionally be substituted with one or more substituents selected from linear or branched C$_1$-C$_4$ alkyl, linear or branched C$_1$-C$_4$ alkoxy and halogen, wherein said linear or branched C$_1$-C$_4$ alkyl and linear or branched C$_1$-C$_4$ alkoxy can be optionally substituted with one or more halogen, or
R4 is a phenyl, which can optionally be substituted with one or more substituents selected from linear or branched C$_1$-C$_4$ alkyl, linear or branched C$_1$-C$_4$ alkoxy and halogen, wherein said linear or branched C$_1$-C$_4$ alkyl and linear or branched C$_1$-C$_4$ alkoxy can be optionally substituted with one or more halogen, or
R4 is a pyridinone, which can optionally be substituted with one or more substituents selected from linear or branched C$_1$-C$_4$ alkyl, linear or branched C$_1$-C$_4$ alkoxy and halogen, wherein said linear or branched C$_1$-C$_4$ alkyl and linear or branched C$_1$-C$_4$ alkoxy can be optionally substituted with one or more halogen;
or a pharmaceutically acceptable salt thereof.

E3. The compound according to embodiment 1 of formula (I)

13

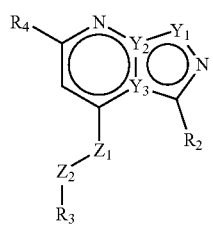

wherein
Y1=N—R1, Y2=C and Y3=C, or
Y1=C—R1, Y2=N and Y3=C;
Z1 is selected from NH and CH$_2$;
Z2 is selected from NH and CH$_2$;
with the proviso that at least one of Z1 and Z2 is CH$_2$;
R1 is selected from the group consisting of hydrogen, linear or branched C$_{1-4}$ alkyl and saturated monocyclic C$_{3-4}$ cycloalkyl, wherein said linear or branched C$_{1-4}$ alkyl and saturated monocyclic C$_{3-4}$ cycloalkyl can be optionally substituted with one or more halogen;
R2 is selected from the group consisting of linear or branched C$_{1-6}$ alkyl, saturated monocyclic C$_{3-6}$ cycloalkyl, oxetanyl, tetrahydrofuranyl and tetrahydropyranyl, all of which can optionally be substituted with one or more halogen;
R3 is a 5- or 6-membered heteroaryl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen;
R4 is a 5- or 6-membered heteroaryl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen, or
R4 is a phenyl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen, or
R4 is a pyridinone, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$ alkoxy can be optionally substituted with one or more halogen;
or a pharmaceutically acceptable salt thereof.
E4. The compound according to embodiment 1 of formula (I)

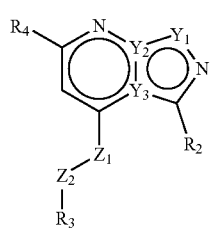

14 wherein
Y1=N—R1, Y2=C and Y3=C, or
Y1=C—R1, Y2=N and Y3=C;
Z1 is selected from NH and CH$_2$;
Z2 is selected from NH and CH$_2$;
with the proviso that at least one of Z1 and Z2 is CH$_2$;
R1 is hydrogen or a linear or branched C$_{1-4}$ alkyl, wherein said linear or branched C$_{1-4}$ alkyl can be optionally mono-di- or tri-substituted with fluorine;
R2 a linear or branched C$_{1-4}$ alkyl, wherein said linear or branched C$_{1-4}$ alkyl can be optionally mono-di- or tri-substituted with fluorine;
R3 is a 5- or 6-membered heteroaryl, which can optionally be substituted with one or more substituents selected from linear or branched C$_{1-4}$ alkyl and linear or branched C$_{1-4}$ alkoxy; wherein said linear or branched C$_{1-4}$ alkyl and linear or branched C$_{1-4}$ alkoxy can be optionally mono-di- or tri-substituted with fluorine;
R4 is a 5- or 6-membered heteroaryl, which can optionally be substituted with one or more substituents selected from linear or branched C$_{1-4}$ alkyl and linear or branched C$_{1-4}$ alkoxy wherein said linear or branched C$_{1-4}$ alkyl and linear or branched C$_{1-4}$ alkoxy can be optionally mono-di- or tri-substituted with fluorine, or
R4 is a phenyl, which can optionally be substituted with one or more substituents selected from linear or branched C$_{1-4}$ alkyl and linear or branched C$_{1-4}$ alkoxy wherein said linear or branched C$_{1-4}$ alkyl and linear or branched C$_{1-4}$ alkoxy can be optionally mono-di- or tri-substituted with fluorine, or
R4 is a pyridinone, which can optionally be substituted with one or more substituents selected from linear or branched C$_{1-4}$ alkyl and linear or branched C$_{1-4}$ alkoxy wherein said linear or branched C$_{1-4}$ alkyl and linear or branched C$_{1-4}$ alkoxy can be optionally mono-di- or tri-substituted with fluorine;
or a pharmaceutically acceptable salt thereof.
E5. The compound according to embodiment 1 of formula (I)

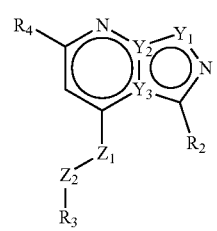

wherein
Y1=N—R1, Y2=C and Y3=C, or
Y1=C—R1, Y2=N and Y3=C;
Z1 is selected from NH and CH$_2$;
Z2 is selected from NH and CH$_2$;
with the proviso that at least one of Z1 and Z2 is CH$_2$;
R1 is hydrogen or a linear or branched C$_{1-4}$ alkyl;
R2 is a linear or branched C$_{1-6}$ alkyl;
R3 is a 5- or 6-membered heteroaryl, which can optionally be substituted with one or more substituents selected from linear or branched C$_{1-4}$ alkyl and linear or branched C$_{1-4}$ alkoxy;
R4 is a 5- or 6-membered heteroaryl, which can optionally be substituted with one or more substituents selected from linear or branched $C_{1-4}$ alkyl and linear or branched $C_{1-4}$ alkoxy; or a pharmaceutically acceptable salt thereof.

E6. The compound according to any of embodiments 1, 2, 3 or 4 of formula (Ia)

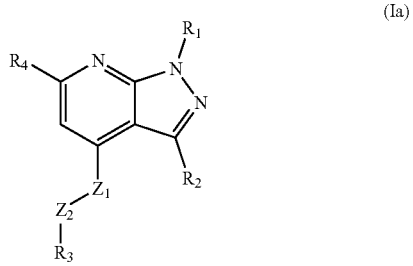

(Ia)

wherein Z1, Z2, R1, R2, R3 and R4 are as defined in embodiment 1, or
wherein Z1, Z2, R1, R2, R3 and R4 are as defined in embodiment 2, or
wherein Z1, Z2, R1, R2, R3 and R4 are as defined in embodiment 3, or
wherein Z1, Z2, R1, R2, R3 and R4 are as defined in embodiment 4; or wherein Z1, Z2, R1, R2, R3 and R4 are as defined in embodiment 5;
or a pharmaceutically acceptable salt thereof.

E7. The compound according to any of embodiments 1, 2, 3 or 4 of formula (Ib)

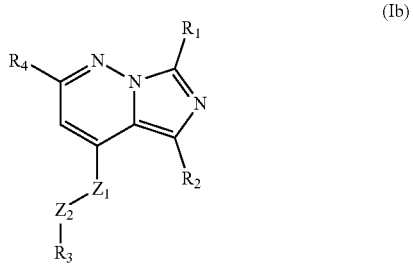

(Ib)

wherein Z1, Z2, R1, R2, R3 and R4 are as defined in embodiment 1, or
wherein Z1, Z2, R1, R2, R3 and R4 are as defined in embodiment 2, or
wherein Z1, Z2, R1, R2, R3 and R4 are as defined in embodiment 3, or
wherein Z1, Z2, R1, R2, R3 and R4 are as defined in embodiment 4; or
wherein Z1, Z2, R1, R2, R3 and R4 are as defined in embodiment 5;
or a pharmaceutically acceptable salt thereof.

E8. The compound according to any of embodiments 1-7, wherein the term "halogen" indicates fluorine.

E9. The compound according to any of embodiments 1-8, wherein Z1 is NH.

E10. The compound according to any of embodiments 1-9, wherein Z2 is $CH_2$.

E11. The compound according to any of embodiments 1-10, wherein Z1 is NH and Z2 is $CH_2$.

E12. The compound according to any of embodiments 1-11, wherein R1 is linear or branched $C_{1-4}$ alkyl.

E13. The compound according to embodiment 12, wherein R1 is methyl.

E14. The compound according to any of embodiments 1-13, wherein R2 is linear or branched $C_{1-6}$ alkyl.

E15. The compound according to embodiment 14, wherein R2 is selected from isopropyl and 1-methyl-propyl.

E16. The compound according to any of embodiments 1-15, wherein R3 is a 5-membered heteroaryl selected from pyrazolyl, imidazolyl, oxazolyl, oxadiazolyl, triazolyl, tetrazolyl, thiazolyl and thiophenyl, all of which can optionally be substituted with a methyl.

E17. The compound according to embodiment 16, wherein R3 is a 5-membered heteroaryl selected from pyrazolyl, imidazolyl, oxazolyl, oxadiazolyl, triazolyl, tetrazolyl, thiazolyl and thiophenyl, wherein said 5-membered heteroaryl is substituted with a methyl.

E18. The compound according to any of embodiments 1-15, wherein R3 is a 6-membered heteroaryl, which can optionally be substituted with a substituent selected from methyl, trifluoromethyl and linear or branched $C_{1-4}$ alkoxy.

E19. The compound according to embodiment 18, wherein said 6-membered heteroaryl is selected from pyridyl, pyrimidinyl, pyrazinyl and pyridazinyl.

E20. The compound according to any of embodiments 1-15, wherein R3 is pyridyl, which is substituted with a linear or branched $C_{1-4}$ alkoxy.

E21. The compound according to any of embodiments 1-15, wherein R3 is a 9-membered bicyclic heteroaryl, which is optionally substituted with one or more methyl.

E22. The compound according to embodiment 21, wherein said 9-membered bicyclic heteroaryl is selected from benzoxazol, imidazo[1,5-a]pyridine and imidazo[1,2-a]pyridine.

E23. The compound according to any of embodiments 1-21, wherein R4 is a 5-membered heteroaryl selected from pyrazolyl, imidazolyl, oxazolyl, oxadiazolyl, triazolyl, tetrazolyl, thiazolyl and thiophenyl, all of which can optionally be substituted with a methyl.

E24. The compound according to embodiment 23, wherein R4 is a 5-membered heteroaryl selected from pyrazolyl, imidazolyl, oxazolyl, oxadiazolyl, triazolyl, tetrazolyl, thiazolyl and thiophenyl, wherein said 5-membered heteroaryl is substituted with a methyl.

E25. The compound according to any of embodiments 1-22, wherein R4 is a 6-membered heteroaryl, which can optionally be substituted with a linear or branched $C_{1-4}$ alkoxy.

E26. The compound according to embodiment 25, wherein said 6-membered heteroaryl is selected from pyridyl, pyrimidinyl, pyrazinyl and pyridazinyl.

E27. The compound according to any of embodiments 1-23, wherein R4 is a pyridyl, which is substituted with a linear or branched $C_{1-4}$ alkoxy.

E28. The compound according to any of embodiments 1-23, wherein R4 is 2-ethoxy-3-pyridyl.

E29. The compound according to any of embodiments 1-23, wherein R4 is a phenyl, which can optionally be substituted with one or more methyl.

E30. The compound according to any of embodiments 1-23, wherein R4 is a pyridinone, which can optionally be substituted with one or more methyl.

E31. The compound according to any of embodiments 1-23, wherein R4 is a 9-membered bicyclic heteroaryl, which can optionally be substituted with one or more methyl.

E32. The compound according to embodiment 31, wherein said 9-membered bicyclic heteroaryl is selected from benzoxazol, imidazo[1,5-a]pyridine and imidazo[1,2-a]pyridine.

E33. The compound according to any of embodiments 1-15, wherein R3 is a 5-membered heteroaryl selected from pyrazolyl, imidazolyl, oxazolyl, oxadiazolyl, triazolyl, tetrazolyl, thiazolyl and thiophenyl, all of which can optionally be substituted with a methyl; or R3 is a 6-membered heteroaryl, which can optionally be substituted with a substituent selected from methyl, trifluoromethyl or a linear or branched $C_{1-4}$ alkoxy; wherein said 6-membered heteroaryl is selected from pyrazolyl, imidazolyl, oxazolyl, oxadiazolyl, triazolyl, tetrazolyl, thiazolyl and thiophenyl; or R3 is a 9-membered bicyclic heteroaryl, which is optionally substituted with one or more methyl.

E34. The compound according to any of embodiments 1-15, wherein R4 is a 5-membered heteroaryl selected from pyrazolyl, imidazolyl, oxazolyl, oxadiazolyl, triazolyl, tetrazolyl, thiazolyl and thiophenyl wherein said 5-membered heteroaryl can be optionally substituted with a methyl; or R4 is a 6-membered heteroaryl, which can optionally be substituted with a linear or branched $C_{1-4}$ alkoxy; wherein said 6-membered heteroaryl is selected from pyridyl, pyrimidinyl, pyrazinyl and pyridazinyl; or R4 is a phenyl, which can optionally be substituted with one or more methyl; or R4 is a pyridinone, which can optionally be substituted with one or more methyl; or R4 is a 9-membered bicyclic heteroaryl, which can optionally be substituted with one or more methyl.

E35. The compound according to embodiment 1, wherein the compound is selected from the group consisting of:

1. 6-(2-ethoxy-3-pyridyl)-3-isopropyl-1-methyl-N-[(1-methylimidazol-4-yl)methyl]pyrazolo[3,4-b]pyridin-4-amine;
2. 6-(2-ethoxy-3-pyridyl)-3-isopropyl-1-methyl-N-[(2-methyloxazol-4-yl)methyl]pyrazolo[3,4-b]pyridin-4-amine;
3. 6-(2-ethoxy-3-pyridyl)-3-isopropyl-1-methyl-N-(1H-pyrazol-3-ylmethyl)pyrazolo[3,4-b]pyridin-4-amine;
4. 6-(2-ethoxy-3-pyridyl)-3-isopropyl-1-methyl-N-[(1-methyl-1,2,4-triazol-3-yl)methyl]pyrazolo[3,4-b]pyridin-4-amine;
5. 6-(2-ethoxy-3-pyridyl)-3-isopropyl-1-methyl-N-[(5-methyl-1,2,4-oxadiazol-3-yl)methyl]pyrazolo[3,4-b]pyridin-4-amine;
6. 6-(2-ethoxy-3-pyridyl)-3-isopropyl-1-methyl-N-[(5-methyl-1H-pyrazol-3-yl)methyl]pyrazolo[3,4-b]pyridin-4-amine;
7. 6-(2-ethoxy-3-pyridyl)-3-isopropyl-N-[(2-methoxy-4-pyridyl)methyl]-1-methyl-pyrazolo[3,4-b]pyridin-4-amine;
8. 2-(2-ethoxy-3-pyridyl)-5-isopropyl-7-methyl-N-[(1-methyl imidazol-4-yl)methyl]imidazo[1,5-b]pyridazin-4-amine;
9. 2-(2-ethoxy-3-pyridyl)-5-isopropyl-7-methyl-N-[(2-methyloxazol-4-yl)methyl]imidazo[1,5-b]pyridazin-4-amine;
10. 2-(2-ethoxy-3-pyridyl)-5-isopropyl-7-methyl-N-(1H-pyrazol-3-ylmethyl)imidazo[1,5-b]pyridazin-4-amine;
11. 2-(2-ethoxy-3-pyridyl)-5-isopropyl-7-methyl-N-[(1-methyl-1,2,4-triazol-3-yl)methyl]imidazo[1,5-b]pyridazin-4-amine;
12. 2-(2-ethoxy-3-pyridyl)-5-isopropyl-7-methyl-N-[(5-methyl-1,2,4-oxadiazol-3-yl)methyl]imidazo[1,5-b]pyridazin-4-amine;
13. 2-(2-ethoxy-3-pyridyl)-5-isopropyl-7-methyl-N-[(5-methyl-1H-pyrazol-3-yl)methyl]imidazo[1,5-b]pyridazin-4-amine;
14. 2-(2-ethoxy-3-pyridyl)-5-isopropyl-N-[(5-methoxy-3-pyridyl)methyl]-7-methyl-imidazo[1,5-b]pyridazin-4-amine;
15. 2-(2-ethoxy-3-pyridyl)-5-isopropyl-N-[(2-methoxy-4-pyridyl)methyl]-7-methyl-imidazo[1,5-b]pyridazin-4-amine;
16. 2-(2-ethoxy-3-pyridyl)-5-isopropyl-7-methyl-N-[(2-methyl oxazol-5-yl)methyl]imidazo[1,5-b]pyridazin-4-amine;
17. 2-(2-ethoxy-3-pyridyl)-5-isopropyl-7-methyl-N-[(2-methylthiazol-5-yl)methyl]imidazo[1,5-b]pyridazin-4-amine;
18. 2-(2-ethoxy-3-pyridyl)-5-isopropyl-7-methyl-N-(1H-pyrazol-4-ylmethyl)imidazo[1,5-b]pyridazin-4-amine;
19. 6-(2-ethoxy-3-pyridyl)-3-isopropyl-1-methyl-N-[(1-methyl pyrazol-4-yl)methyl]pyrazolo[3,4-b]pyridin-4-amine;
20. 6-(2-ethoxy-3-pyridyl)-3-isopropyl-1-methyl-N-[(2-methyltetrazol-5-yl)methyl]pyrazolo[3,4-b]pyridin-4-amine;
21. 6-(2-ethoxy-3-pyridyl)-3-isopropyl-1-methyl-N-[(1-methyl pyrazol-3-yl)methyl]pyrazolo[3,4-b]pyridin-4-amine;
22. 2-(2-ethoxy-3-pyridyl)-5-isopropyl-7-methyl-N-[(1-methyl pyrazol-4-yl)methyl]imidazo[1,5-b]pyridazin-4-amine;
23. 2-(2-ethoxy-3-pyridyl)-5-isopropyl-7-methyl-N-[(2-methyltetrazol-5-yl)methyl]imidazo[1,5-b]pyridazin-4-amine;
24. 2-(2-ethoxy-3-pyridyl)-5-isopropyl-7-methyl-N-[(1-methyl pyrazol-3-yl)methyl]imidazo[1,5-b]pyridazin-4-amine;
25. 6-(2-ethoxy-3-pyridyl)-3-isopropyl-N-[(5-methoxy-3-pyridyl)methyl]-1-methyl-pyrazolo[3,4-b]pyridin-4-amine;
26. 6-(2-ethoxypyridin-3-yl)-3-isopropyl-1-methyl-N-((2-methyl-2H-1,2,3-triazol-4-yl)methyl)-1H-pyrazolo[3,4-b]pyridin-4-amine;
27. 6-(2-ethoxy-3-pyridyl)-3-isopropyl-1-methyl-N-[(2-methyl oxazol-5-yl)methyl]pyrazolo[3,4-b]pyridin-4-amine;
28. 6-(2-ethoxy-3-pyridyl)-3-isopropyl-1-methyl-N-[(2-methylthiazol-5-yl)methyl]pyrazolo[3,4-b]pyridin-4-amine;
29. 6-(2-ethoxy-3-pyridyl)-3-isopropyl-1-methyl-N-[(1-methyltriazol-4-yl)methyl]pyrazolo[3,4-b]pyridin-4-amine;
30. 6-(2-ethoxy-3-pyridyl)-3-isopropyl-1-methyl-N-(1H-pyrazol-4-ylmethyl)pyrazolo[3,4-b]pyridin-4-amine;
31. 6-(2-ethoxy-3-pyridyl)-3-isopropyl-1-methyl-N-[(5-methyl-1,3,4-oxadiazol-2-yl)methyl]pyrazolo[3,4-b]pyridin-4-amine;
32. 6-(2-ethoxy-3-pyridyl)-3-isopropyl-1-methyl-N-[(3-methyl-1,2,4-oxadiazol-5-yl)methyl]pyrazolo[3,4-b]pyridin-4-amine;
33. 3-isopropyl-1-methyl-N-[(1-methyl-1,2,4-triazol-3-yl)methyl]-6-(2-propoxy-3-pyridyl)pyrazolo[3,4-b]pyridin-4-amine;
34. 3-isopropyl-1-methyl-N-[(1-methylimidazol-4-yl)methyl]-6-(2-propoxy-3-pyridyl)pyrazolo[3,4-b]pyridin-4-amine;
35. 6-(2-ethoxy-3-pyridyl)-3-isopropyl-1-methyl-N-[(4-methyl pyrimidin-2-yl)methyl]pyrazolo[3,4-b]pyridin-4-amine;
36. 6-(2-ethoxy-3-pyridyl)-3-isopropyl-1-methyl-N-(pyrimidin-2-ylmethyl)pyrazolo[3,4-b]pyridin-4-amine;

37. 6-(2-ethoxy-3-pyridyl)-3-isopropyl-N-[(6-methoxy-3-pyridyl)methyl]-1-methyl-pyrazolo[3,4-b]pyridin-4-amine;
38. 6-(2-ethoxy-3-pyridyl)-3-isopropyl-1-methyl-N-[[2-(trifluoromethyl)-3-pyridyl]methyl]pyrazolo[3,4-b]pyridin-4-amine;
39. 6-(2-ethoxy-3-pyridyl)-3-isopropyl-N-[(4-methoxy-2-pyridyl)methyl]-1-methyl-pyrazolo[3,4-b]pyridin-4-amine;
40. 6-(2-ethoxy-3-pyridyl)-3-isopropyl-1-methyl-N-(2-pyridylmethyl)pyrazolo[3,4-b]pyridin-4-amine;
41. 6-(2-ethoxy-3-pyridyl)-3-isopropyl-N-[(6-methoxy-2-pyridyl)methyl]-1-methyl-pyrazolo[3,4-b]pyridin-4-amine;
42. 6-(2-ethoxy-3-pyridyl)-3-isopropyl-1-methyl-N-[(6-methyl-2-pyridyl)methyl]pyrazolo[3,4-b]pyridin-4-amine;
43. 2-(2-ethoxy-3-pyridyl)-5-isopropyl-7-methyl-N-(1,2,4-oxadiazol-3-ylmethyl)imidazo[1,5-b]pyridazin-4-amine;
44. 2-(2-ethoxy-3-pyridyl)-5-isopropyl-7-methyl-N-[(2-methyltriazol-4-yl)methyl]imidazo[1,5-b]pyridazin-4-amine;
45. 2-(2-ethoxy-3-pyridyl)-5-isopropyl-7-methyl-N-[(5-methyl-1,3,4-oxadiazol-2-yl)methyl]imidazo[1,5-b]pyridazin-4-amine;
46. 2-(2-ethoxy-3-pyridyl)-5-isopropyl-7-methyl-N-[(3-methyl-1,2,4-oxadiazol-5-yl)methyl]imidazo[1,5-b]pyridazin-4-amine;
47. (−)-2-(2-ethoxy-3-pyridyl)-7-methyl-N-[(1-methylpyrazol-4-yl)methyl]-5-[1-methylpropyl]imidazo[1,5-b]pyridazin-4-amine;
48. (+)-2-(2-ethoxy-3-pyridyl)-7-methyl-N-[(1-methylpyrazol-4-yl)methyl]-5-[1-methylpropyl]imidazo[1,5-b]pyridazin-4-amine;
49. (−)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine;
50. (+)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine;
51. (+)-2-(2-ethoxy-3-pyridyl)-7-methyl-N-(1H-pyrazol-3-ylmethyl)-5-[1-methylpropyl]imidazo[1,5-b]pyridazin-4-amine;
52. (−)-2-(2-ethoxy-3-pyridyl)-7-methyl-N-(1H-pyrazol-3-ylmethyl)-5-[1-methylpropyl]imidazo[1,5-b]pyridazin-4-amine;
53. (+)-2-(2-ethoxy-3-pyridyl)-N-[(2-methoxy-4-pyridyl)methyl]-7-methyl-5-[1-methylpropyl]imidazo[1,5-b]pyridazin-4-amine;
54. (−)-2-(2-ethoxy-3-pyridyl)-N-[(2-methoxy-4-pyridyl)methyl]-7-methyl-5-[1-methylpropyl]imidazo[1,5-b]pyridazin-4-amine;
55. 3-isopropyl-6-(2-methoxy-3-pyridyl)-1-methyl-N-[(1-methyl-1,2,4-triazol-3-yl)methyl]pyrazolo[3,4-b]pyridin-4-amine;
56. 3-(3-isopropyl-1-methyl-4-(((1-methyl-1H-1,2,4-triazol-3-yl)methyl)amino)-1H-pyrazolo[3,4-b]pyridin-6-yl)-1-methylpyridin-2(1H)-one;
57. 3-isopropyl-6-(3-methoxypyrazin-2-yl)-1-methyl-N-((1-methyl-1H-1,2,4-triazol-3-yl)methyl)-1H-pyrazolo[3,4-b]pyridin-4-amine;
58. 3-isopropyl-1-methyl-6-(2-methyl-3-thienyl)-N-[(1-methyl-1,2,4-triazol-3-yl)methyl]pyrazolo[3,4-b]pyridin-4-amine;
59. 3-isopropyl-1-methyl-N-((1-methyl-1H-1,2,4-triazol-3-yl)methyl)-6-(4-methyl oxazol-2-yl)-1H-pyrazolo[3,4-b]pyridin-4-amine;
60. 3-isopropyl-1-methyl-6-(4-methylthiazo-2-yl)-N-[(1-methyl-1,2,4-triazol-3-yl)methyl]pyrazolo[3,4-b]pyridin-4-amine;
61. 3-isopropyl-1-methyl-N-((1-methyl-1H-1,2,4-triazol-3-yl)methyl)-6-(4-methylthiazol-5-yl)-1H-pyrazolo[3,4-b]pyridin-4-amine;
62. 3-isopropyl-1-methyl-6-(5-methylthiazo-2-yl)-N-[(1-methyl-1,2,4-triazol-3-yl)methyl]pyrazolo[3,4-b]pyridin-4-amine;
63. 3-isopropyl-1-methyl-N-[(1-methyl-1,2,4-triazol-3-yl)methyl]-6-phenyl-pyrazolo[3,4-b]pyridin-4-amine;
64. 3-isopropyl-6-(4-methoxypyrimidin-5-yl)-1-methyl-N-[(1-methyl-1,2,4-triazol-3-yl)methyl]pyrazolo[3,4-b]pyridin-4-amine;
65. 3-isopropyl-1-methyl-N-[(1-methyl-1,2,4-triazol-3-yl)methyl]-6-(2-thienyl)pyrazolo[3,4-b]pyridin-4-amine;
66. 6-(3-ethoxypyridazin-4-yl)-3-isopropyl-1-methyl-N-[(1-methyl-1,2,4-triazol-3-yl)methyl]pyrazolo[3,4-b]pyridin-4-amine;
67. 3-isopropyl-1-methyl-N-[(1-methyl-1,2,4-triazol-3-yl)methyl]-6-(3-propoxypyridazin-4-yl)pyrazolo[3,4-b]pyridin-4-amine;
68. 6-(3-ethoxy-4-pyridyl)-3-isopropyl-1-methyl-N-[(1-methyl-1,2,4-triazol-3-yl)methyl]pyrazolo[3,4-b]pyridin-4-amine;
69. 2-(3-ethoxypyridazin-4-yl)-5-isopropyl-7-methyl-N-[(1-methylpyrazol-4-yl)methyl]imidazo[1,5-b]pyridazin-4-amine;
70. 2-(3-ethoxy-4-pyridyl)-5-isopropyl-7-methyl-N-[(1-methylpyrazol-4-yl)methyl]imidazo[1,5-b]pyridazin-4-amine;
71. 5-isopropyl-7-methyl-N-[(1-methylpyrazol-4-yl)methyl]-2-(2-propoxy-3-pyridyl)imidazo[1,5-b]pyridazin-4-amine;
72. 5-isopropyl-7-methyl-N-[(1-methyl-1,2,4-triazol-3-yl)methyl]-2-(2-propoxy-3-pyridyl)imidazo[1,5-b]pyridazin-4-amine;
73. 2-(2-ethoxy-3-pyridyl)-N-[(2-fluoro-3-pyridyl)methyl]-5-isopropyl-7-methyl-imidazo[1,5-b]pyridazin-4-amine;
74. 2-(2-ethoxy-3-pyridyl)-5-isopropyl-7-methyl-N-(2-pyridylmethyl)imidazo[1,5-b]pyridazin-4-amine;
75. 2-(2-ethoxy-3-pyridyl)-5-isopropyl-7-methyl-N-(pyrimidin-2-ylmethyl)imidazo[1,5-b]pyridazin-4-amine;
76. 2-(2-ethoxy-3-pyridyl)-N-[(5-fluoropyrimidin-2-yl)methyl]-5-isopropyl-7-methyl-imidazo[1,5-b]pyridazin-4-amine;
77. 2-(2-ethoxy-3-pyridyl)-5-isopropyl-N-[(2-methoxy-3-pyridyl)methyl]-7-methyl-imidazo[1,5-b]pyridazin-4-amine;
78. 2-(2-ethoxy-3-pyridyl)-N-(imidazo[1,5-a]pyridin-5-ylmethyl)-5-isopropyl-7-methyl-imidazo[1,5-b]pyridazin-4-amine;
79. 2-(2-ethoxy-3-pyridyl)-N-(imidazo[1,2-a]pyridin-5-ylmethyl)-5-isopropyl-7-methyl-imidazo[1,5-b]pyridazin-4-amine;
80. 2-(2-ethoxy-3-pyridyl)-5-isopropyl-7-methyl-N-[[2-(trifluoromethyl)-3-pyridyl]methyl]imidazo[1,5-b]pyridazin-4-amine;
81. 2-(1,3-benzoxazol-7-yl)-5-isopropyl-7-methyl-N-[(1-methyl-1,2,4-triazol-3-yl)methyl]imidazo[1,5-b]pyridazin-4-amine;

or a pharmaceutically acceptable salt of any of these compounds.

E36. A compound of any one of embodiments 1-35 or a pharmaceutically acceptable salt thereof, wherein said compound has a PDE1A, PDE1B or PDE1C $IC_{50}$ value, determined as described in the section "PDE1 inhibition assay", of 10 micro molar or less, such as 5 micro molar or less, such as 4 micro molar or less, such as 3 micro molar or less, such as 2 micro molar or less, such as 1 micro molar or less, such as 500 nM or less, such as 400 nM or less, such as 300 nM or less, such as 200 nM or less, such as 100 nM or less.

E37. A compound of any one of embodiments 1-35 or a pharmaceutically acceptable salt thereof, wherein said compound has at least two-fold lower PDE1B $IC_{50}$ value, three-fold lower PDE1B $IC_{50}$ value, four-fold lower or five-fold lower PDE1B $IC_{50}$ value than PDE1A $IC_{50}$ value and/or PDE1C $IC_{50}$ value.

E38. A compound of any one of embodiments 1-37 or a pharmaceutically acceptable salt thereof, for use in therapy.

E39. A compound according to any of embodiments 1-37 or a pharmaceutically acceptable salt thereof, for use as a medicament.

E40. A pharmaceutical composition comprising a therapeutically effective amount of a compound of any one of embodiments 1-37 or a pharmaceutically acceptable salt thereof, and one or more pharmaceutically acceptable carriers, diluents and/or excipients.

E41. The pharmaceutical composition according to embodiment 40 for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E42. The pharmaceutical composition according to embodiment 40, wherein said pharmaceutical composition further comprises a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E43. The pharmaceutical composition according to embodiment 42, wherein said composition is for use in the treatment of a neurodegenerative disorder selected from the group consisting of Alzheimer's Disease, Parkinson's Disease and Huntington's Disease.

E44. The pharmaceutical composition according to embodiment 40, further comprising a second compound, which compound is useful in the treatment of a psychiatric disorder.

E45. The pharmaceutical composition according to embodiment 44, wherein said second compound has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E46. The pharmaceutical composition according to embodiment 44, wherein said second compound is selected from the list comprising clozapine, risperidone, paliperidone, olanzapine, quetiapine, amisulpride, ziprasidone, aripiprazole, brexpiprazole, asenapine, haloperidol, iloperidone, lurasidone, chlorpromazine, blonanserin, perphenazine, levomepromazine, sulpiride, fluphenazine, zuclopenthixol, flupenthixol and cariprazine.

E47. The pharmaceutical composition according to any of embodiments 44-46, wherein said composition is for use in the treatment of a psychiatric disorder such as Attention Deficit Hyperactivity Disorder (ADHD), depression, anxiety, narcolepsy, cognitive impairment and cognitive impairment associated with schizophrenia (CIAS).

E48. A compound according to any of embodiments 1-37 or a pharmaceutically acceptable salt thereof, for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E49. The compound according to any of embodiments 1-37 or a pharmaceutically acceptable salt thereof, for the use in the treatment of a neurodegenerative disorder selected from the group consisting of Alzheimer's Disease, Parkinson's Disease and Huntington's Disease, wherein said compound is used in combination with a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E50. The compound according to any of embodiments 1-37 or a pharmaceutically acceptable salt thereof, for the use in the treatment of a psychiatric disorder such as Attention Deficit Hyperactivity Disorder (ADHD), depression, anxiety, narcolepsy, cognitive impairment and cognitive impairment associated with schizophrenia (CIAS), wherein said compound is used in combination with a second compound, which compound is useful in the treatment of a psychiatric disorder.

E51. The compound or pharmaceutically acceptable salt thereof for the use according to embodiment 50, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E52. The compound or pharmaceutically acceptable salt thereof for the use according to embodiment 50, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidol, iloperidone, lurasidone, chlorpromazine, blonanserin, perphenazine, levomepromazine, sulpiride, fluphenazine, zuclopenthixol, flupenthixol and cariprazine.

E53. A method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to any of embodiments 1-37 or a pharmaceutically acceptable salt thereof, to a patient in need thereof.

E54. A method for the treatment of a neurodegenerative disorder, selected from the group consisting of Alzheimer's Disease, Parkinson's Disease and Huntington's Disease, which method comprises the administration of a therapeutically effective amount of a compound according to any of embodiments 1-37 or a pharmaceutically acceptable salt thereof, in combination with a therapeutically effective amount of a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody; to a patient in need thereof.

E55. A method for the treatment of a psychiatric disorder such as Attention Deficit Hyperactivity Disorder (ADHD), depression, anxiety, narcolepsy, cognitive impairment and cognitive impairment associated with schizophrenia (CIAS), which method comprises the administration of a therapeutically effective amount of a compound according to any of embodiments 1-37 or a pharmaceutically acceptable salt thereof, in combination with a therapeutically effective amount of a second compound, which compound is useful in the treatment of a psychiatric disorder; to a patient in need thereof.

E56. The method according to embodiment 55, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E57. The method according to embodiment 55, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidol, iloperidone, lurasidone, chlorpromazine, blonanserin, perphenazine, levomepromazine, sulpiride, fluphenazine, zuclopenthixol, flupenthixol and cariprazine.

E58. Use of a compound according to any of embodiments 1-37 or a pharmaceutically acceptable salt thereof, in the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E59. Use of a compound according to any of embodiments 1-37 or a pharmaceutically acceptable salt thereof, in the manufacture of a medicament for the treatment of a neurodegenerative disorder, selected from the group consisting of Alzheimer's Disease, Parkinson's Disease and Huntington's Disease, wherein said medicament is for use in combination with a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E60. Use of a compound according to any of embodiments 1-37 or a pharmaceutically acceptable salt thereof, in the manufacture of a medicament for the treatment of a psychiatric disorder such as Attention Deficit Hyperactivity Disorder (ADHD), depression, anxiety, narcolepsy, cognitive impairment and cognitive impairment associated with schizophrenia (CIAS), wherein said medicament is for use in combination with a second compound, which compound is useful in the treatment of a psychiatric disorder.

E61. The use according to embodiment 60, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E62. The use according to embodiment 61, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidol, iloperidone, lurasidone, chlorpromazine, blonanserin, perphenazine, levomepromazine, sulpiride, fluphenazine, zuclopenthixol, flupenthixol and cariprazine.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Compounds of the Invention

TABLE 1

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 1 | 6-(2-ethoxy-3-pyridyl)-3-isopropyl-1-methyl-N-[(1-methylimidazol-4-yl)methyl]pyrazolo[3,4-b]pyridin-4-amine | 7.2 | 0.71 | 12 |
| 2 | 6-(2-ethoxy-3-pyridyl)-3-isopropyl-1-methyl-N-[(2-methyloxazol-4-yl)methyl]pyrazolo[3,4-b]pyridin-4-amine | 81 | 15 | 99 |
| 3 | 6-(2-ethoxy-3-pyridyl)-3-isopropyl-1-methyl-N-(1H-pyrazol-3-ylmethyl)pyrazolo[3,4-b]pyridin-4-amine | 56 | 4.3 | 58 |
| 4 | 6-(2-ethoxy-3-pyridyl)-3-isopropyl-1-methyl-N-[(1-methyl-1,2,4-triazol-3-yl)methyl]pyrazolo[3,4-b]pyridin-4-amine | 11 | 0.34 | 13 |
| 5 | 6-(2-ethoxy-3-pyridyl)-3-isopropyl-1-methyl-N-[(5-methyl-1,2,4-oxadiazol-3-yl)methyl]pyrazolo[3,4-b]pyridin-4-amine | 8.9 | 1.1 | 19 |
| 6 | 6-(2-ethoxy-3-pyridyl)-3-isopropyl-1-methyl-N-[(5-methyl-1H-pyrazol-3-yl)methyl]pyrazolo[3,4-b]pyridin-4-amine | 14 | 1.2 | 20 |
| 7 | 6-(2-ethoxy-3-pyridyl)-3-isopropyl-N-[(2-methoxy-4-pyridyl)methyl]-1-methyl-pyrazolo[3,4-b]pyridin-4-amine | 14 | 2.6 | 18 |
| 8 | 2-(2-ethoxy-3-pyridyl)-5-isopropyl-7-methyl-N-[(1-methylimidazol-4-yl)methyl]imidazo[1,5-b]pyridazin-4-amine | 2.4 | 0.22 | 2.6 |
| 9 | 2-(2-ethoxy-3-pyridyl)-5-isopropyl-7-methyl-N-[(2-methyloxazol-4-yl)methyl]imidazo[1,5-b]pyridazin-4-amine | 30 | 4.3 | 29 |
| 10 | 2-(2-ethoxy-3-pyridyl)-5-isopropyl-7-methyl-N-(1H-pyrazol-3-ylmethyl)imidazo[1,5-b]pyridazin-4-amine | 15 | 1.6 | 13 |
| 11 | 2-(2-ethoxy-3-pyridyl)-5-isopropyl-7-methyl-N-[(1-methyl-1,2,4-triazol-3-yl)methyl]imidazo[1,5-b]pyridazin-4-amine | 2 | 0.28 | 2.6 |
| 12 | 2-(2-ethoxy-3-pyridyl)-5-isopropyl-7-methyl-N-[(5-methyl-1,2,4-oxadiazol-3-yl)methyl]imidazo[1,5-b]pyridazin-4-amine | 3.6 | 0.35 | 4 |
| 13 | 2-(2-ethoxy-3-pyridyl)-5-isopropyl-7-methyl-N-[(5-methyl-1H-pyrazol-3-yl)methyl]imidazo[1,5-b]pyridazin-4-amine | 4.1 | 0.31 | 2.7 |
| 14 | 2-(2-ethoxy-3-pyridyl)-5-isopropyl-N-[(5-methoxy-3-pyridyl)methyl]-7-methyl-imidazo[1,5-b]pyridazin-4-amine | 6.2 | 1.5 | 5.1 |
| 15 | 2-(2-ethoxy-3-pyridyl)-5-isopropyl-N-[(2-methoxy-4-pyridyl)methyl]-7-methyl-imidazo[1,5-b]pyridazin-4-amine | 7.3 | 1.7 | 9 |
| 16 | 2-(2-ethoxy-3-pyridyl)-5-isopropyl-7-methyl-N-[(2-methyloxazol-5-yl)methyl]imidazo[1,5-b]pyridazin-4-amine | 19 | 2.8 | 16 |
| 17 | 2-(2-ethoxy-3-pyridyl)-5-isopropyl-7-methyl-N-[(2-methylthiazol-5-yl)methyl]imidazo[1,5-b]pyridazin-4-amine | 6.1 | 1.5 | 5.7 |
| 18 | 2-(2-ethoxy-3-pyridyl)-5-isopropyl-7-methyl-N-(1H-pyrazol-4-ylmethyl)imidazo[1,5-b]pyridazin-4-amine | 33 | 5.7 | 16 |
| 19 | 6-(2-ethoxy-3-pyridyl)-3-isopropyl-1-methyl-N-[(1-methylpyrazol-4-yl)methyl]pyrazolo[3,4-b]pyridin-4-amine | 44 | 5.8 | 56 |
| 20 | 6-(2-ethoxy-3-pyridyl)-3-isopropyl-1-methyl-N-[(2-methyltetrazol-5-yl)methyl]pyrazolo[3,4-b]pyridin-4-amine | 16 | 2.8 | 30 |
| 21 | 6-(2-ethoxy-3-pyridyl)-3-isopropyl-1-methyl-N-[(1-methylpyrazol-3-yl)methyl]pyrazolo[3,4-b]pyridin-4-amine | 30 | 5.3 | 36 |
| 22 | 2-(2-ethoxy-3-pyridyl)-5-isopropyl-7-methyl-N-[(1-methylpyrazol-4-yl)methyl]imidazo[1,5-b]pyridazin-4-amine | 17 | 1.8 | 16 |
| 23 | 2-(2-ethoxy-3-pyridyl)-5-isopropyl-7-methyl-N-[(2-methyltetrazol-5-yl)methyl]imidazo[1,5-b]pyridazin-4-amine | 5.4 | 0.77 | 4.7 |
| 24 | 2-(2-ethoxy-3-pyridyl)-5-isopropyl-7-methyl-N-[(1-methylpyrazol-3-yl)methyl]imidazo[1,5-b]pyridazin-4-amine | 14 | 1.8 | 13 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 25 | 6-(2-ethoxy-3-pyridyl)-3-isopropyl-N-[(5-methoxy-3-pyridyl)methyl]-1-methyl-pyrazolo[3,4-b]pyridin-4-amine | 16 | 6.3 | 18 |
| 26 | 6-(2-ethoxypyridin-3-yl)-3-isopropyl-1-methyl-N-((2-methyl-2H-1,2,3-triazol-4-yl)methyl)-1H-pyrazolo[3,4-b]pyridin-4-amine | 110 | 18 | 75 |
| 27 | 6-(2-ethoxy-3-pyridyl)-3-isopropyl-1-methyl-N-[(2-methyloxazol-5-yl)methyl]pyrazolo[3,4-b]pyridin-4-amine | 53 | 10 | 60 |
| 28 | 6-(2-ethoxy-3-pyridyl)-3-isopropyl-1-methyl-N-[(2-methylthiazol-5-yl)methyl]pyrazolo[3,4-b]pyridin-4-amine | 14 | 4.4 | 13 |
| 29 | 6-(2-ethoxy-3-pyridyl)-3-isopropyl-1-methyl-N-[(1-methyltriazol-4-yl)methyl]pyrazolo[3,4-b]pyridin-4-amine | 18 | 1.6 | 33 |
| 30 | 6-(2-ethoxy-3-pyridyl)-3-isopropyl-1-methyl-N-(1H-pyrazol-4-ylmethyl)pyrazolo[3,4-b]pyridin-4-amine | 85 | 16 | 76 |
| 31 | 6-(2-ethoxy-3-pyridyl)-3-isopropyl-1-methyl-N-[(5-methyl-1,3,4-oxadiazol-2-yl)methyl]pyrazolo[3,4-b]pyridin-4-amine | 110 | 16 | 110 |
| 32 | 6-(2-ethoxy-3-pyridyl)-3-isopropyl-1-methyl-N-[(3-methyl-1,2,4-oxadiazol-5-yl)methyl]pyrazolo[3,4-b]pyridin-4-amine | 82 | 7.8 | 63 |
| 33 | 3-isopropyl-1-methyl-N-[(1-methyl-1,2,4-triazol-3-yl)methyl]-6-(2-propoxy-3-pyridyl)pyrazolo[3,4-b]pyridin-4-amine | 3.4 | 0.42 | 5.2 |
| 34 | 3-isopropyl-1-methyl-N-[(1-methylimidazol-4-yl)methyl]-6-(2-propoxy-3-pyridyl)pyrazolo[3,4-b]pyridin-4-amine | 2.7 | 0.29 | 3.8 |
| 35 | 6-(2-ethoxy-3-pyridyl)-3-isopropyl-1-methyl-N-[(4-methylpyrimidin-2-yl)methyl]pyrazolo[3,4-b]pyridin-4-amine | 200 | 25 | 180 |
| 36 | 6-(2-ethoxy-3-pyridyl)-3-isopropyl-1-methyl-N-(pyrimidin-2-ylmethyl)pyrazolo[3,4-b]pyridin-4-amine | 50 | 4 | 77 |
| 37 | 6-(2-ethoxy-3-pyridyl)-3-isopropyl-N-[(6-methoxy-3-pyridyl)methyl]-1-methyl-pyrazolo[3,4-b]pyridin-4-amine | 120 | 27 | 46 |
| 38 | 6-(2-ethoxy-3-pyridyl)-3-isopropyl-1-methyl-N-[[2-(trifluoromethyl)-3-pyridyl]methyl]pyrazolo[3,4-b]pyridin-4-amine | 180 | 33 | 180 |
| 39 | 6-(2-ethoxy-3-pyridyl)-3-isopropyl-N-[(4-methoxy-2-pyridyl)methyl]-1-methyl-pyrazolo[3,4-b]pyridin-4-amine | 27 | 3.4 | 25 |
| 40 | 6-(2-ethoxy-3-pyridyl)-3-isopropyl-1-methyl-N-(2-pyridylmethyl)pyrazolo[3,4-b]pyridin-4-amine | 68 | 8.9 | 82 |
| 41 | 6-(2-ethoxy-3-pyridyl)-3-isopropyl-N-[(6-methoxy-2-pyridyl)methyl]-1-methyl-pyrazolo[3,4-b]pyridin-4-amine | 440 | 110 | 560 |
| 42 | 6-(2-ethoxy-3-pyridyl)-3-isopropyl-1-methyl-N-[(6-methyl-2-pyridyl)methyl]pyrazolo[3,4-b]pyridin-4-amine | 180 | 20 | 200 |
| 43 | 2-(2-ethoxy-3-pyridyl)-5-isopropyl-7-methyl-N-(1,2,4-oxadiazol-3-ylmethyl)imidazo[1,5-b]pyridazin-4-amine | 40 | 5.8 | 34 |
| 44 | 2-(2-ethoxy-3-pyridyl)-5-isopropyl-7-methyl-N-[(2-methyltriazol-4-yl)methyl]imidazo[1,5-b]pyridazin-4-amine | 38 | 5.1 | 24 |
| 45 | 2-(2-ethoxy-3-pyridyl)-5-isopropyl-7-methyl-N-[(5-methyl-1,3,4-oxadiazol-2-yl)methyl]imidazo[1,5-b]pyridazin-4-amine | 42 | 7.8 | 37 |
| 46 | 2-(2-ethoxy-3-pyridyl)-5-isopropyl-7-methyl-N-[(3-methyl-1,2,4-oxadiazol-5-yl)methyl]imidazo[1,5-b]pyridazin-4-amine | 21 | 4.1 | 14 |
| 47 | (−)-2-(2-ethoxy-3-pyridyl)-7-methyl-N-[(1-methylpyrazol-4-yl)methyl]-5-[1-methylpropyl]imidazo[1,5-b]pyridazin-4-amine | 44 | 7.5 | 32 |
| 48 | (+)-2-(2-ethoxy-3-pyridyl)-7-methyl-N-[(1-methylpyrazol-4-yl)methyl]-5-[1-methylpropyl]imidazo[1,5-b]pyridazin-4-amine | 5.8 | 0.64 | 4.9 |
| 49 | (−)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine | 14 | 1.4 | 7.6 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 50 | (+)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine | 5.6 | 0.53 | 2.4 |
| 51 | (+)-2-(2-ethoxy-3-pyridyl)-7-methyl-N-(1H-pyrazol-3-ylmethyl)-5-[1-methylpropyl]imidazo[1,5-b]pyridazin-4-amine | 57 | 4.3 | 31 |
| 52 | (−)-2-(2-ethoxy-3-pyridyl)-7-methyl-N-(1H-pyrazol-3-ylmethyl)-5-[1-methylpropyl]imidazo[1,5-b]pyridazin-4-amine | 12 | 0.65 | 6.1 |
| 53 | (+)-2-(2-ethoxy-3-pyridyl)-N-[(2-methoxy-4-pyridyl)methyl]-7-methyl-5-[1-methylpropyl]imidazo[1,5-b]pyridazin-4-amine | 62 | 12 | 11 |
| 54 | (−)-2-(2-ethoxy-3-pyridyl)-N-[(2-methoxy-4-pyridyl)methyl]-7-methyl-5-[1-methylpropyl]imidazo[1,5-b]pyridazin-4-amine | 9.6 | 1.8 | 4.4 |
| 55 | 3-isopropyl-6-(2-methoxy-3-pyridyl)-1-methyl-N-[(1-methyl-1,2,4-triazol-3-yl)methyl]pyrazolo[3,4-b]pyridin-4-amine | 130 | 30 | 45 |
| 56 | 3-(3-isopropyl-1-methyl-4-(((1-methyl-1H-1,2,4-triazol-3-yl)methyl)amino)-1H-pyrazolo[3,4-b]pyridin-6-yl)-1-methylpyridin-2(1H)-one | 290 | 52 | 480 |
| 57 | 3-isopropyl-6-(3-methoxypyrazin-2-yl)-1-methyl-N-((1-methyl-1H-1,2,4-triazol-3-yl)methyl)-1H-pyrazolo[3,4-b]pyridin-4-amine | 91 | 22 | 6.5 |
| 58 | 3-isopropyl-1-methyl-6-(2-methyl-3-thienyl)-N-[(1-methyl-1,2,4-triazol-3-yl)methyl]pyrazolo[3,4-b]pyridin-4-amine | 29 | 4.6 | 31 |
| 59 | 3-isopropyl-1-methyl-N-((1-methyl-1H-1,2,4-triazol-3-yl)methyl)-6-(4-methyloxazol-2-yl)-1H-pyrazolo[3,4-b]pyridin-4-amine | 99 | 14 | 67 |
| 60 | 3-isopropyl-1-methyl-6-(4-methylthiazol-2-yl)-N-[(1-methyl-1,2,4-triazol-3-yl)methyl]pyrazolo[3,4-b]pyridin-4-amine | 48 | 8.8 | 74 |
| 61 | 3-isopropyl-1-methyl-N-((1-methyl-1H-1,2,4-triazol-3-yl)methyl)-6-(4-methylthiazol-5-yl)-1H-pyrazolo[3,4-b]pyridin-4-amine | 32 | 4.6 | 46 |
| 62 | 3-isopropyl-1-methyl-6-(5-methylthiazol-2-yl)-N-[(1-methyl-1,2,4-triazol-3-yl)methyl]pyrazolo[3,4-b]pyridin-4-amine | 280 | 170 | 150 |
| 63 | 3-isopropyl-1-methyl-N-[(1-methyl-1,2,4-triazol-3-yl)methyl]-6-phenyl-pyrazolo[3,4-b]pyridin-4-amine | 83 | 21 | 36 |
| 64 | 3-isopropyl-6-(4-methoxypyrimidin-5-yl)-1-methyl-N-[(1-methyl-1,2,4-triazol-3-yl)methyl]pyrazolo[3,4-b]pyridin-4-amine | 66 | 13 | 2.9 |
| 65 | 3-isopropyl-1-methyl-N-[(1-methyl-1,2,4-triazol-3-yl)methyl]-6-(2-thienyl)pyrazolo[3,4-b]pyridin-4-amine | 31 | 5.1 | 46 |
| 66 | 6-(3-ethoxypyridazin-4-yl)-3-isopropyl-1-methyl-N-[(1-methyl-1,2,4-triazol-3-yl)methyl]pyrazolo[3,4-b]pyridin-4-amine | 27 | 3.7 | 39 |
| 67 | 3-isopropyl-1-methyl-N-[(1-methyl-1,2,4-triazol-3-yl)methyl]-6-(3-propoxypyridazin-4-yl)pyrazolo[3,4-b]pyridin-4-amine | 7.8 | 2.7 | 19 |
| 68 | 6-(3-ethoxy-4-pyridyl)-3-isopropyl-1-methyl-N-[(1-methyl-1,2,4-triazol-3-yl)methyl]pyrazolo[3,4-b]pyridin-4-amine | 58 | 5.5 | 59 |
| 69 | 2-(3-ethoxypyridazin-4-yl)-5-isopropyl-7-methyl-N-[(1-methylpyrazol-4-yl)methyl]imidazo[1,5-b]pyridazin-4-amine | 24 | 5.2 | 25 |
| 70 | 2-(3-ethoxy-4-pyridyl)-5-isopropyl-7-methyl-N-[(1-methylpyrazol-4-yl)methyl]imidazo[1,5-b]pyridazin-4-amine | 21 | 6.3 | 28 |
| 71 | 5-isopropyl-7-methyl-N-[(1-methylpyrazol-4-yl)methyl]-2-(2-propoxy-3-pyridyl)imidazo[1,5-b]pyridazin-4-amine | 3.3 | 1 | 7 |
| 72 | 5-isopropyl-7-methyl-N-[(1-methyl-1,2,4-triazol-3-yl)methyl]-2-(2-propoxy-3-pyridyl)imidazo[1,5-b]pyridazin-4-amine | 1.4 | 0.27 | 1.1 |
| 73 | 2-(2-ethoxy-3-pyridyl)-N-[(2-fluoro-3-pyridyl)methyl]-5-isopropyl-7-methyl-imidazo[1,5-b]pyridazin-4-amine | 33 | 3.6 | 29 |
| 74 | 2-(2-ethoxy-3-pyridyl)-5-isopropyl-7-methyl-N-(2-pyridylmethyl)imidazo[1,5-b]pyridazin-4-amine | 180 | 27 | 190 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 75 | 2-(2-ethoxy-3-pyridyl)-5-isopropyl-7-methyl-N-(pyrimidin-2-ylmethyl)imidazo[1,5-b]pyridazin-4-amine | 11 | 0.13 | 24 |
| 76 | 2-(2-ethoxy-3-pyridyl)-N-[(5-fluoropyrimidin-2-yl)methyl]-5-isopropyl-7-methyl-imidazo[1,5-b]pyridazin-4-amine | 89 | 17 | 110 |
| 77 | 2-(2-ethoxy-3-pyridyl)-5-isopropyl-N-[(2-methoxy-3-pyridyl)methyl]-7-methyl-imidazo[1,5-b]pyridazin-4-amine | 48 | 9 | 48 |
| 78 | 2-(2-ethoxy-3-pyridyl)-N-(imidazo[1,5-a]pyridin-5-ylmethyl)-5-isopropyl-7-methyl-imidazo[1,5-b]pyridazin-4-amine | 61 | 5.5 | 39 |
| 79 | 2-(2-ethoxy-3-pyridyl)-N-(imidazo[1,2-a]pyridin-5-ylmethyl)-5-isopropyl-7-methyl-imidazo[1,5-b]pyridazin-4-amine | 35 | 28 | 19 |
| 80 | 2-(2-ethoxy-3-pyridyl)-5-isopropyl-7-methyl-N-[[2-(trifluoromethyl)-3-pyridyl]methyl]imidazo[1,5-b]pyridazin-4-amine | 74 | 15 | 72 |
| 81 | 2-(1,3-benzoxazol-7-yl)-5-isopropyl-7-methyl-N-[(1-methyl-1,2,4-triazol-3-yl)methyl]imidazo[1,5-b]pyridazin-4-amine | 3.8 | 0.29 | 2.5 |

Table 1 lists the IC$_{50}$ values for inhibition of PDE1 by the compounds of the invention. The IC$_{50}$ value refers to the concentration (nM) of the compound required to reach 50% inhibition of the PDE1 enzyme at the specified substrate concentration. The PDE1 assay is described in the Experimental Section.

Experimental Section

Preparation of the Compounds of the Invention—General Methods

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XIII" (published with Wiley-Interscience, ISSN: 1934-4783). Preferred methods include, but are not limited to, those described below.

The schemes are representative of methods useful in synthesizing the compounds of the present invention. They are not to constrain the scope of the invention in any way.

Method 1:

Scheme 1

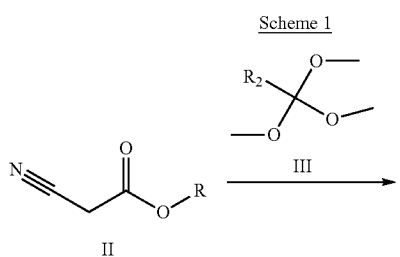

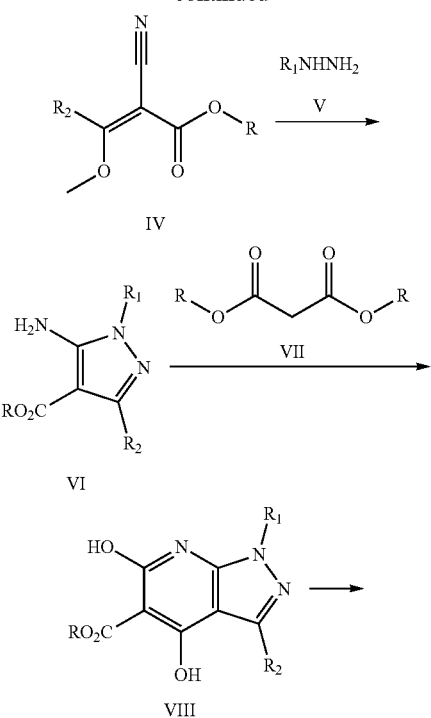

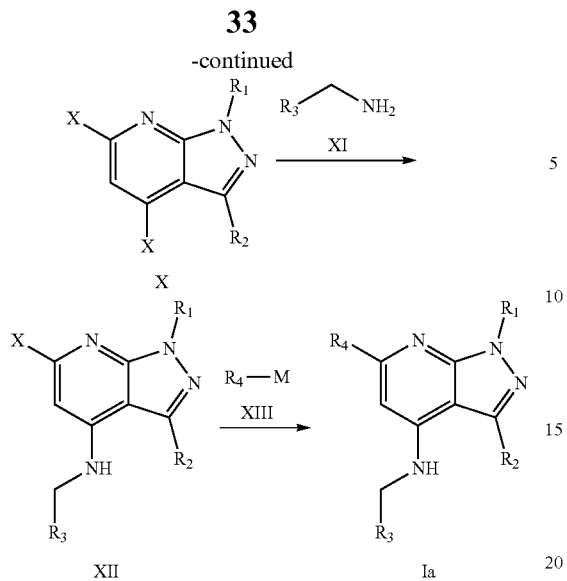

where $R_1$, $R_2$, $R_3$ and $R_4$ are as described for formula (I); formula Ia is formula (I) with Y1=N—R1, Y2=C and Y3=C; R is an alkyl group such as methyl or ethyl, M is a metal, a boronic acid moiety or a boronic acid ester moiety, and X is a halogen such as chlorine or bromine.

Compounds of general formula IV (Scheme 1) can be prepared by the reaction of compounds of general formulae II and III in the presence of an acid such as acetic acid. Reaction of compounds of general formula IV with hydrazines of general formula V gives compounds of general formula VI. Reaction of compounds of general formulae VI and VII in the presence of a base such as sodium ethoxide followed by a ring-closing reaction gives compounds of general formula VIII. Hydrolysis and decarboxylation of compounds of general formula VIII gives compounds of general formula IX. Treatment of compounds of general formula IX with reagents such as phosphoryl chloride or phosphoryl bromide gives compounds of general formula X. In a substitution reaction of compounds of general formulae X and XI, compounds of general formula XII are formed. Compounds of general formula Ia can be prepared from compounds of general formulae XII and XIII in the presence of a palladium catalyst such as [1,1'-bis(diphenylphosphino)ferrocene]palladium(II) dichloride (PdCl$_2$(dppf)) and a base such as cesium carbonate or other Suzuki-Miyaura coupling reaction conditions known to chemists skilled in the art of organic synthesis.

Method 2:

Scheme 2

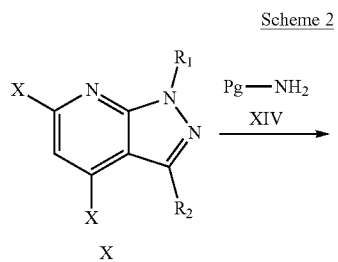

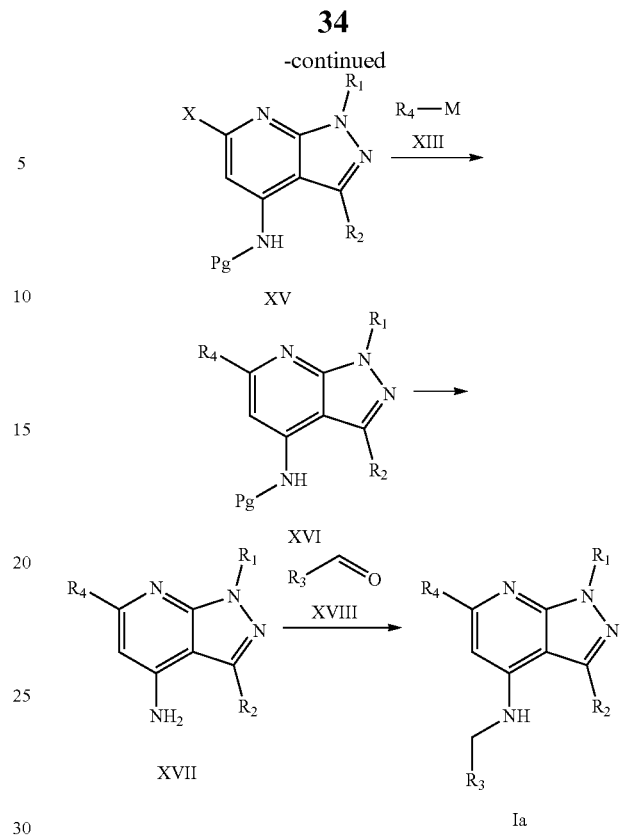

where $R_1$, $R_2$, $R_3$ and $R_4$ are as described for formula (I), formula Ia is formula (I) with Y1=N—R1, Y2=C and Y3=C, M is a metal, a boronic acid moiety or a boronic acid ester moiety, and Pg is a protection group such as para-methoxy benzyl.

Compounds of general formula XV (Scheme 2) can be prepared by treatment of compounds of general formula X with compounds of general formula XIV in the presence of a base such as but not limited to cesium fluoride or N,N-diisopropylethylamine. Compounds of general formula XVI can be prepared from compounds of general formulae XV and XIII in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis. Compounds of general formula XVII can be prepared by the deprotection of compounds of general formula XVI. If the protection group is para-methoxy benzyl, the deprotection can be performed by treatment with an acid such as trifluoroacetic acid. Compounds of general formula Ia can be prepared by reductive amination of compounds of general formula XVII with the appropriate aldehyde such as compounds of general formula XVIII.

Method 3:

Scheme 3

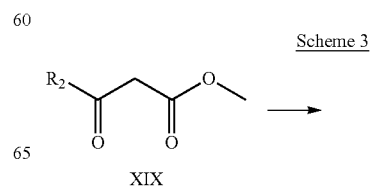

-continued

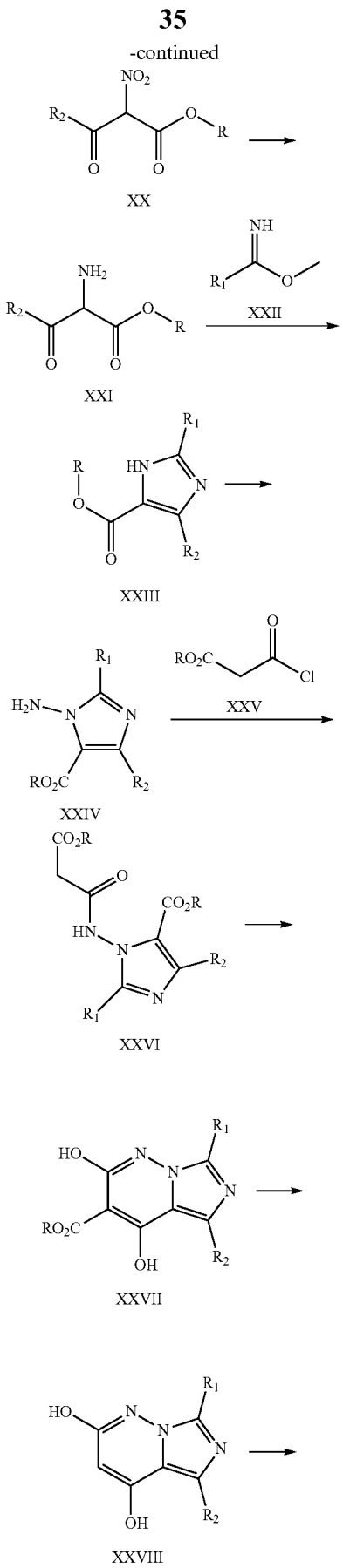

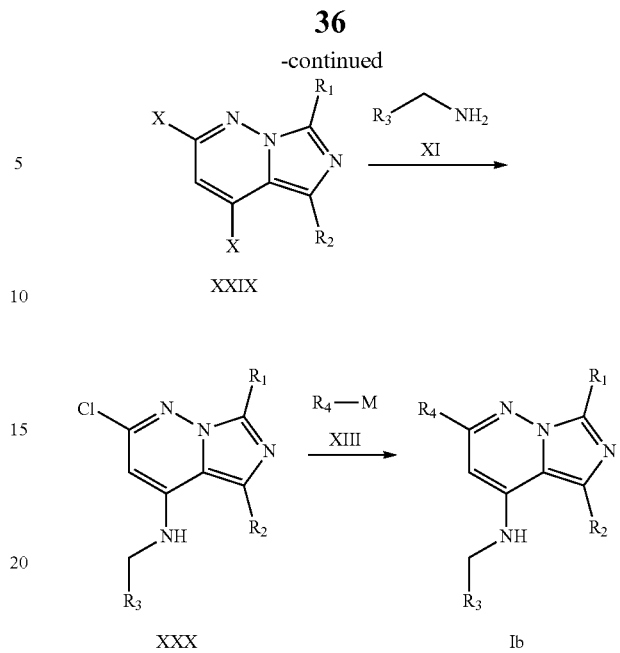

where $R_1$, $R_2$, $R_3$ and $R_4$ are as described for formula (I); formula Ib is formula (I) with Y1=C—R1, Y2=N and Y3=C; R is an alkyl group such as methyl or ethyl, M is a metal, a boronic acid moiety or a boronic acid ester moiety, and X is a halogen such as chlorine or bromine.

Compounds of general formula XX can be prepared by nitration of compounds of general formula XIX by using a reagent such as sodium nitrite. Reduction of compounds of general formula XX using conditions such as hydrogen and palladium gives compounds of general formula XXI. Compounds of general formula XXIII can be prepared from compounds of general formulae XXI and XXII in the presence of a base such as triethylamine. N-amination of compounds of general formula XXIII using a base such as LiHMDS (lithium bis(trimethylsilyl)amide) and an amination reagent such as (aminooxy)diphenylphosphine oxide gives compounds of general formula XXIV. Acylation of compounds of general formula XXIV with compounds of general formula XXV gives compounds of general formula XXVI. Treatment of compounds of general formula XXVI with a base such as sodium tert-butoxide gives compounds of general formula XXVII. Hydrolysis of compounds of general formula XXVII using an aqueous base such as sodium hydroxide followed by decarboxylation gives compounds of general formula XXVIII. Treatment of compounds of general formula XXVIII with reagents such as phosphoryl chloride or phosphoryl bromide gives compounds of general formula XXIX. In a substitution reaction of compounds of general formulae XXIX and XI, compounds of general formula XXX are formed. Compounds of general formula Ib can be prepared from compounds of general formulae XXX and XIII in the presence of a palladium catalyst such as [1,1'-bis(diphenylphosphino)ferrocene]palladium(II) dichloride ($PdCl_2$(dppf)) and a base such as cesium carbonate or other Suzuki-Miyaura coupling reaction conditions known to chemists skilled in the art of organic synthesis.

Method 4:

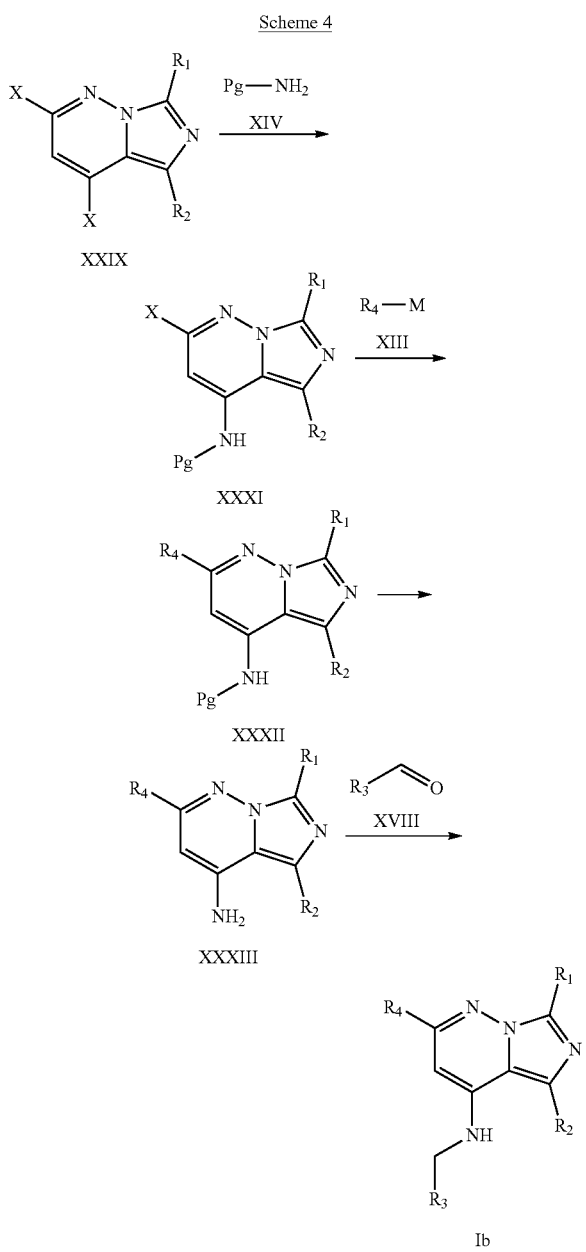

where $R_1$, $R_2$, $R_3$ and $R_4$ are as described for formula (I), formula Ib is formula (I) with Y1=C—R1, Y2=N and Y3=C, M is a metal, a boronic acid moiety or a boronic acid ester moiety, Pg is a protection group such as para-methoxy benzyl, and X is a halogen such as chlorine or bromine.

Compounds of general formula XXXI (Scheme 4) can be prepared by treatment of compounds of general formula XXIX with compounds of general formula XIV in the presence of a base such as but not limited to cesium fluoride or N,N-diisopropylethylamine.

Compounds of general formula XXXII can be prepared from compounds of general formulae XXXI and XIII in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis. Compounds of general formula XXXIII can be prepared by the deprotection of compounds of general formula XXXII. If the protection group is para-methoxy benzyl, the deprotection can be performed by treatment with an acid such as trifluoroacetic acid. Compounds of general formula Ib can be prepared by reductive amination of compounds of general formula XXXIII with the appropriate aldehyde such as compounds of general formula XVIII.

Method 5:

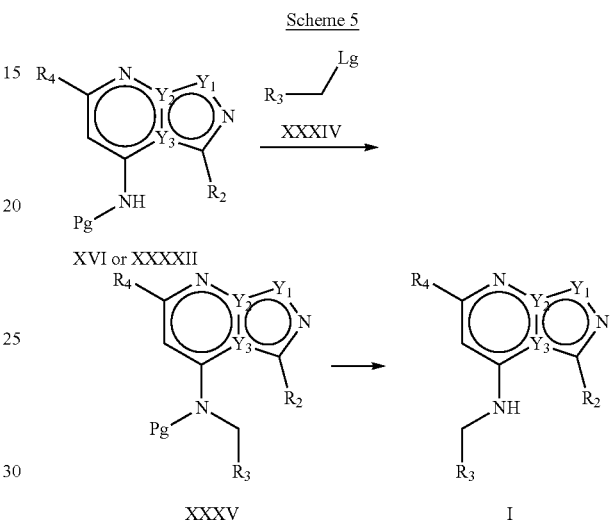

where $Y_1$, $Y_2$, $Y_3$, $R_1$, $R_2$, $R_3$ and $R_4$ are as described for formula (I). Pg is a protecting group such as p-methoxybenzyl and Lg is a leaving group such as chlorine, bromine, iodine, 4-methylbenzenesulfonate or methanesulfonate.

Compounds of general formula XXXV (Scheme 5) can be prepared by deprotonation of compounds of general formula XVI or XXXXII with a base such as sodium hydride followed by alkylation with compounds of general formula XXXIV. Compounds of general formula I can be prepared by removal of the protecting group (Pg) using reaction conditions known to chemists skilled in the art of organic synthesis, e.g. by treatment with trifluoroacetic acid when Pg is p-methoxybenzyl.

LC-MS Methods

Method A:

An Agilent 1200 LCMS system with ELS detector was used. Phenomenex Luna-C18, 5 µm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method B:

An Agilent 1200 LCMS system with ELS detector was used. Column: Waters XBridge ShieldRP18, 2.1×50 mm, 5 µm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Method C:

An Agilent 1200 LCMS system with ELS detector was used. Phenomenex Luna-C18, 5 µm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method D:

An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=85:15 to 0:100 in 3.4 minutes and with a flow rate of 0.8 mL/min.

Method E:

An Agilent 1200 LCMS system with ELS detector was used. Waters Xbridge-C18, 50×2 mm; Column temperature: 50° C.; Solvent system: A=water/trifluoroacetic acid (99.96:0.04) and B=acetonitrile/trifluoroacetic acid (99.98:0.02); Method: Linear gradient elution with A:B=90:10 to 0:100 in 3.4 minutes and with a flow rate of 0.8 mL/min.

Method F:

An Agilent 1200 LCMS system with ELS detector was used. Waters Xbridge-C18, 50×2 mm; Column temperature: 50° C.; Solvent system: A=water/trifluoroacetic acid (99.96:0.04) and B=acetonitrile/trifluoroacetic acid (99.98:0.02); Method: Linear gradient elution with A:B=99:1 to 0:100 in 3.4 minutes and with a flow rate of 0.8 mL/min.

PREPARATION OF INTERMEDIATES

Intermediate: ethyl 2-cyano-3-methoxy-4-methylpent-2-enoate

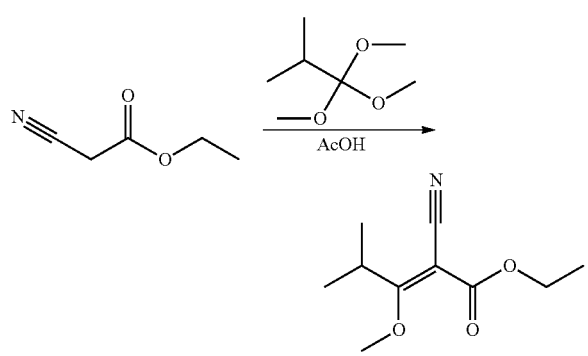

Ethyl 2-cyanoacetate (12.8 g, 113 mmol, 12.1 mL), 1,1,1-trimethoxy-2-methyl-propane (25.2 g, 170 mmol) and acetic acid (0.5 mL) were stirred at 120° C. for 4 days under a nitrogen atmosphere. The mixture was concentrated. The crude mixture was purified by flash chromatography with petroleum ether:ethyl acetate=20:1 to give ethyl 2-cyano-3-methoxy-4-methylpent-2-enoate (17.7 g).

Intermediate: ethyl 5-amino-3-isopropyl-1-methyl-1H-pyrazole-4-carboxylate

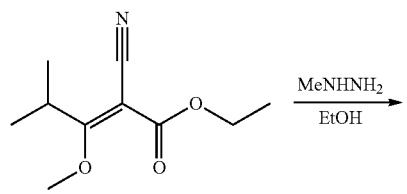

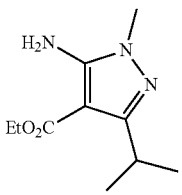

Methyl hydrazine (20.5 g, 178 mmol, 40 w %) was added dropwise to a solution of ethyl 2-cyano-3-methoxy-4-methyl-pent-2-enoate (12.2 g, 62 mmol) in ethanol (130 mL) at 0° C. The reaction was stirred for 90 minutes at 0° C., warmed to 70° C. over 60 minutes and agitated at 70° C. for 12 hours. The mixture was concentrated. The crude mixture was purified by flash chromatography with petroleum ether: ethyl acetate=2:1 to give ethyl 5-amino-3-isopropyl-1-methyl-pyrazole-4-carboxylate (8.5 g).

Intermediate: ethyl 4,6-dihydroxy-3-isopropyl-1-methyl-pyrazolo[3,4-b]pyridine-5-carboxylate

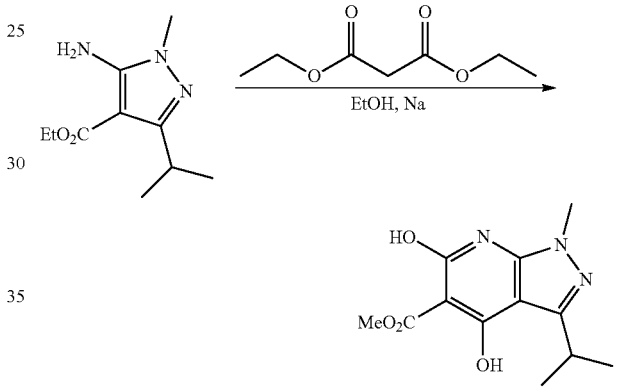

Under a nitrogen atmosphere, diethyl propanedioate (5.3 g, 33 mmol) was added to a solution of sodium ethoxide, freshly prepared from sodium (827 mg, 36 mmol) in ethanol (8 mL) at room temperature, and the mixture was stirred at room temperature for 0.5 hour. Ethyl 5-amino-3-isopropyl-1-methyl-pyrazole-4-carboxylate (2 g, 9 mmol) was added and the mixture was stirred at 100° C. for 12 hours. The mixture was concentrated and the residue was diluted with water (80 mL) and extracted with dichloromethane (30 mL×2). The aqueous layer was adjusted to pH=5 with aqueous 2N HCl. The resulting mixture was filtered and the filter cake was washed with water (15 mL×2), and dried to give ethyl 4,6-dihydroxy-3-isopropyl-1-methyl-pyrazolo[3,4-b]pyridine-5-carboxylate (2.2 g).

Intermediate: 3-isopropyl-1-methyl-1H-pyrazolo[3,4-b]pyridine-4,6-diol

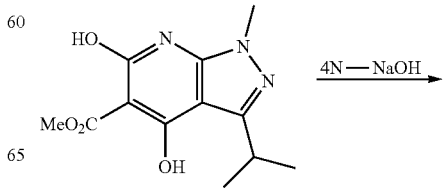

A mixture of ethyl 4,6-dihydroxy-3-isopropyl-1-methyl-pyrazolo[3,4-b]pyridine-5-carboxylate (1.7 g, 6.1 mmol) in aqueous 4N NaOH (17 mL) was stirred at 110° C. for 6 hours. The reaction mixture was cooled to 0° C. and aqueous saturated KHSO$_4$ was added to adjust the pH=1. The resulting mixture was filtered and the residue was washed with water (20 mL×2), The residue was dried under vacuum to give 3-isopropyl-1-methyl-pyrazolo[3,4-b]pyridine-4,6-diol (1.3 g).

$^1$H NMR (d$_6$-DMSO 400 MHz): δ 11.10 (brs, 2H), 5.43 (s, 1H), 3.71 (s, 3H), 3.25-3.18 (m, 1H), 1.24 (d, J=6.8 Hz, 6H).

Intermediate: 4,6-dichloro-3-isopropyl-1-methyl-1H-pyrazolo[3,4-b]pyridine

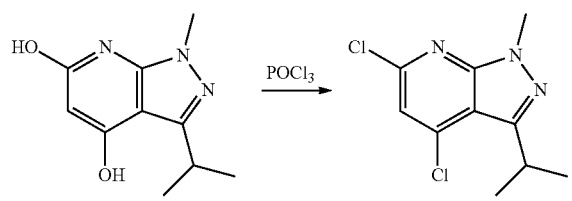

A mixture of 3-isopropyl-1-methyl-1H-pyrazolo[3,4-b]pyridine-4,6-diol (200 mg, 1 mmol) in POCl$_3$ (2 mL) was stirred at 80° C. for 18 hours. The mixture was concentrated and then water (10 mL) was added slowly, followed by addition of aqueous saturated NaHCO$_3$ to adjust pH=7. The aqueous layer was extracted with dichloromethane (50 mL×3), the combined organic layers were washed with brine (10 mL), dried over Na$_2$SO$_4$ and concentrated. The crude mixture was purified by flash chromatography with petroleum ether:ethyl acetate=30:1 to give 4,6-dichloro-3-isopropyl-1-methyl-1H-pyrazolo[3,4-b]pyridine (150 mg).

Intermediate: 6-chloro-3-isopropyl-N-(4-methoxy-benzyl)-1-methyl-1H-pyrazolo[3,4-b]pyridin-4-amine

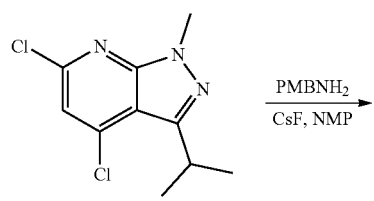

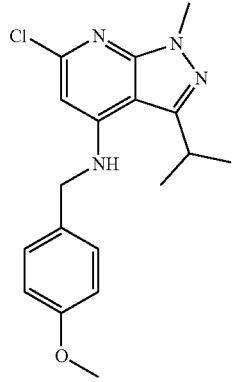

To a solution of 4,6-dichloro-3-isopropyl-1-methyl-pyrazolo[3,4-b]pyridine (300 mg, 1 mmol) in NMP (1 mL) was added CsF (373 mg, 2 mmol) and (4-methoxyphenyl)methanamine (202 mg, 1 mmol). The mixture was stirred at 100° C. for 18 hours. The reaction mixture was filtered and the residue was washed with ethyl acetate (15 mL×2), the combined filtrates were concentrated. The crude mixture of 6-chloro-3-isopropyl-N-[(4-methoxyphenyl)methyl]-1-methyl-pyrazolo[3,4-b]pyridin-4-amine (424 mg) was used into the next step without further purification.

Intermediate: 6-(2-ethoxypyridin-3-yl)-3-isopropyl-N-(4-methoxybenzyl)-1-methyl-1H-pyrazolo[3,4-b]pyridin-4-amine

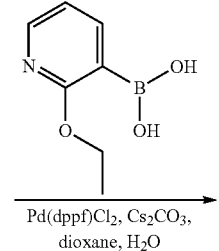

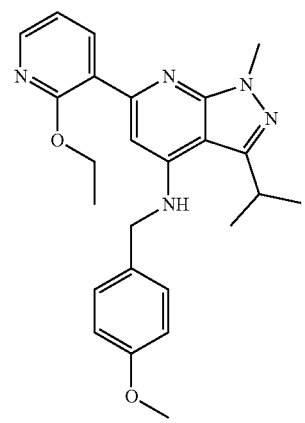

A mixture of 6-chloro-3-isopropyl-N-[(4-methoxyphenyl)methyl]-1-methyl-pyrazolo[3,4-b]pyridin-4-amine (424 mg, 1 mmol), (2-ethoxy-3-pyridyl)boronic acid (410 mg, 2 mmol), Pd(dppf)Cl₂ (225 mg, 0.3 mmol), Cs₂CO₃ (1 g, 3 mmol) in dioxane (3 mL) and water (1 mL) was degassed and purged with nitrogen 3 times, and then the mixture was stirred at 100° C. for 1 hour under microwave irradiation. Water (50 mL) was added and the mixture was extracted with ethyl acetate (60 mL×3). The combined organic layers were washed with brine (20 mL), dried over Na₂SO₄ and concentrated. The crude mixture was purified by flash chromatography with petroleum ether:ethyl acetate=3:1 to 2:1 to give 6-(2-ethoxy-3-pyridyl)-3-isopropyl-N-[(4-methoxyphenyl)methyl]-1-methyl-pyrazolo[3,4-b]pyridin-4-amine (500 mg).

Intermediate: 6-(2-ethoxypyridin-3-yl)-3-isopropyl-1-methyl-1H-pyrazolo[3,4-b]pyridin-4-amine

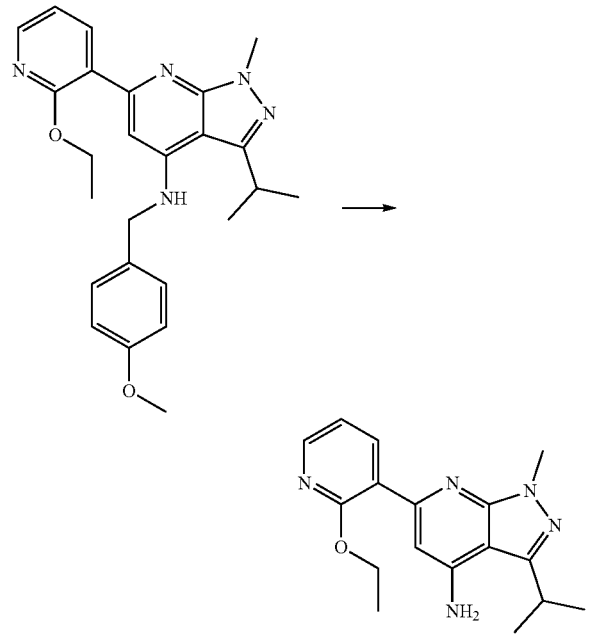

A mixture of 6-(2-ethoxy-3-pyridyl)-3-isopropyl-N-[(4-methoxyphenyl)methyl]-1-methyl-pyrazolo[3,4-b]pyridin-4-amine (500 mg, 1 mmol) in trifluoroacetic acid (5 mL) was stirred at 60° C. for 18 hours The mixture was concentrated and the residue was dissolved in ethyl acetate (200 mL). The resulting mixture was washed with aqueous saturated NaHCO₃ (70 mL), brine (20 mL), dried over Na₂SO₄ and concentrated. The crude mixture was purified by flash chromatography with petroleum ether:ethyl acetate=3:1 to 2:1 to give 6-(2-ethoxy-3-pyridyl)-3-isopropyl-1-methyl-pyrazolo[3,4-b]pyridin-4-amine (360 mg).

Intermediate: ethyl acetimidate hydrochloride

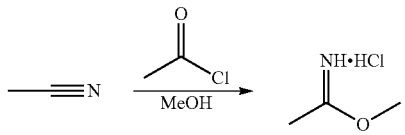

To a cooled (0° C.) solution of acetonitrile (10 g, 244 mmol) in dry methanol (15 mL) was added acetyl chloride (23.0 g, 292 mmol) dropwise. The mixture was stirred at 0° C. for 3 hours. The mixture was concentrated and methyl tert-butyl ether (50 mL) was added. The mixture was stirred at room temperature for 30 minutes. The mixture was filtered and the filter cake was washed with methyl tert-butyl ether (50 mL) and dried under vacuum to give ethyl acetimidate hydrochloride (13 g).

Intermediate: ethyl 4-methyl-2-nitro-3-oxopentanoate

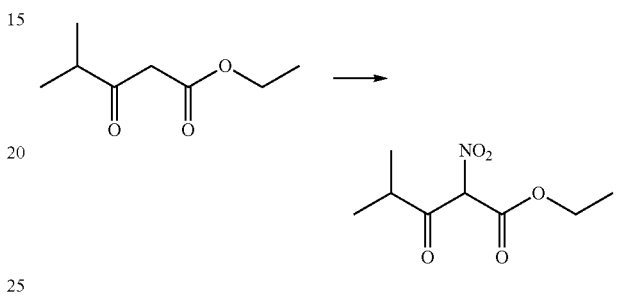

To a solution of ethyl 4-methyl-3-oxopentanoate (20 g, 126.4 mmol) in acetic acid (30 mL) was dropwise added a solution of NaNO₂ (12.2 g, 177 mmol) in water (30 mL). Then water (70 mL) was added. The mixture was stirred at room temperature for 16 hours. Ethyl acetate (300 mL) was added and the organic layer was washed with aqueous saturated NaHCO₃ (500 mL), water (200 mL), brine (200 mL) and dried over Na₂SO₄, filtered and concentrated to give ethyl 4-methyl-2-nitro-3-oxopentanoat (22.9 g).
¹H NMR (CDCl₃ 400 MHz): δ 4.41-4.35 (m, 3H), 3.45-3.36 (m, 1H), 1.37-1.34 (m, 3H), 1.16-1.14 (m, 6H).

Intermediate: ethyl 2-amino-4-methyl-3-oxopentanoate hydrochloride

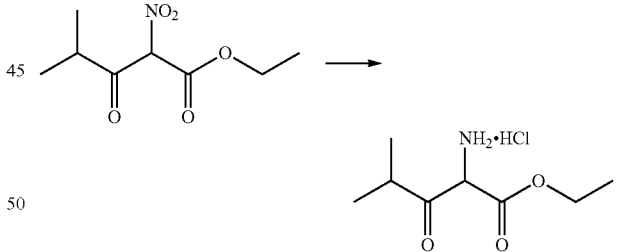

To a cooled (0° C.) solution of ethyl 4-methyl-2-nitro-3-oxopentanoate (22.9 g, 113 mmol) in dry methanol (150 mL) was added acetyl chloride (17.7 g, 226 mmol) dropwise. The mixture was stirred at 0° C. for 1 hour. Then Pd/C (4 g, 5.9 mmol) (10% Pd with 50% of water) was added under nitrogen. The suspension was degassed under vacuum and purged with H₂ several times. The mixture was stirred under H₂ (50 psi) at room temperature for 16 hours. The mixture was filtered through celite and the filtrate was concentrated to give ethyl 2-amino-4-methyl-3-oxopentanoate hydrochloride (20 g).
¹H NMR (d₆-DMSO 400 MHz): δ 8.93 (brs, 3H), 5.46 (s, 1H), 4.30-4.24 (m, 2H), 3.17-3.10 (m, 1H), 1.25 (t, J=7.2 Hz, 3H), 1.13 (d, J=7.2 Hz, 3H), 1.03 (d, J=6.4 Hz, 3H).

Intermediate: ethyl 4-isopropyl-2-methyl-1H-imidazole-5-carboxylate

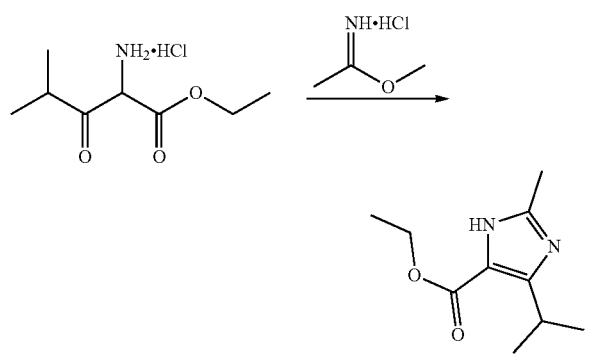

To a cooled (0° C.) solution of ethyl acetimidate hydrochloride (11.29 g, 103.0 mmol) in ethanol (50 mL) was dropwise added triethylamine (13.03 g, 128.8 mmol). Then a solution of ethyl 2-amino-4-methyl-3-oxopentanoate hydrochloride (5.40 g, 25.8 mmol) in ethanol (50 mL) was added at 0° C. and the mixture was stirred at room temperature for 16 hours. The mixture was concentrated. The residue was dissolved in ethyl acetate (20 mL) and washed with water (20 mL×2), brine (20 mL), dried over Na$_2$SO$_4$, filtered and concentrated to give ethyl 4-isopropyl-2-methyl-1H-imidazole-5-carboxylate (3.30 g).

$^1$H NMR (CDCl$_3$ 400 MHz): δ 4.33 (q, J=6.8 Hz, 2H), 3.63 (brs, 1H), 2.42 (s, 3H), 1.37 (t, J=7.2 Hz, 3H), 1.27 (d, J=7.2 Hz, 6H).

Intermediate: ethyl 1-amino-4-isopropyl-2-methyl-1H-imidazole-5-carboxylate

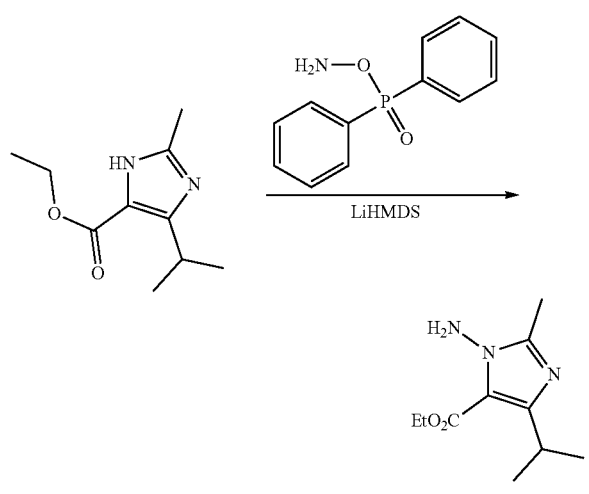

To a cooled (−10° C.) solution of ethyl 4-isopropyl-2-methyl-1H-imidazole-5-carboxylate (3.72 g, 19.0 mmol) in DMF (30 mL) was added a solution of LiHMDS (lithium hexamethyldisilazide) (1 M in THF, 20.86 mL). The mixture was stirred at −10° C. for 30 minutes. Then a solution of (aminooxy)diphenylphosphine oxide (5.31 g, 22.8 mmol) in DMF (20 mL) was added dropwise. The mixture was stirred at −10° C. for 1 hour. Water (50 mL) was added and the mixture was extracted with ethyl acetate (50 mL×2). The organic layer was washed with water (50 mL×3), brine (50 mL), dried over Na$_2$SO$_4$, filtered and concentrated to give ethyl 1-amino-4-isopropyl-2-methyl-1H-imidazole-5-carboxylate (3.07 g).

Intermediate: ethyl 4-isopropyl-1-(3-methoxy-3-oxopropanamido)-2-methyl-1H-imidazole-5-carboxylate

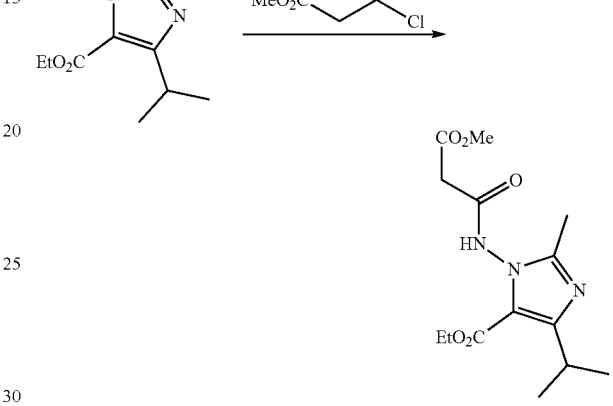

To a cooled (0° C.) solution of ethyl 1-amino-4-isopropyl-2-methyl-1H-imidazole-5-carboxylate (3.07 g, 14.5 mmol) in dichloromethane (30 mL) was added methyl 3-chloro-3-oxopropanoate (2.18 g, 16.0 mmol) dropwise. The mixture was stirred at 0° C. for 0.5 hour. Water (5 mL) was added. The mixture was concentrated. The residue was purified by flash chromatography on silica gel (10% to 100% ethyl acetate in petroleum ether) to give ethyl 4-isopropyl-1-(3-methoxy-3-oxopropanamido)-2-methyl-1H-imidazole-5-carboxylate (3.6 g).

$^1$H NMR (CDCl$_3$ 400 MHz): δ 11.95 (brs, 1H), 4.36 (q, J=7.2 Hz, 2H), 3.79 (s, 3H), 3.76-3.70 (m, 3H), 2.70 (s, 3H), 1.42-1.36 (m, 9H).

Intermediate: ethyl 2,4-dihydroxy-5-isopropyl-7-methylimidazo[1,5-b]pyridazine-3-carboxylate

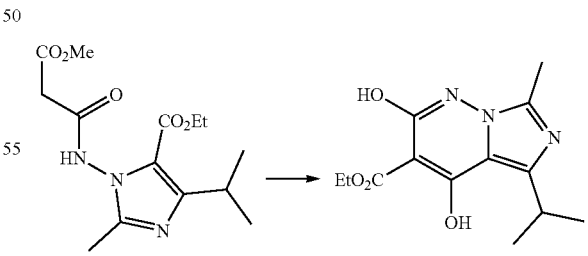

To a solution of ethyl 4-isopropyl-1-(3-methoxy-3-oxopropanamido)-2-methyl-1H-imidazole-5-carboxylate (2.91 g, 9.35 mmol) in THF (10 mL) was added t-BuOK (3.15 g, 28.0 mmol). The mixture was stirred at room temperature for 1 hour. Water (20 mL) was added and the mixture was acidified to pH=2 by aqueous 1N HCl. The mixture was extracted with ethyl acetate (50 mL×2). The combined organic layers were washed with water (50 mL), brine (50 mL), dried over Na$_2$SO$_4$, filtered and concentrated to give ethyl 2,4-dihydroxy-5-isopropyl-7-methylimidazo[1,5-b]pyridazine-3-carboxylate (2.40 g)

Intermediate: 5-isopropyl-7-methylimidazo[1,5-b]pyridazine-2,4-diol

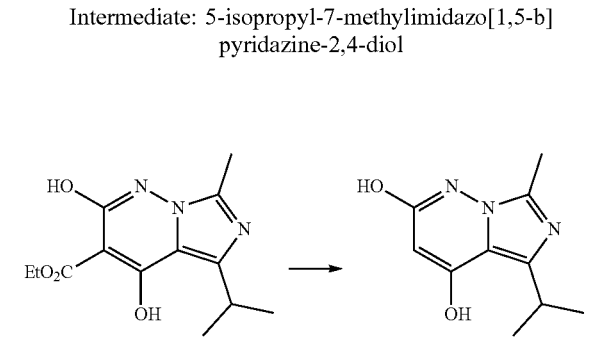

A solution of ethyl 2,4-dihydroxy-5-isopropyl-7-methylimidazo[1,5-b]pyridazine-3-carboxylate (1.90 g, 7.16 mmol) in aqueous NaOH (4N, 20 mL) was heated at 100° C. for 3 hours. The mixture was cooled to room temperature and acidified to pH=3 with a aqueous saturated KHSO$_4$ solution. The mixture was filtered and the filter cake was washed with water (100 mL) and dried under vacuum to give 5-isopropyl-7-methylimidazo[1,5-b]pyridazine-2,4-diol (800 mg).

$^1$H NMR (d$_6$-DMSO 400 MHz): δ 5.52 (s, 1H), 3.60-3.50 (m, 1H), 2.48 (s, 3H), 1.23 (d, J=7.2 Hz, 6H).

Intermediate: 2,4-dichloro-5-isopropyl-7-methylimidazo[1,5-b]pyridazine

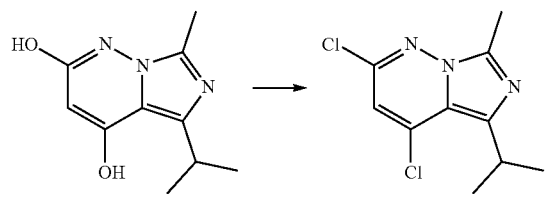

To a solution of 5-isopropyl-7-methylimidazo[1,5-b]pyridazine-2,4-diol (500 mg, 2.41 mmol) in dry toluene (5 mL) was added diisopropylethylamine (623 mg, 4.82 mmol) and POCl$_3$ (1.48 g, 9.64 mmol). The mixture was heated at 120° C. in a sealed tube for 16 hours. The mixture was cooled to room temperature and water (5 mL) was added. The mixture was adjusted to pH=7 by addition of aqueous saturated NaHCO$_3$ solution and extracted with ethyl acetate (20 mL). The organic layer was washed with water (20 mL), brine (20 mL), dried over Na$_2$SO$_4$, filtered and concentrated. The residue was purified by flash chromatography on silica gel (10% to 20% ethyl acetate in petroleum ether) to give 2,4-dichloro-5-isopropyl-7-methylimidazo[1,5-b]pyridazine (400 mg).

Intermediate: 2,4-dibromo-5-isopropyl-7-methylimidazo[1,5-b]pyridazine

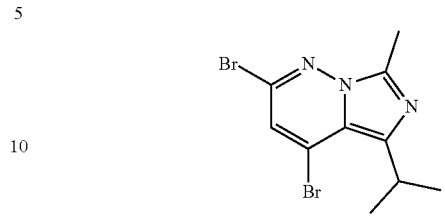

2,4-Dibromo-5-isopropyl-7-methylimidazo[1,5-b]pyridazine was prepared in a similar way from 5-isopropyl-7-methylimidazo[1,5-b]pyridazine-2,4-diol and POBr$_3$.

Intermediate: 2-chloro-5-isopropyl-N-(4-methoxybenzyl)-7-methylimidazo[1,5-b]pyridazin-4-amine

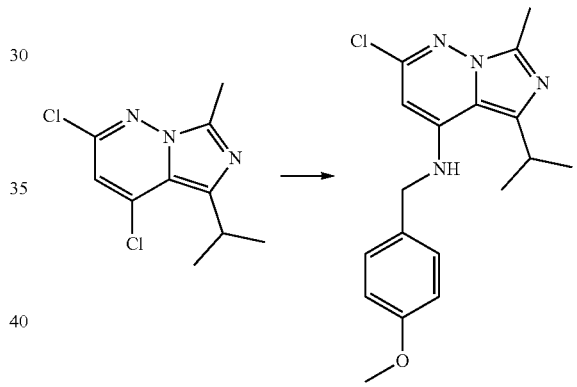

To a solution of 2,4-dichloro-5-isopropyl-7-methylimidazo[1,5-b]pyridazine (250 mg, 1.02 mmol) in NMP (5 mL) was added p-methoxybenzylamine (168 mg, 1.22 mmol) and CsF (310 mg, 2.04 mmol). The mixture was heated at 100° C. for 16 hours. The mixture was cooled to room temperature and water (5 mL) was added. The mixture was extracted with ethyl acetate (20 mL×2). The organic layer was washed with water (20 mL×3), brine (20 mL), dried over Na$_2$SO$_4$, filtered and concentrated. The residue was purified by flash chromatography on silica gel (10% to 50% ethyl acetate in petroleum ether) to give 2-chloro-5-isopropyl-N-(4-methoxybenzyl)-7-methylimidazo[1,5-b]pyridazin-4-amine (250 mg).

$^1$H NMR (CDCl$_3$ 400 MHz): δ 7.28 (d, J=8.4 Hz, 2H), 6.94 (d, J=8.4 Hz, 2H), 5.23 (s, 1H), 5.30-5.28 (m, 1H), 4.40 (d, J=4.2 Hz, 2H), 3.84 (s, 3H), 3.13-3.06 (m, 1H), 2.63 (s, 3H), 1.37 (d, J=6.8 Hz, 6H).

Intermediate: 2-(2-ethoxypyridin-3-yl)-5-isopropyl-N-(4-methoxybenzyl)-7-methylimidazo[1,5-b]pyridazin-4-amine

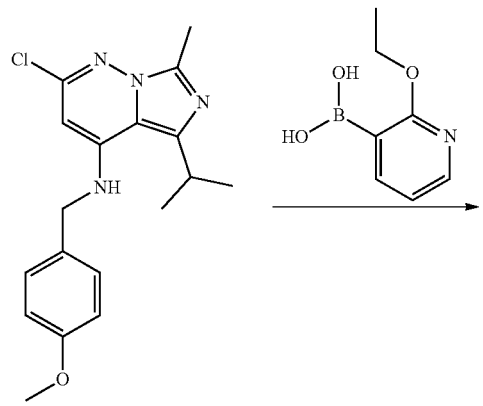

To a solution of 2-chloro-5-isopropyl-N-[(4-methoxyphenyl)methyl]-7-methyl-imidazo[1,5-b]pyridazin-4-amine (250 mg, 0.72 mmol) in dioxane (4 mL) and water (2 mL) was added (2-ethoxypyridin-3-yl)boronic acid (182 mg, 1.09 mmol), $Cs_2CO_3$ (472 mg, 1.45 mmol) and Pd(dppf)$Cl_2$ (53 mg, 0.07 mmol). The mixture was degassed with nitrogen and heated under microwave irradiation at 100° C. for 1 hour. The mixture was cooled to room temperature and extracted with ethyl acetate (20 mL×2). The combined organic layers were washed with water (20 mL), brine (20 mL), dried over $Na_2SO_4$, filtered and concentrated to give the crude product. The residue was purified by flash chromatography on silica gel (10% to 50% ethyl acetate in petroleum ether) to give 2-(2-ethoxypyridin-3-yl)-5-isopropyl-N-(4-methoxybenzyl)-7-methylimidazo[1,5-b]pyridazin-4-amine (290 mg).

Intermediate: benzyl (cyanomethyl)carbamate

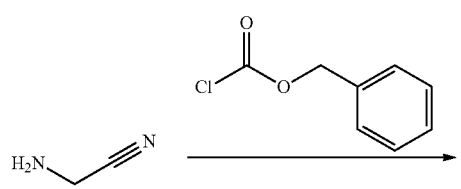

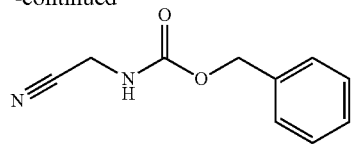

To a solution of NaOH (11 g, 0.26 mol) in water (170 mL) was added 2-aminoacetonitrile hydrochloride (24 g, 0.26 mol) in portions over 30 min. The mixture was stirred for 30 minutes at which time dioxane (20 mL) was added and the mixture cooled to 0° C. Benzyl carbonochloridate (23 g, 132 mmol) was added dropwise via an additional funnel over 1 hour. The cooling bath was removed and the mixture stirred for 12 hours at room temperature. To the mixture was added aqueous HCl (6N) until pH=3, the aqueous layer extracted with dichloromethane (100 mL×3). The combined organic layers were washed with brine (100 mL), dried over anhydrous $Na_2SO_4$, filtered and concentrated in vacuum. The residue was purified by silica gel chromatography (ethyl acetate/petroleum ether) to afford (19 g).

Intermediate: benzyl ((2H-tetrazol-5-yl)methyl)carbamate

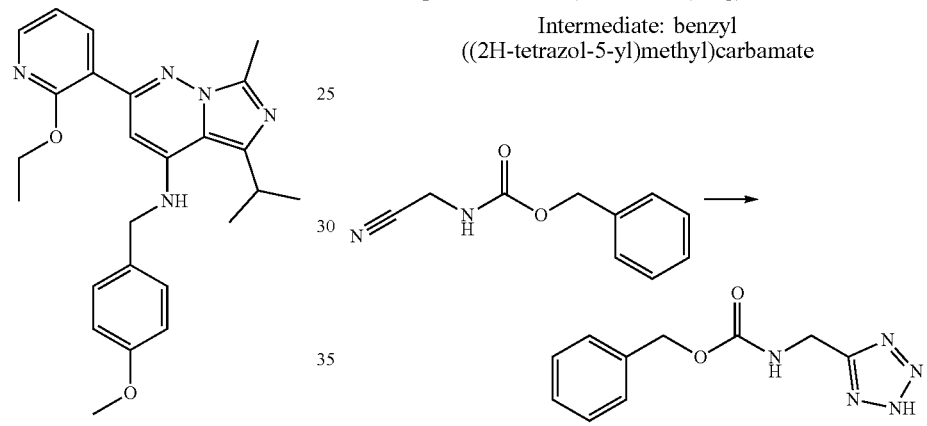

A mixture of benzyl (cyanomethyl)carbamate (5.0 g, 26 mmol), $NaN_3$ (3.4 g, 53 mmol), $ZnBr_2$ (3.3 g, 15 mmol) and isopropyl alcohol (30 mL) in water (60 mL) was stirred at 100° C. for 12 hours. The mixture was poured into water (250 mL), and aqueous $KHSO_4$ was added until pH=2. The aqueous phase was extracted with ethyl acetate (100 mL×3). The combined organic phase were washed with brine (80 mL), dried over anhydrous $Na_2SO_4$, filtered and concentrated in vacuum to afford benzyl ((2H-tetrazol-5-yl)methyl)carbamate (6.0 g).

Intermediate: benzyl ((2-methyl-2H-tetrazol-5-yl)methyl)carbamate

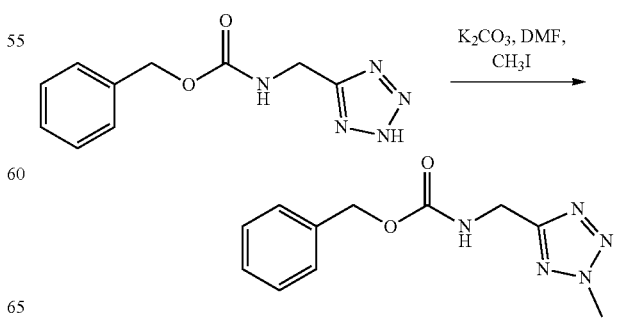

To a mixture of benzyl ((2H-tetrazol-5-yl)methyl)carbamate (2.0 g, 8.6 mmol) and K₂CO₃ (2.4 g, 17 mmol) in DMF (20 mL) was added methyl iodide (1.8 g, 13 mmol) at 0° C., and it was stirred at 30° C. for 12 hours. The mixture was filtered and the filtrate was concentrated under vacuum. The residue was purified by silica gel chromatography (petroleum ether/ethyl acetate=10/1 to 1/1) to afford benzyl ((2-methyl-2H-tetrazol-5-yl)methyl)carbamate (560 mg).

Intermediate:
(2-methyl-2H-tetrazol-5-yl)methanamine

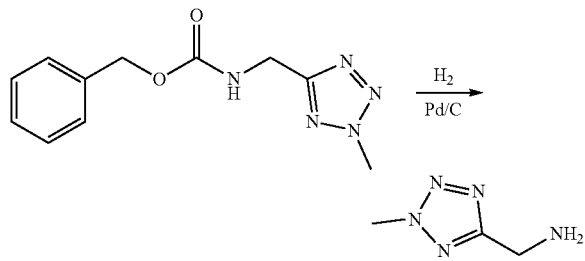

To a solution of benzyl ((2-methyl-2H-tetrazol-5-yl)methyl)carbamate (560 mg, 2.3 mmol) in methanol (10 mL) was added Pd/C (wet, 5 mg, 10% Pd/C) under N₂. The suspension was degassed under vacuum and purged with H₂ several times. The mixture was stirred under H₂ (15 psi) at room temperature for 12 hours. The mixture was filtered and the filtrate was concentrated under vacuum to afford (2-methyl-2H-tetrazol-5-yl)methanamine (200 mg).

Intermediate:
(2-methyl-2H-1,2,3-triazol-4-yl)methanol

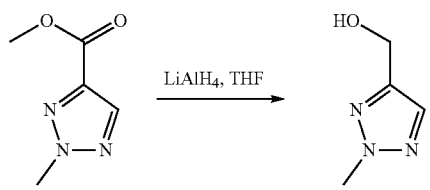

A solution of methyl 2-methyl-2H-1,2,3-triazole-4-carboxylate (400 mg, 2.83 mmol) in THF (4 mL) was added to a mixture of LiAlH₄ (323 mg, 8.50 mmol) in THF (10 mL) at 0° C. The resulting mixture was stirred at 0° C. for 2 hours. The solution was quenched with NaOH (aq. 1N, 3 mL) at 0° C. The mixture was filtered and concentrated under vacuum to afford (2-methyl-2H-1,2,3-triazol-4-yl)methanol.

Intermediate:
4-(bromomethyl)-2-methyl-2H-1,2,3-triazole

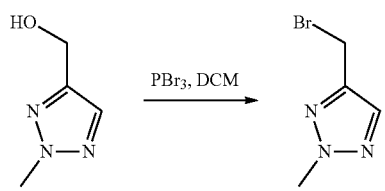

To a solution of (2-methyl-2H-1,2,3-triazol-4-yl)methanol (280 mg, 2.48 mmol) in dichloromethane (30 mL) was added PBr₃ (1.3 g, 4.95 mmol) at 0° C. The resulting mixture was stirred at 30° C. for 12 hours. The solution was poured into ice-water (10 mL), the aqueous phase was extracted with ethyl acetate (10 mL×3). The combined organic phases were washed with brine (10 mL×1), dried with anhydrous Na₂SO₄, filtered and concentrated under vacuum. The residue was purified by silica gel chromatography (petroleum ether/ethyl acetate=1/0, 2/1) to afford 4-(bromomethyl)-2-methyl-2H-1,2,3-triazole.

Intermediate:
4-(chloromethyl)-1-methyl-1H-1,2,3-triazole

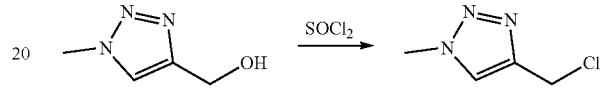

A solution of (1-methyl-1H-1,2,3-triazol-4-yl)methanol (0.1 g, 0.88 mmol) in SOCl₂ (10 mL) was stirred at 80° C. for 1 hour. The solution was concentrated under vacuum. The residue was diluted with dichloromethane (10 mL) and washed with NaHCO₃ (aq.) until pH=7. The organic phase was washed with brine (5 mL×1), dried with anhydrous Na₂SO₄, filtered and concentrated in vacuum to afford 4-(chloromethyl)-1-methyl-1H-1,2,3-triazole.

Intermediate: tert-butyl
((3-methyl-1,2,4-oxadiazol-5-yl)methyl)carbamate

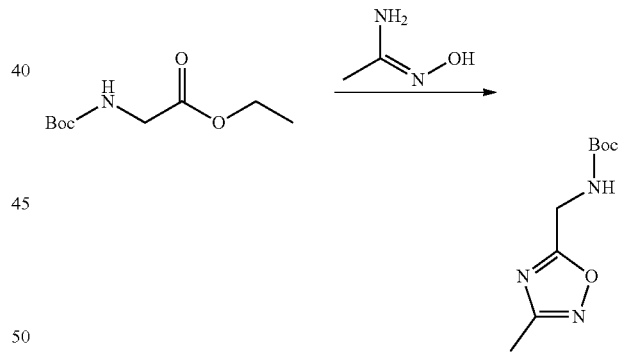

Molecular sieve 4 Å (500 mg) was added to a solution of N-hydroxyacetamidine (1.09 g, 14.76 mmol) in THF (20 mL). The mixture was stirred at 20° C. for 30 minutes. Then NaH (590 mg, 14.8 mmol, 60% in mineral oil) was added and the mixture was heated at 50° C. for 30 minutes. Then the mixture was cooled to 20° C. and ethyl 2-((tert-butoxycarbonyl)amino)acetate (1 g, 4.92 mmol) was added. The mixture was heated at 80° C. for 2 hours. Water (5 mL) was added. The mixture was extracted with ethyl acetate (20 mL×2). The combined organic phases were washed with H₂O (20 mL), brine (20 mL), dried over Na₂SO₄, filtered and concentrated. The residue was purified by flash chromatography on silica gel (0%~50% ethyl acetate in petroleum ether) to give tert-butyl ((3-methyl-1,2,4-oxadiazol-5-yl)methyl)carbamate.

Intermediate: (3-methyl-1,2,4-oxadiazol-5-yl)methanamine hydrochloride

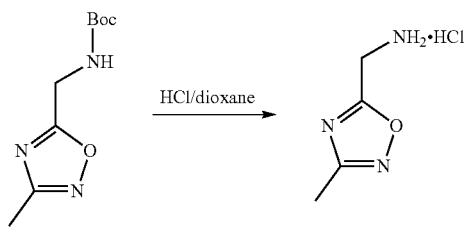

To a solution of tert-butyl ((3-methyl-1,2,4-oxadiazol-5-yl)methyl)carbamate (400 mg, 1.88 mmol) in dichloromethane (4 mL) was added HCl/dioxane (4 M, 4 mL). The mixture was stirred at 20° C. for 1 h. The mixture was concentrated to give (3-methyl-1,2,4-oxadiazol-5-yl)methanamine hydrochloride.

Intermediate: 1-methyl-1H-1,2,4-triazole-3-carbaldehyde

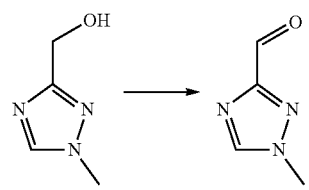

To a mixture of (1-methyl-1H-1,2,4-triazol-3-yl)methanol (400 mg, 3.54 mmol) and iodobenzene diacetate (1.25 g, 3.89 mmol) in dichloromethane (10 mL) was added TEMPO ((2,2,6,6-tetramethylpiperidin-1-yl)oxyl) (56 mg, 354 mol). The mixture was stirred at 15-20° C. for 2 h. The mixture was concentrated in vacuo. The residue was purified by silica gel chromatography (petroleum ether:ethyl acetate=1:2) to give 1-methyl-1H-1,2,4-triazole-3-carbaldehyde.

Intermediate: 2-propoxy-3-(4,4,5,5-tetramethyl-1,3,2-dioxaborolan-2-yl)pyridine

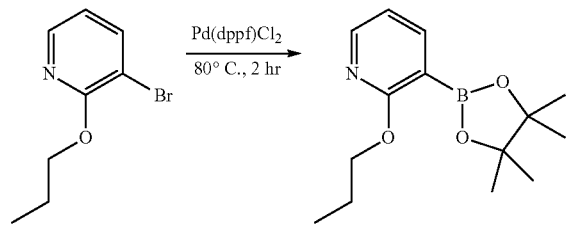 [SMILES: CCCOc1ncccc1Br ; CCCOc1ncccc1B1OC(C)(C)C(C)(C)O1]

A mixture of 3-bromo-2-propoxy-pyridine (200 mg, 0.093 mmol), 4,4,5,5-tetramethyl-2-(4,4,5,5-tetramethyl-1,3,2-dioxaborolan-2-yl)-1,3,2-dioxaborolane (282 mg, 1.11 mmol), KOAc (182 mg, 1.85 mmol), Pd(dppf)Cl$_2$ (135 mg, 0.18 mmol) in dioxane (3 mL) was degassed and purged with N$_2$ for 3 times, and then the mixture was stirred at 80° C. for 2 hours under a N$_2$ atmosphere. The mixture was filtered and the residue was washed with dioxane (5 mL×2), the combined filtrates were concentrated. The crude product 2-propoxy-3-(4,4,5,5-tetramethyl-1,3,2-dioxaborolan-2-yl)pyridine was used into the next step without further purification.

Intermediate: 4-(chloromethyl)-2-methoxypyridine

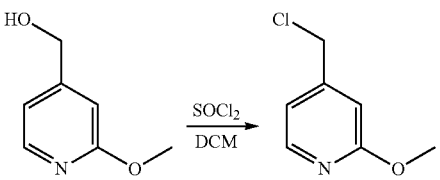

To a solution of (2-methoxypyridin-4-yl)methanol (200 mg, 1.44 mmol) in dichloromethane (5 mL) was added SOCl$_2$ (513 mg, 4.31 mmol) at 0° C. The mixture was stirred at 20° C. for 2 hours. The mixture was concentrated. The residue was dissolved in ethyl acetate (20 mL) and H$_2$O (20 mL). The organic layer was washed with sat. aq. NaHCO$_3$ (20 mL), H$_2$O (20 mL), brine (20 mL), dried over Na$_2$SO$_4$, filtered and concentrated to give 4-(chloromethyl)-2-methoxypyridine.

Intermediate: diethyl 2-((tert-butoxycarbonyl)amino)malonate

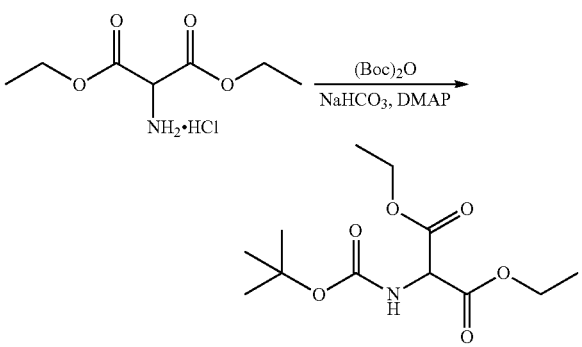

To a solution of diethyl 2-aminomalonate hydrochloride (50 g, 236 mmol) in H$_2$O (300 mL) and dioxane (440 mL) was slowly added NaHCO$_3$ (21 g, 248 mmol) at 20° C. When the solution became clear, DMAP (289 mg, 2 mmol) was added followed by dropwise addition of a solution of Boc$_2$O (54 g, 248 mmol) in dioxane (160 mL). The mixture was stirred at 20° C. for 12 hours. The mixture were concentrated. The residue was dissolved in ethyl acetate. The organic phase was washed with solution of 5% KHSO$_4$ (aq.), sat. aq. NaHCO$_3$, water, and brine, and dried over anhydrous Na$_2$SO$_4$, then filtered and concentrated to give diethyl 2-((tert-butoxycarbonyl)amino)malonate.

Intermediate: 2-((tert-butoxycarbonyl)amino)-3-ethoxy-3-oxopropanoic acid

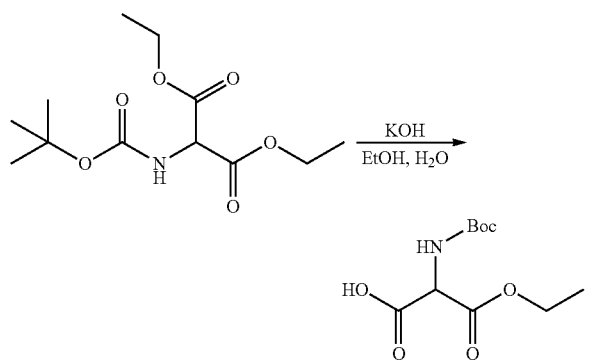

To a solution of diethyl 2-((tert-butoxycarbonyl)amino) malonate (30 g, 109 mmol) in EtOH/H$_2$O (675 mL/75 mL), a solution of KOH (7 g, 120 mmol) in H$_2$O (45 mL) was added dropwise while stirring at 20° C. The reaction mixture was stirred at 20° C. for 12 hours. The ethanol was removed in vacuo and the residue was acidified to pH=2 by 2N HCl (aq.) and washed with dichloromethane. The organic layer was washed with brine and dried over Na$_2$SO$_4$, filtered and concentrated to give 2-((tert-butoxycarbonyl)amino)-3-ethoxy-3-oxopropanoic acid.

Intermediate: ethyl 2-((tert-butoxycarbonyl)amino)-4-methyl-3-oxohexanoate

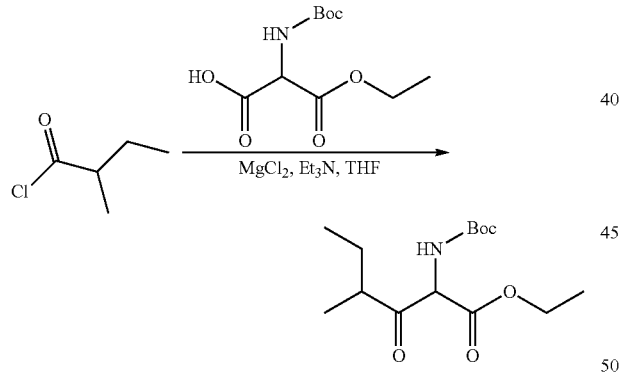

A mixture of 2-((tert-butoxycarbonyl)amino)-3-ethoxy-3-oxopropanoic acid (41 g, 166 mmol), triethylamine (34 g, 340 mmol) and MgCl$_2$ (17 g, 174 mmol) in MeCN (320 mL) was stirred at 0° C. for 2.5 hours. Then a solution of (±)-2-methylbutanoyl chloride (10 g, 83 mmol) in MeCN (80 mL) was added to the resulting mixture at 0° C. The mixture was stirred at 20° C. for 12 hours. The reaction mixture was quenched by addition citric acid (sat. aq.) (50 mL) at 0° C., and extracted with ethyl acetate (10 mL×3). The combined organic layers were washed with citric acid (sat. aq. 50 mL), NaHCO$_3$ (sat. aq. 50 mL×2), and brine (100 mL), dried over Na$_2$SO$_4$ filtered and concentrated under reduced pressure. The residue was purified by flash silica gel chromatography (0%~10% ethyl acetate in petroleum ether) to give ethyl 2-((tert-butoxycarbonyl)amino)-4-methyl-3-oxohexanoate.

Intermediate: ethyl 2-amino-4-methyl-3-oxohexanoate hydrochloride

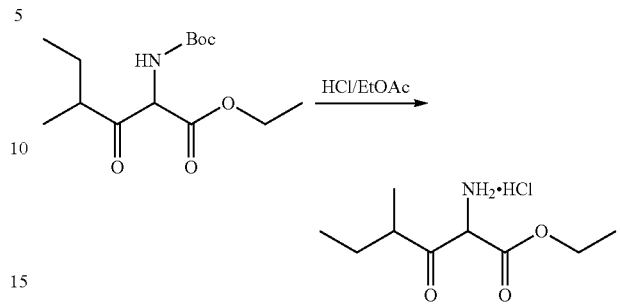

A solution of ethyl 2-((tert-butoxycarbonyl)amino)-4-methyl-3-oxohexanoate (16 g, 56 mmol) in HCl/ethyl acetate (4 M, 160 mL) was stirred at 20° C. for 12 hours. The solution was concentrated to give ethyl 2-amino-4-methyl-3-oxohexanoate hydrochloride.

Intermediates: (+)-5-(sec-butyl)-2-(2-ethoxypyridin-3-yl)-N-(4-methoxybenzyl)-7-methylimidazo[1,5-b]pyridazin-4-amine and (−)-5-(sec-butyl)-2-(2-ethoxypyridin-3-yl)-N-(4-methoxybenzyl)-7-methylimidazo[1,5-b]pyridazin-4-amine

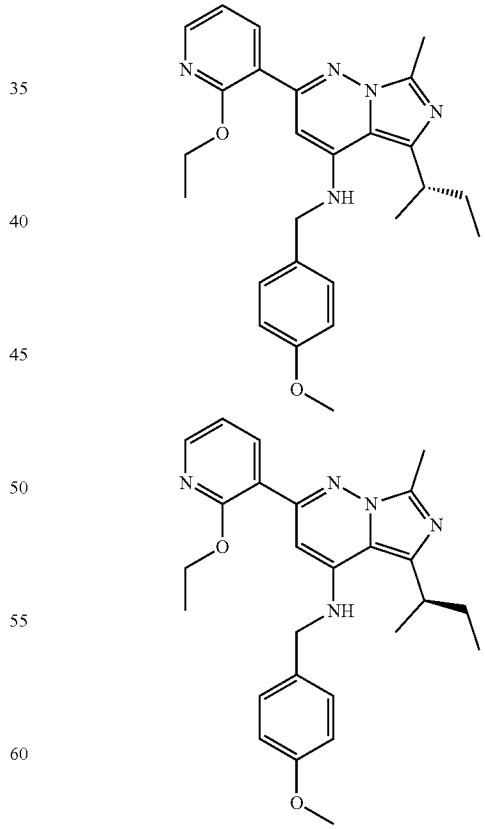

(±)-5-(sec-butyl)-2-(2-ethoxypyridin-3-yl)-N-(4-methoxybenzyl)-7-methylimidazo[1,5-b]pyridazin-4-amine was prepared in a similar way as 2-(2-ethoxypyridin-3-yl)-

5-isopropyl-N-(4-methoxybenzyl)-7-methylimidazo[1,5-b] pyridazin-4-amine from (±)-ethyl 2-amino-4-methyl-3-oxo-hexanoate hydrochloride. (+)-5-(sec-Butyl)-2-(2-ethoxypyridin-3-yl)-N-(4-methoxybenzyl)-7-methylimidazo[1,5-b]pyridazin-4-amine (SFC: $t_R$=3.850 minutes, ee %=99.2%; $[\alpha]_D^{20}$+2.67 (c=0.2, MeOH)) and (−)-5-(sec-butyl)-2-(2-ethoxypyridin-3-yl)-N-(4-methoxy-benzyl)-7-methylimidazo[1,5-b]pyridazin-4-amine (SFC: $t_R$=4.177 minutes, ee %=98.3%; $[\alpha]_D^{20}$−11.0 (c=0.2, MeOH)) were obtained after chiral SFC separation (SFC conditions: Instrument: Waters wpc2; Column: Chiralpak AD-3 150×4.6 mm I.D., 3 um; Mobile phase: A: $CO_2$B: iso-propanol (0.05% DEA); Gradient: from 5% to 40% of B in 5 min and hold 40% for 2.5 min, then 5% of B for 2.5 min; Flow rate: 2.5 mL/min; Column temp.: 35° C.; Nozzle Pressure: 100 Bar; Nozzle Temp: 60° C.; Evaporator Temp: 20° C.; Trimmer Temp: 25° C.; Wavelength: 220 nm).

Intermediate: 3-isopropyl-N-(4-methoxybenzyl)-1-methyl-6-(2-propoxypyridin-3-yl)-1H-pyrazolo[3,4-b]pyridin-4-amine

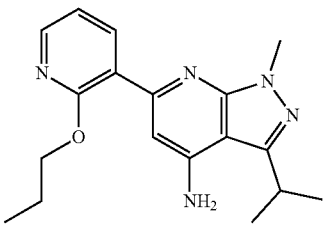 [SMILES: CCCOc1ncccc1-c1cc(N)c2c(C(C)C)nn(C)c2n1]

3-isopropyl-N-(4-methoxybenzyl)-1-methyl-6-(2-propoxypyridin-3-yl)-1H-pyrazolo[3,4-b]pyridin-4-amine was prepared in a similar way as 2-(2-ethoxypyridin-3-yl)-5-isopropyl-N-(4-methoxybenzyl)-7-methylimidazo[1,5-b] pyridazin-4-amine from 4,6-dichloro-3-isopropyl-1-methyl-pyrazolo[3,4-b]pyridine and 2-propoxy-3-(4,4,5,5-tetramethyl-1,3,2-dioxaborolan-2-yl)pyridine.

Intermediate: 5-iodoimidazo[1,5-a]pyridine

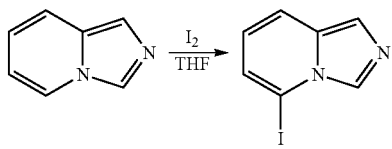

A mixture of imidazo[1,5-a]pyridine (2 g, 17 mmol) in THF (150 mL) was cooled to −78° C. and n-butyllithium (2.5 M, 14 mL) was added dropwise. The reaction mixture was stirred for 30 minutes at −78° C., then the solution was warmed to 20° C. and stirred for 30 minutes. The solution was cooled to 0° C., quenched with $I_2$ (4.5 g, 18 mmol) in THF (5 mL) and stirred for 2 hours. The resulting mixture was diluted with water and extracted with dichloromethane (3×50 mL). The organic layers were dried over $Na_2SO_4$, filtered and concentrated. The residue was purified by flash silica gel chromatography (0%~100% ethyl acetate in petroleum ether) to give 5-iodoimidazo[1,5-a]pyridine.

Intermediate: imidazo[1,5-a]pyridine-5-carbonitrile

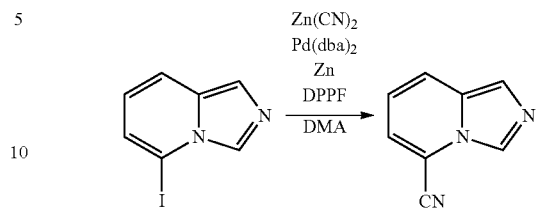

To a stirred solution of 5-iodoimidazo[1,5-a]pyridine (750 mg, 3.1 mmol) in dimethylacetamide (15 mL) under an argon atmosphere were added $Zn(CN)_2$ (235 mg, 2.0 mmol), $Pd(dba)_2$ (71 mg, 0.12 mmol), DPPF (136 mg, 0.25 mmol) at 25° C. The reaction mixture was stirred for 30 minutes at 100° C. (heating by microwaves). The reaction mixture was diluted with water (30 mL) and extracted with ethyl acetate (2×45 mL). The combined organic extracts were washed with water (40 mL), dried over $Na_2SO_4$, filtered and concentrated. The residue was purified by flash silica gel chromatography (0%~50% ethyl acetate in petroleum ether) to give imidazo[1,5-a]pyridine-5-carbonitrile.

Intermediate: tert-butyl (imidazo[1,5-a]pyridin-5-ylmethyl)carbamate

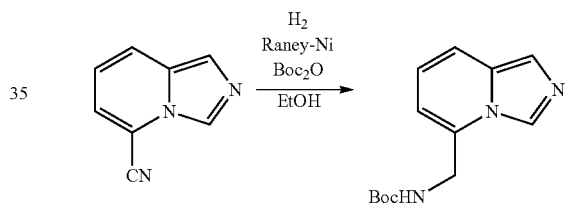

To a solution of Raney-Ni (1.5 g, 17 mmol) in EtOH (10 mL) was added imidazo[1,5-a]pyridine-5-carbonitrile (0.5 g, 3.5 mmol) and $Boc_2O$ (839 mg, 3.8 mmol), then the mixture was stirred at 25° C. under $H_2$ (45 Psi) for 4 hours. The mixture was filtered and concentrated. The residue was purified by flash silica gel chromatography (0%~100% ethyl acetate in petroleum ether) to give tert-butyl (imidazo[1,5-a]pyridin-5-ylmethyl)carbamate.

Intermediate: imidazo[1,5-a]pyridin-5-ylmethanamine

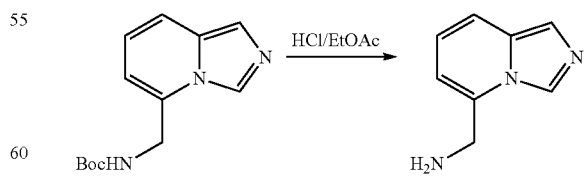

A mixture of tert-butyl (imidazo[1,5-a]pyridin-5-ylmethyl)carbamate (94 mg, 0.38 mmol) in HCl/ethyl acetate (2 mL) was stirred at 20° C. for 0.5 hour. The reaction mixture was concentrated to give imidazo[1,5-a]pyridin-5-ylmethanamine.

Intermediate: imidazo[1,2-a]pyridine-5-carbonitrile

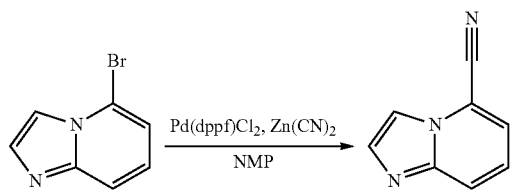 [SMILES: Brc1cccc2nccn12 ; N#Cc1cccc2nccn12]

A mixture of 5-bromoimidazo[1,2-a]pyridine (500 mg, 2.54 mmol), Zn(CN)$_2$ (328 mg, 2.79 mmol), and Pd(dppf)Cl$_2$ (186 mg, 0.254 mmol) in NMP (30 mL) was stirred at 140° C. for 2 hour under N$_2$. The mixture was poured into NaHCO$_3$ (aq. 100 mL) extracted with ethyl acetate (30 mL×3). The combined organic phases were washed with brine (50 mL×3), dried with anhydrous Na$_2$SO$_4$, filtered and concentrated. The residue was purified by column chromatography (silica gel, petroleum ether/ethyl acetate=1/0 to 1:1) to afford imidazo[1,2-a]pyridine-5-carbonitrile

Intermediate: tert-butyl (imidazo[1,2-a]pyridin-5-ylmethyl)carbamate

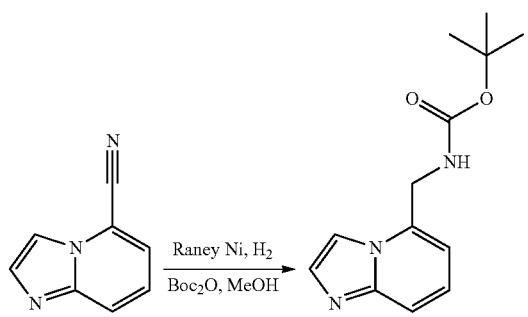 [SMILES: N#Cc1cccc2nccn12 ; CC(C)(C)OC(=O)NCc1cccc2nccn12]

To a solution of imidazo[1,2-a]pyridine-5-carbonitrile (200 mg, 1.40 mmol) and Boc$_2$O (366 mg, 1.68 mmol) in MeOH (30 mL) was added Raney-Ni (22 mg) at 30° C. The mixture was stirred at 30° C. for 12 hours under H$_2$ (45 Psi). The mixture was filtered and the filtrate was concentrated to afford tert-butyl (imidazo[1,2-a]pyridin-5-ylmethyl)carbamate.

Intermediate: imidazo[1,2-a]pyridin-5-ylmethanamine hydrochloride

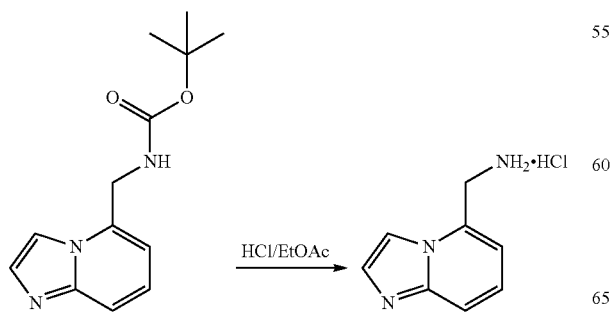

A mixture of tert-butyl (imidazo[1,2-a]pyridin-5-ylmethyl)carbamate (350 mg) in HCl/ethyl acetate (4M, 20 mL) was stirred at 10° C. for 1 hour. The mixture was concentrated to afford imidazo[1,2-a]pyridin-5-ylmethanamine hydrochloride, which was used into the next step without further purification.

PREPARATION OF COMPOUNDS OF THE INVENTION

Example 1: 6-(2-ethoxy-3-pyridyl)-3-isopropyl-1-methyl-N-[(1-methylimidazol-4-yl)methyl]pyrazolo[3,4-b]pyridin-4-amine

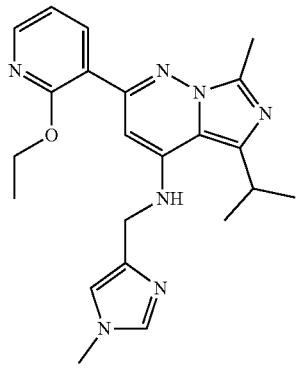 [SMILES: CCOc1ncccc1-c1cc(NCc2cn(C)cn2)c2c(C(C)C)nc(C)n2n1]

Preparation of 2-(2-ethoxypyridin-3-yl)-5-isopropyl-7-methylimidazo[1,5-b]pyridazin-4-amine

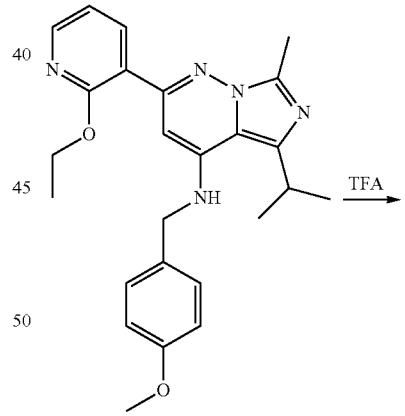

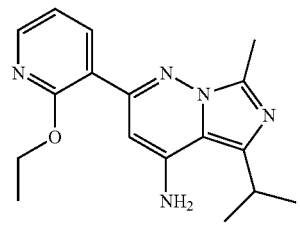

A solution of 2-(2-ethoxypyridin-3-yl)-5-isopropyl-N-(4-methoxybenzyl)-7-methylimidazo[1,5-b]pyridazin-4-amine (290 mg, 0.67 mmol) in trifluoroacetic acid (5 mL) was heated at 60° C. for 16 hours. The mixture was concentrated.

Water (10 mL) was added to the residue. The pH of the mixture was adjusted to pH=7 by addition of aqueous saturated NaHCO₃ solution. The mixture was extracted with ethyl acetate (20 mL×2). The combined organic layers were washed with water (20 mL) and brine (20 mL), dried over Na₂SO₄, filtered and concentrated. The residue was purified by flash chromatography on silica gel (10% to 50% ethyl acetate in petroleum ether) to give 2-(2-ethoxypyridin-3-yl)-5-isopropyl-7-methylimidazo[1,5-b]pyridazin-4-amine (150 mg).

Preparation of 2-(2-ethoxypyridin-3-yl)-5-isopropyl-7-methyl-N-((1-methyl-1H-imidazol-4-yl)methylene)imidazo[1,5-b]pyridazin-4-amine

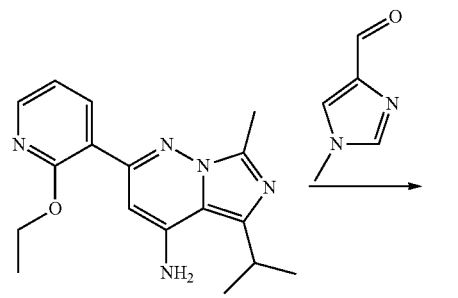

To a solution of 2-(2-ethoxypyridin-3-yl)-5-isopropyl-7-methylimidazo[1,5-b]pyridazin-4-amine (50 mg, 0.16 mmol) in dry THF (2 mL) was added 1-methyl-1H-imidazole-4-carbaldehyde (35 mg, 0.32 mmol) and Ti(i-PrO)₄ (91 mg, 0.32 mmol). The mixture was heated at 80° C. for 32 hours. The solution of 2-(2-ethoxypyridin-3-yl)-5-isopropyl-7-methyl-N-((1-methyl-1H-imidazol-4-yl)methylene)imidazo[1,5-b]pyridazin-4-amine (65 mg) in THF (2 mL) was directly used for the next step.

Preparation of 2-(2-ethoxypyridin-3-yl)-5-isopropyl-7-methyl-N-((1-methyl-1H-imidazol-4-yl)methyl)imidazo[1,5-b]pyridazin-4-amine

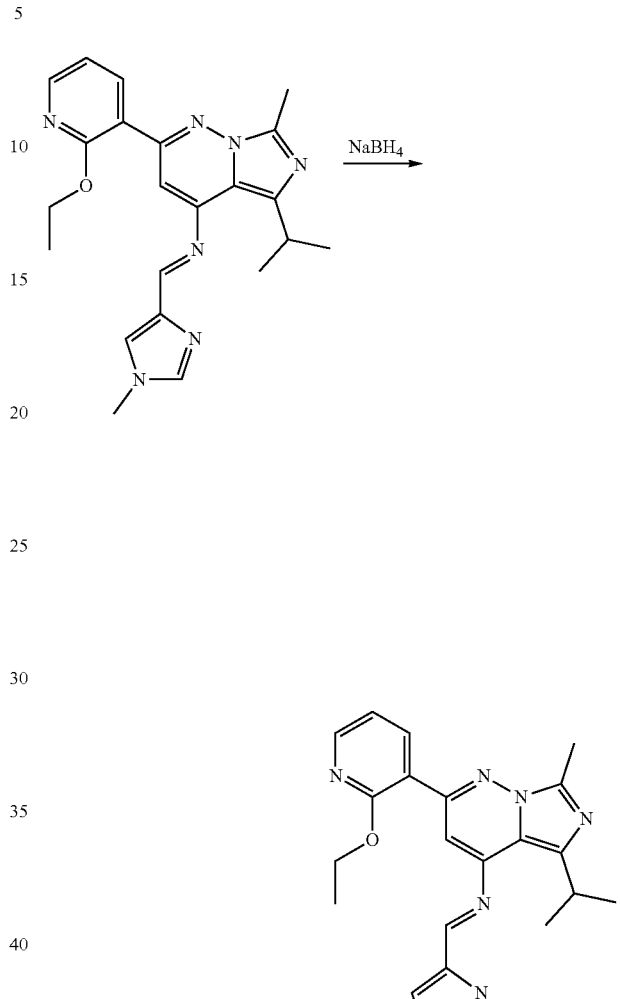

A reaction mixture from the previous step containing 2-(2-ethoxypyridin-3-yl)-5-isopropyl-7-methyl-N-((1-methyl-1H-imidazol-4-yl)methylene)imidazo[1,5-b]pyridazin-4-amine (65 mg, 0.16 mmol) in ethanol (2 mL) and THF (5 mL) was cooled to 0° C. and then NaBH₄ (30 mg, 0.80 mmol) was added in portions. The mixture was stirred at 0° C. for 1 hour. Water (5 mL) was added the mixture was filtered through celite, the filtrate was concentrated. The residue was purified by preparative HPLC to give 2-(2-ethoxypyridin-3-yl)-5-isopropyl-7-methyl-N-((1-methyl-1H-imidazol-4-yl)methyl)imidazo[1,5-b]pyridazin-4-amine (15 mg).

¹H NMR (CDCl₃ 400 MHz): δ 8.20 (dd, J=2.0, 4.8 Hz, 1H), 8.03 (dd, J=2.0, 7.6 Hz, 1H), 7.43 (s, 1H), 6.99 (dd, J=4.8, 7.2 Hz, 1H), 6.86 (s, 1H), 6.09 (s, 1H), 5.59 (brs, 1H), 4.48-4.41 (m, 4H), 3.68 (s, 3H), 3.33-3.26 (m, 1H), 2.68 (s, 3H), 1.42 (d, J=7.2 Hz, 6H), 1.38 (t, J=6.8 Hz, 3H). LC-MS: t_R=2.202 minutes (Method B), m/z=406.1 [M+H]+.

Example 2: 6-(2-ethoxy-3-pyridyl)-3-isopropyl-1-methyl-N-[(2-methyloxazol-4-yl)methyl]pyrazolo[3,4-b]pyridin-4-amine

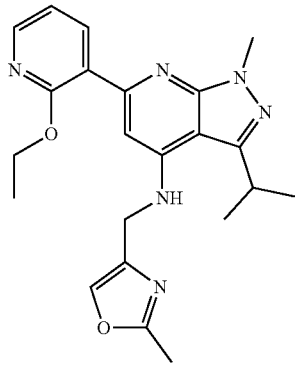 [SMILES: CCOc1ncccc1-c1cc(NCc2coc(C)n2)c2c(C(C)C)nn(C)c2n1]

Prepared in a way similar to example 1 from 6-(2-ethoxypyridin-3-yl)-3-isopropyl-1-methyl-1H-pyrazolo[3,4-b]pyridin-4-amine and 2-methyloxazole-4-carbaldehyde.

$^1$H NMR (CDCl$_3$ 400 MHz): δ 8.29 (d, J=6.8 Hz, 1H), 8.19 (d, J=7.2 Hz, 1H), 7.51 (s, 1H), 7.04-7.01 (m, 1H), 6.95 (s, 1H), 5.34 (brs, 1H), 4.49-4.44 (m, 4H), 4.04 (s, 3H), 3.34-3.31 (m, 1H), 2.48 (s, 3H) 1.48-1.36 (m, 9H). LC-MS: t$_R$=2.114 minutes (Method C), m/z=407.0 [M+H]+.

Example 3: 6-(2-ethoxy-3-pyridyl)-3-isopropyl-1-methyl-N-(1H-pyrazol-3-ylmethyl)pyrazolo[3,4-b]pyridin-4-amine

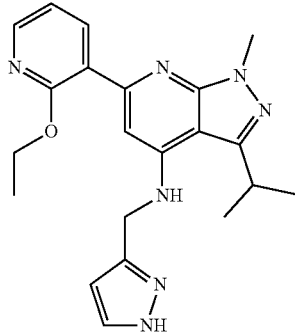 [SMILES: CCOc1ncccc1-c1cc(NCc2cc[nH]n2)c2c(C(C)C)nn(C)c2n1]

Prepared in a way similar to example 1 from 6-(2-ethoxypyridin-3-yl)-3-isopropyl-1-methyl-1H-pyrazolo[3,4-b]pyridin-4-amine and 1H-pyrazole-3-carbaldehyde.

$^1$H NMR (CDCl$_3$ 400 MHz): δ 8.30 (dd, J=1.6, 7.2 Hz, 1H), 8.20 (dd, J=2.0, 4.8 Hz, 1H), 7.60 (d, J=2.0 Hz, 1H), 7.05-7.01 (m, 2H), 6.36 (d, J=2.0 Hz, 1H), 5.58-5.57 (m, 1H), 4.62 (d, J=4.8 Hz, 2H), 4.49 (q, J=7.2 Hz, 2H), 4.05 (s, 3H), 3.37-3.33 (m, 1H), 1.47 (d, J=6.8 Hz, 6H), 1.42 (t, J=6.8 Hz, 3H). LC-MS: t$_R$=2.1$^{96}$ minutes (Method C), m/z=392.1 [M+H]+.

Example 4: 6-(2-ethoxy-3-pyridyl)-3-isopropyl-1-methyl-N-[(1-methyl-1,2,4-triazol-3-yl)methyl]pyrazolo[3,4-b]pyridin-4-amine

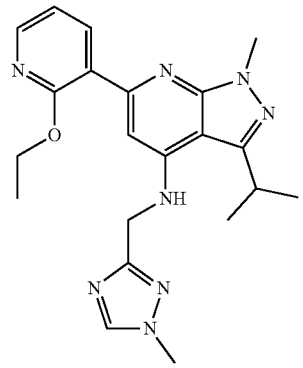 [SMILES: CCOc1ncccc1-c1cc(NCc2ncn(C)n2)c2c(C(C)C)nn(C)c2n1]

Prepared in a way similar to example 1 from 6-(2-ethoxypyridin-3-yl)-3-isopropyl-1-methyl-1H-pyrazolo[3,4-b]pyridin-4-amine and 1-methyl-1,2,4-triazole-3-carbaldehyde. 1H NMR (CDCl$_3$ 400 MHz): δ 8.31 (d, J=7.2 Hz, 1H), 8.20 (d, J=5.2 Hz, 1H), 8.05 (s, 1H), 7.04-7.01 (m, 2H), 5.82 (s, 1H), 4.62 (d, J=4.4 Hz, 2H), 4.50 (q, J=7.2 Hz, 2H), 4.05 (s, 3H), 3.95 (s, 3H), 3.44-3.41 (m, 1H), 1.50 (d, J=6.8 Hz, 6H), 1.46 (t, J=7.2 Hz, 3H) LC-MS: t$_R$=2.115 minutes (Method B), m/z=407.1 [M+H]$^+$.

Example 5: 6-(2-ethoxy-3-pyridyl)-3-isopropyl-1-methyl-N-[(5-methyl-1,2,4-oxadiazol-3-yl)methyl]pyrazolo[3,4-b]pyridin-4-amine

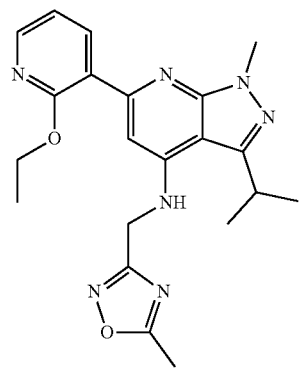 [SMILES: CCOc1ncccc1-c1cc(NCc2noc(C)n2)c2c(C(C)C)nn(C)c2n1]

Prepared in a way similar to example 1 from 6-(2-ethoxypyridin-3-yl)-3-isopropyl-1-methyl-1H-pyrazolo[3,4-b]pyridin-4-amine and 5-methyl-1,2,4-oxadiazole-3-carbaldehyde.

$^1$H NMR (CDCl$_3$ 400 MHz): δ 8.30 (dd, J=2.0, 7.2 Hz, 1H), 8.20 (dd, J=2.0, 4.8 Hz, 1H), 7.04-7.01 (m, 2H), 5.54 (brs, 1H), 4.66 (d, J=6.4 Hz, 2H), 4.50 (q, J=7.2 Hz, 2H), 4.05 (s, 3H), 3.42-3.35 (m, 1H), 2.63 (s, 3H), 1.50 (d, J=6.8 Hz, 6H), 1.45 (t, J=7.2 Hz, 3H). LC-MS: t$_R$=2.113 minutes (Method C), m/z=408.0 [M+H]+.

Example 6: 6-(2-ethoxy-3-pyridyl)-3-isopropyl-1-methyl-N-[(5-methyl-1H-pyrazol-3-yl)methyl]pyrazolo[3,4-b]pyridin-4-amine

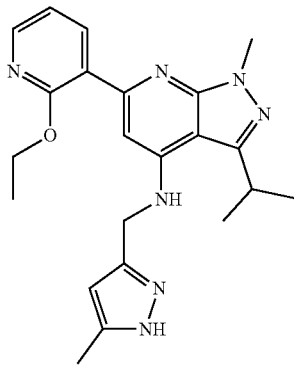 [SMILES: CCOc1ncccc1-c1cc(NCc2cc(C)[nH]n2)c2c(C(C)C)nn(C)c2n1]

Prepared in a way similar to example 1 from 6-(2-ethoxypyridin-3-yl)-3-isopropyl-1-methyl-1H-pyrazolo[3,4-b]pyridin-4-amine and 5-methyl-1H-pyrazole-3-carbaldehyde.

$^1$H NMR (CDCl$_3$ 400 MHz) δ 8.30 (d, J=6.8 Hz, 1H), 8.19 (brs, 1H), 7.02-6.99 (m, 2H), 6.07 (s, 1H), 5.53 (brs, 1H), 4.53-4.47 (m, 4H), 4.04 (s, 3H), 3.44-3.34 (m, 1H), 2.33 (s, 3H), 1.47 (d, J=6.4 Hz, 6H), 1.43-1.40 (m, 3H). LC-MS: $t_R$=2.340 minutes (Method B), m/z=406.1 [M+H]$^+$.

Example 7: 6-(2-ethoxy-3-pyridyl)-3-isopropyl-N-[(2-methoxy-4-pyridyl)methyl]-1-methyl-pyrazolo[3,4-b]pyridin-4-amine

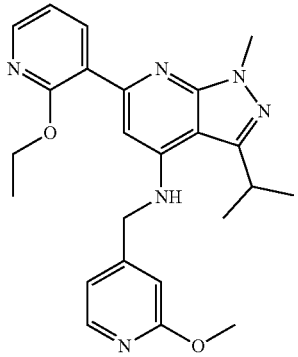 [SMILES: CCOc1ncccc1-c1cc(NCc2ccnc(OC)c2)c2c(C(C)C)nn(C)c2n1]

Prepared in a way similar to example 1 from 6-(2-ethoxypyridin-3-yl)-3-isopropyl-1-methyl-1H-pyrazolo[3,4-b]pyridin-4-amine and 2-methoxypyridine-4-carbaldehyde.

$^1$H NMR (CDCl$_3$ 400 MHz): δ 8.28 (dd, J=2.0, 7.6 Hz, 1H), 8.18-8.14 (m, 2H), 7.00 (dd, J=4.8, 7.6 Hz, 1H), 6.90 (d, J=6.0 Hz, 1H), 6.83 (s, 1H), 6.76 (s, 1H), 5.31-5.25 (m, 1H), 4.59 (d, J=6.0 Hz, 2H), 4.35 (q, J=7.2 Hz, 2H), 4.06 (s, 3H), 3.93 (s, 3H), 3.37-3.29 (m, 1H), 1.50 (d, J=6.8 Hz, 6H), 1.23 (t, J=7.2 Hz, 3H). LC-MS: $t_R$=1.990 minutes (Method A), m/z=433.0 [M+H]$^+$.

Example 8: 2-(2-ethoxy-3-pyridyl)-5-isopropyl-7-methyl-N-[(1-methylimidazol-4-yl)methyl]imidazo[1,5-b]pyridazin-4-amine

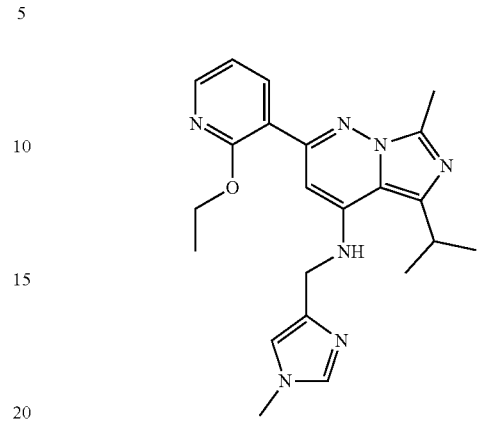

Prepared in a way similar to example 1 from 2-(2-ethoxypyridin-3-yl)-5-isopropyl-7-methylimidazo[1,5-b]pyridazin-4-amine and 1-methylimidazole-4-carbaldehyde.

$^1$H NMR (CDCl$_3$ 400 MHz): δ 8.20 (dd, J=2.0, 4.8 Hz, 1H), 8.03 (dd, J=2.0, 7.6 Hz, 1H), 7.43 (s, 1H), 6.99 (dd, J=4.8, 7.2 Hz, 1H), 6.86 (s, 1H), 6.09 (s, 1H), 5.59 (brs, 1H), 4.48-4.41 (m, 4H), 3.68 (s, 3H), 3.33-3.26 (m, 1H), 2.68 (s, 3H), 1.42 (d, J=7.2 Hz, 6H), 1.38 (t, J=6.8 Hz, 3H). LC-MS: $t_R$=2.202 minutes (Method B), m/z=406.1 [M+H]$^+$.

Example 9: 2-(2-ethoxy-3-pyridyl)-5-isopropyl-7-methyl-N-[(2-methyloxazol-4-yl)methyl]imidazo[1,5-b]pyridazin-4-amine

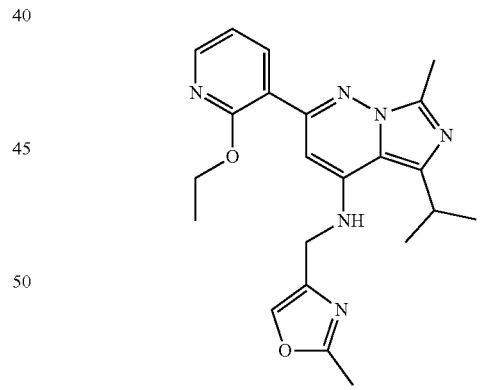

Prepared in a way similar to example 1 from 2-(2-ethoxypyridin-3-yl)-5-isopropyl-7-methylimidazo[1,5-b]pyridazin-4-amine and 2-methyloxazole-4-carbaldehyde.

$^1$H NMR (CDCl$_3$ 400 MHz): δ 8.22 (dd, J=2.0, 5.2 Hz, 1H), 8.03 (dd, J=2.0, 7.2 Hz, 1H), 7.52 (s, 1H), 6.99 (dd, J=5.2, 7.2 Hz, 1H), 6.07 (s, 1H), 5.51-5.34 (m, 1H), 4.45 (q, J=7.2 Hz, 2H), 4.39 (d, J=5.2 Hz, 2H), 3.35-3.13 (m, 1H), 2.69 (s, 3H), 2.48 (s, 3H), 1.44 (d, J=6.8 Hz, 6H), 1.36 (t, J=7.2 Hz, 3H). LC-MS: $t_R$=2.219 minutes (Method C), m/z=407.0 [M+H]$^+$.

Example 10: 2-(2-ethoxy-3-pyridyl)-5-isopropyl-7-methyl-N-(1H-pyrazol-3-ylmethyl)imidazo[1,5-b]pyridazin-4-amine

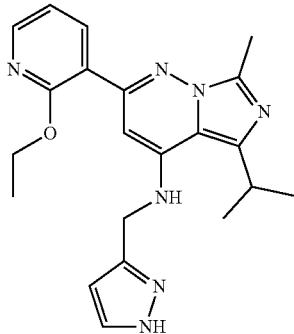 [SMILES: CCOc1ncccc1-c1cc(NCc2cc[nH]n2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 1H-pyrazole-3-carbaldehyde.

$^1$H NMR (CDCl$_3$ 400 MHz): δ 8.22 (dd, J=2.0, 4.2 Hz, 1H), 8.04 (dd, J=2.0, 7.2 Hz, 1H), 7.61 (d, J=2.0 Hz, 1H), 7.00 (dd, J=4.2, 7.6 Hz, 1H), 6.36 (d, J=2.0 Hz, 1H), 6.13 (s, 1H), 5.72 (brs, 1H), 4.56 (d, J=4.8 Hz, 2H), 4.47 (q, J=7.2 Hz, 2H), 3.37-3.30 (m, 1H), 2.71 (s, 3H), 1.46 (d, J=6.8 Hz, 6H), 1.40 (t, J=7.2 Hz, 3H). LC-MS: t$_R$=2.016 minutes (Method C), m/z=392.1 [M+H]$^+$.

Example 11: 2-(2-ethoxy-3-pyridyl)-5-isopropyl-7-methyl-N-[(1-methyl-1,2,4-triazol-3-yl)methyl]imidazo[1,5-b]pyridazin-4-amine

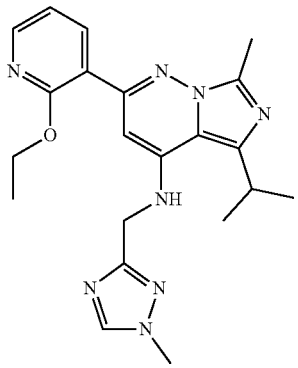 [SMILES: CCOc1ncccc1-c1cc(NCc2ncn(C)n2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 1-methyl-1,2,4-triazole-3-carbaldehyde.

$^1$H NMR (CDCl$_3$ 400 MHz): δ 8.24 (br.s, 1H), 8.06 (br.s, 2H), 7.00 (t, J=4.8 Hz, 1H), 6.13 (s, 1H), 5.92 (br.s, 1H), 4.56 (d, J=3.6 Hz, 2H), 4.48 (q, J=6.8 Hz, 2H), 3.95 (s, 3H), 3.43-3.39 (m, 1H), 2.70 (s, 3H), 1.48 (d, J=6.4 Hz, 6H), 1.43 (t, J=6.8 Hz, 3H). LC-MS: t$_R$=1.951 minutes (Method C), m/z=407.1 [M+H]$^+$.

Example 12: 2-(2-ethoxy-3-pyridyl)-5-isopropyl-7-methyl-N-[(5-methyl-1,2,4-oxadiazol-3-yl)methyl]imidazo[1,5-b]pyridazin-4-amine

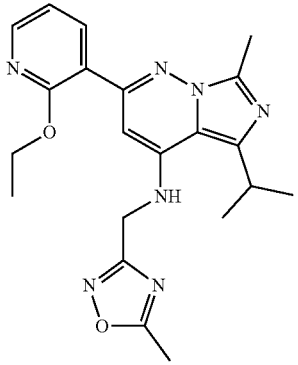 [SMILES: CCOc1ncccc1-c1cc(NCc2noc(C)n2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 5-methyl-1,2,4-oxadiazole-3-carbaldehyde.

$^1$H NMR (CDCl$_3$ 400 MHz): δ 8.22 (d, J=3.6 Hz, 1H), 8.04 (d, J=7.6 Hz, 1H), 7.00 (t, J=4.2 Hz, 1H), 6.15 (s, 1H), 5.62 (br s, 1H), 4.60 (d, J=5.6 Hz, 2H), 4.48 (q, J=7.2 Hz, 2H), 3.33-3.31 (m, 1H), 2.70 (s, 3H), 2.64 (s, 3H), 1.47 (d, J=6.8 Hz, 6H), 1.42 (t, J=7.2 Hz, 3H). LC-MS: t$_R$=2.016 minutes (Method C), m/z=392.1 [M+H]$^+$.

Example 13: 2-(2-ethoxy-3-pyridyl)-5-isopropyl-7-methyl-N-[(5-methyl-1H-pyrazol-3-yl)methyl]imidazo[1,5-b]pyridazin-4-amine

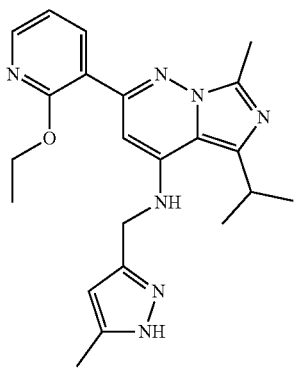 [SMILES: CCOc1ncccc1-c1cc(NCc2cc(C)[nH]n2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 5-methyl-1H-pyrazole-3-carbaldehyde.

$^1$H NMR (CDCl$_3$ 400 MHz): δ 8.22 (dd, J=2.0, 4.8, 1H), 8.04 (dd, J=2.0, 7.2 Hz, 1H), 7.00 (dd, J=4.2, 7.6 Hz, 1H), 6.12 (s, 1H), 6.07 (s, 1H), 5.69 (br.s, 1H), 4.49-4.44 (m, 4H), 3.37-3.30 (m, 1H), 2.71 (s, 3H), 2.35 (s, 3H), 1.46 (d, J=6.8 Hz, 6H), 1.40 (t, J=7.2 Hz, 3H). LC-MS: t$_R$=2.078 minutes (Method C), m/z=406.1 [M+H]$^+$.

Example 14: 2-(2-ethoxy-3-pyridyl)-5-isopropyl-N-[(5-methoxy-3-pyridyl)methyl]-7-methyl-imidazo[1,5-b]pyridazin-4-amine

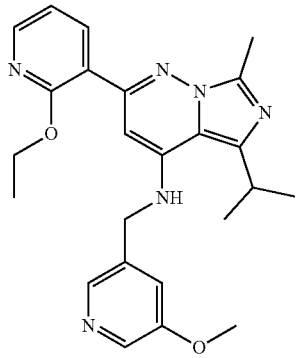 [SMILES: CCOc1ncccc1-c1cc(NCc2cncc(OC)c2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 5-methoxypyridine-3-carbaldehyde.

$^1$H NMR (CDCl$_3$ 400 MHz): δ 8.30-8.28 (m, 2H), 8.21 (dd, J=1.6, 4.8 Hz, 1H), 8.03 (dd, J=2.0, 7.6 Hz, 1H), 7.22 (s, 1H), 6.99 (dd, J=5.0, 7.3 Hz, 1H), 6.08 (s, 1H), 5.31-5.25 (m, 1H), 4.57 (d, J=5.6 Hz, 2H), 4.39 (q, J=7.2 Hz, 2H), 3.87 (s, 3H), 3.30-3.21 (m, 1H), 2.71 (s, 3H), 1.46 (d, J=7.2 Hz, 6H), 1.29-1.26 (t, J=7.2 Hz, 3H). LC-MS: t$_R$=2.149 minutes (Method D), m/z=433.1 [M+H]$^+$.

Example 15: 2-(2-ethoxy-3-pyridyl)-5-isopropyl-N-[(2-methoxy-4-pyridyl)methyl]-7-methyl-imidazo[1,5-b]pyridazin-4-amine

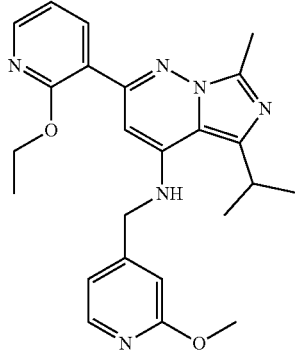 [SMILES: CCOc1ncccc1-c1cc(NCc2ccnc(OC)c2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 2-methoxypyridine-4-carbaldehyde.

$^1$H NMR (CDCl$_3$ 400 MHz): δ 8.23-8.13 (m, 2H), 8.01 (d, J=6.8 Hz, 1H), 7.03-6.93 (m, 1H), 6.88 (d, J=4.8 Hz, 1H), 6.75 (s, 1H), 5.96 (s, 1H), 5.38 (brs, 1H), 4.54 (d, J=5.6 Hz, 2H), 4.33 (q, J=6.8 Hz, 2H), 3.94 (s, 3H), 3.31 (d, J=6.4 Hz, 1H), 2.71 (s, 3H), 1.52-1.46 (m, 6H), 1.20 (t, J=6.8 Hz, 3H). LC-MS: t$_R$=2.381 minutes (Method D), m/z=433.1 [M+H]$^+$.

Example 16: 2-(2-ethoxy-3-pyridyl)-5-isopropyl-7-methyl-N-[(2-methyloxazol-5-yl)methyl]imidazo[1,5-b]pyridazin-4-amine

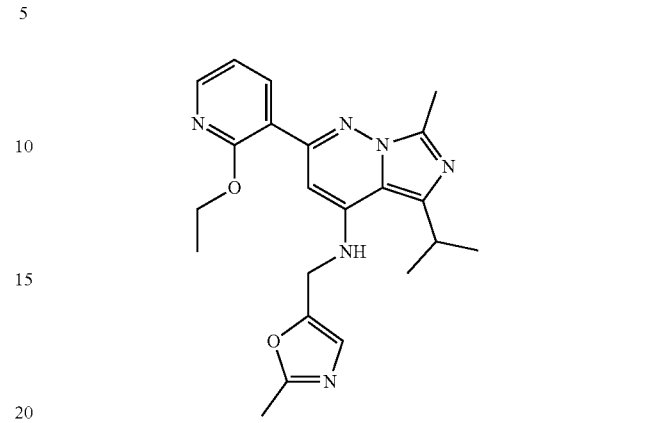

Prepared in a way similar to example 1 from 2-(2-ethoxypyridin-3-yl)-5-isopropyl-7-methylimidazo[1,5-b]pyridazin-4-amine and 2-methyloxazole-5-carbaldehyde.

$^1$H NMR (CDCl$_3$ 400 MHz): δ 8.23 (dd, J=4.8, 1.6 Hz, 1H), 8.03 (dd, J=7.6, 2.0 Hz, 1H), 7.02-6.99 (m, 1H), 6.93 (s, 1H), 6.13 (s, 1H), 5.18 (brs, 1H), 4.53-4.45 (m, 4H), 3.26-3.22 (m, 1H), 2.70 (s, 3H), 2.47 (s, 3H), 1.45 (d, J=6.8 Hz, 6H), 1.39 (t, J=7.2 Hz, 3H). LC-MS: t$_R$=2.329 minutes (Method B), m/z=407.0 [M+H]$^+$.

Example 17: 2-(2-ethoxy-3-pyridyl)-5-isopropyl-7-methyl-N-[(2-methylthiazol-5-yl)methyl]imidazo[1,5-b]pyridazin-4-amine

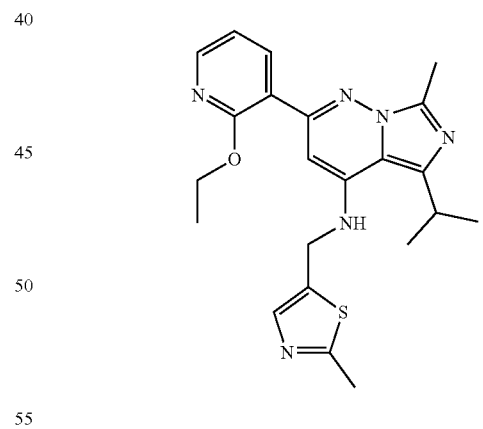

Prepared in a way similar to example 1 from 2-(2-ethoxypyridin-3-yl)-5-isopropyl-7-methylimidazo[1,5-b]pyridazin-4-amine and 2-methylthiazole-5-carbaldehyde.

$^1$H NMR (CDCl$_3$ 400 MHz): δ 8.23 (dd, J=5.2, 2.0 Hz, 1H), 8.04 (dd, J=7.6, 2.0 Hz, 1H), 7.59 (s, 1H), 7.02-6.99 (m, 1H), 6.15 (s, 1H), 5.21-5.18 (m, 1H), 4.67 (d, J=6.8 Hz, 2H), 4.46 (q, J=5.2 Hz, 2H) 3.23-3.19 (m, 1H), 2.71 (s, 3H), 2.70 (s, 3H), 1.44 (d, J=6.8 Hz, 6H), 1.39 (t, J=6.8 Hz, 3H). LC-MS: t$_R$=1.822 minutes (Method A), m/z=423.0 [M+H]$^+$.

Example 18: 2-(2-ethoxy-3-pyridyl)-5-isopropyl-7-methyl-N-(1H-pyrazol-4-ylmethyl)imidazo[1,5-b]pyridazin-4-amine

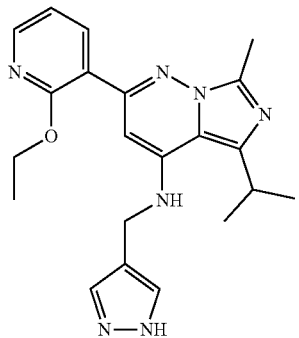 [SMILES: CCOc1ncccc1-c1cc(NCc2cn[nH]c2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 1H-pyrazole-4-carbaldehyde.

$^1$H NMR (CDCl$_3$ 400 MHz): δ 8.22 (dd, J=2.0, 4.8 Hz, 1H), 8.04 (dd, J=2.0, 7.6 Hz, 1H), 7.68 (s, 2H), 7.00 (dd, J=4.2, 7.6 Hz, 1H), 6.14 (s, 1H), 5.06 (brs, 1H), 4.49-4.44 (m, 4H), 3.22-3.17 (m, 1H), 2.70 (s, 3H), 1.41 (d, J=6.8 Hz, 6H), 1.37 (t, J=7.2 Hz, 3H). LC-MS: t$_R$=1.951 minutes (Method C), m/z=407.1 [M+H]$^+$.

Example 19: 6-(2-ethoxy-3-pyridyl)-3-isopropyl-1-methyl-N-[(1-methylpyrazol-4-yl)methyl]pyrazolo[3,4-b]pyridin-4-amine

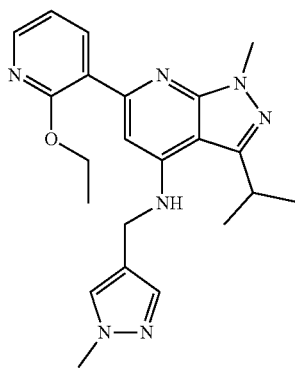 [SMILES: CCOc1ncccc1-c1cc(NCc2cnn(C)c2)c2c(C(C)C)nn(C)c2n1]

Preparation of 6-chloro-3-isopropyl-1-methyl-N-((1-methyl-1H-pyrazol-4-yl)methyl)-1H-pyrazolo[3,4-b]pyridin-4-amine

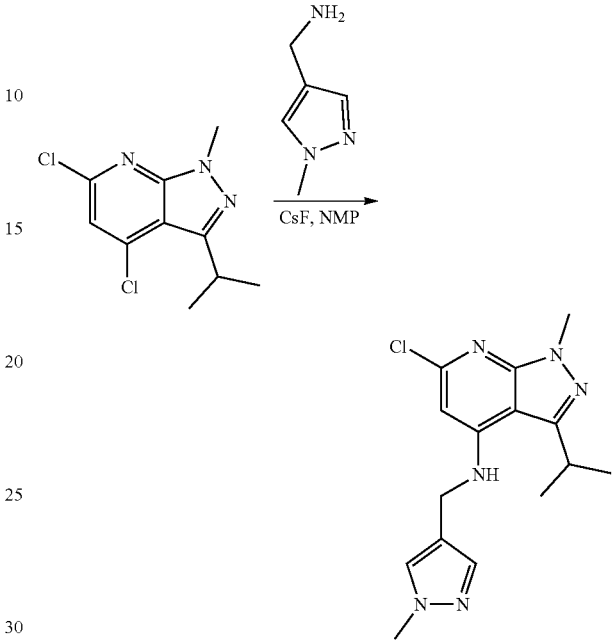

To a solution of 4,6-dichloro-3-isopropyl-1-methyl-1H-pyrazolo[3,4-b]pyridine (50 mg, 0.2 mmol) in NMP (1 mL) was added CsF (156 mg, 1 mmol) and (1-methylpyrazol-4-yl)methanamine hydrochloride (54 mg, 0.2 mmol). The mixture was stirred at 100° C. for 36 hours. The reaction mixture was filtered and the residue was washed with ethyl acetate (5 mL×2). The combined filtrates were concentrated. The crude product 6-chloro-3-isopropyl-1-methyl-N-((1-methyl-1H-pyrazol-4-yl)methyl)-1H-pyrazolo[3,4-b]pyridin-4-amine (65 mg) was used in the next step without further purification.

Preparation of 6-(2-ethoxypyridin-3-yl)-3-isopropyl-1-methyl-N-((1-methyl-1H-pyrazol-4-yl)methyl)-1H-pyrazolo[3,4-b]pyridin-4-amine

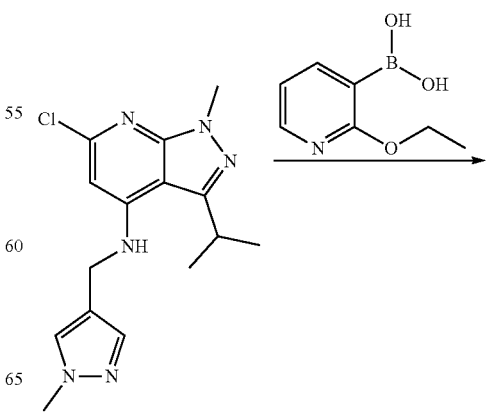

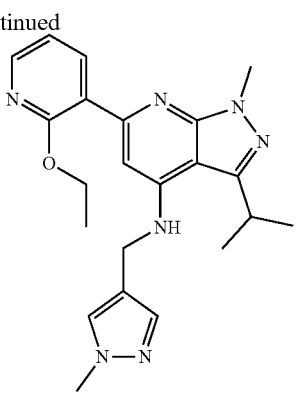

A mixture of 6-chloro-3-isopropyl-1-methyl-N-((1-methyl-1H-pyrazol-4-yl)methyl)-1H-pyrazolo[3,4-b]pyridin-4-amine (65 mg, 0.20 mmol), (2-ethoxy-3-pyridyl)boronic acid (68 mg, 0.41 mol), Pd(dppf)Cl$_2$ (38 mg, 0.05 mmol), Cs$_2$CO$_3$ (167 mg, 0.5 mmol) in dioxane (3 mL) and water (1 mL) was degassed and purged with nitrogen 3 times, and then the mixture was stirred at 100° C. for 1 hour under microwave irradiation. Water (30 mL) was added and the mixture was extracted with ethyl acetate (45 mL×3). The combined organic layers were washed with brine (20 mL), dried over Na$_2$SO$_4$ and concentrated. The crude mixture was purified by preparative HPLC to give 6-(2-ethoxypyridin-3-yl)-3-isopropyl-1-methyl-N-((1-methyl-1H-pyrazol-4-yl)methyl)-1H-pyrazolo[3,4-b]pyridin-4-amine (41 mg).

$^1$H NMR (CDCl$_3$ 400 MHz): δ 8.32 (dd, J=2.0, 7.6 Hz, 1H), 8.20 (dd, J=2.0, 4.8 Hz, 1H), 7.55 (s, 1H), 7.42 (s, 1H), 7.05-7.01 (m, 2H), 4.96 (brs, 1H), 4.48 (q, J=7.2 Hz, 2H), 4.43 (d, J=4.8 Hz, 2H), 4.06 (s, 3H), 3.89 (s, 3H), 3.26-3.19 (m, 1H), 1.43 (d, J=6.8 Hz 6H), 1.41-1.38 (m, 3H). LC-MS: t$_R$=1.971 minutes (Method C), m/z=406.1 [M+H]$^+$.

Example 20: 6-(2-ethoxy-3-pyridyl)-3-isopropyl-1-methyl-N-[(2-methyltetrazol-5-yl)methyl]pyrazolo[3,4-b]pyridin-4-amine

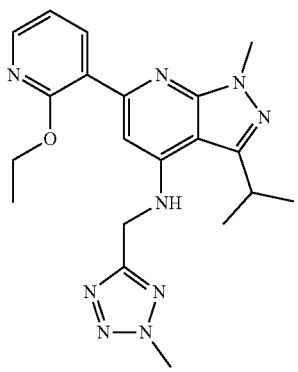

Prepared in a way similar to example 19 from 4,6-dichloro-3-isopropyl-1-methyl-1H-pyrazolo[3,4-b]pyridine, (2-ethoxy-3-pyridyl)boronic acid and (2-methyltetrazol-5-yl)methanamine. $^1$H NMR (CDCl$_3$ 400 MHz): δ 8.31 (dd, J=7.6, 2.0 Hz, 1H), 8.20 (dd, J=4.8, 2.0 Hz, 1H), 7.05-7.03 (m, 2H), 5.67-5.64 (m, 1H), 4.83 (d, J=5.2 Hz, 2H), 4.50 (q, J=7.2 Hz, 2H), 4.38 (s, 3H), 4.05 (s, 3H), 3.43-3.34 (m, 1H), 1.50 (d, J=6.8 Hz, 6H), 1.45 (t, J=7.2 Hz, 3H). LC-MS: t$_R$=2.081 minutes (Method C), m/z=408.0 [M+H]$^+$ Example 21: 6-(2-ethoxy-3-pyridyl)-3-isopropyl-1-methyl-N-[(1-methylpyrazol-3-yl)methyl]pyrazolo[3,4-b]pyridin-4-amine

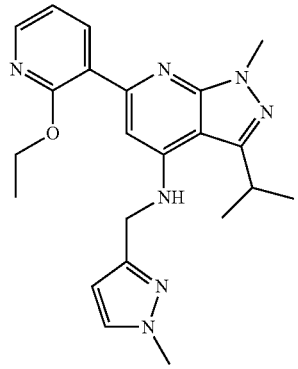 [SMILES: CCOc1ncccc1-c1cc(NCc2ccn(C)n2)c2c(C(C)C)nn(C)c2n1]

Prepared in a way similar to example 19 from 4,6-dichloro-3-isopropyl-1-methyl-1H-pyrazolo[3,4-b]pyridine, (2-ethoxy-3-pyridyl)boronic acid and (1-methylpyrazol-3-yl)methanamine.

$^1$H NMR (CDCl$_3$ 400 MHz): δ 8.31 (dd, J=2.0, 7.6 Hz, 1H), 8.20 (dd, J=2.0, 5.2 Hz, 1H), 7.60 (s, 1H), 7.06-7.01 (m, 2H), 5.12-5.09 (m, 1H), 4.72 (d, J=5.2 Hz, 2H), 4.48 (q, J=6.8 Hz, 2H), 4.05 (s, 3H), 3.29-3.22 (m, 1H), 2.70 (s, 3H), 1.46 (d, J=6.8 Hz, 6H), 1.39 (t, J=6.8 Hz, 3H). LC-MS: t$_R$=1.989 minutes (Method A), m/z=423.0 [M+H]$^+$.

Example 22: 2-(2-ethoxy-3-pyridyl)-5-isopropyl-7-methyl-N-[(1-methylpyrazol-4-yl)methyl]imidazo[1,5-b]pyridazin-4-amine

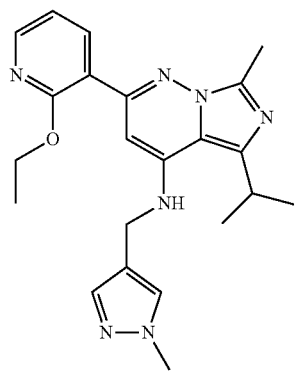 [SMILES: CCOc1ncccc1-c1cc(NCc2cnn(C)c2)c2c(C(C)C)nc(C)n2n1]

Prepared in a way similar to example 19 from 4,6-dichloro-3-isopropyl-1-methyl-1H-pyrazolo[3,4-b]pyridine, (2-ethoxy-3-pyridyl)boronic acid and (1-methylpyrazol-4-yl)methanamine.

$^1$H NMR (CDCl$_3$ 400 MHz): δ 8.21 (dd, J=1.6, 4.8 Hz, 1H), 8.03 (dd, J=2.0, 7.2 Hz, 1H), 7.53 (s, 1H), 7.41 (s, 1H), 6.99 (dd, J=4.8, 7.6 Hz, 1H), 6.12 (s, 1H), 5.01 (brs, 1H), 4.45 (q, J=6.8 Hz, 2H), 4.36 (d, J=4.8 Hz, 2H), 3.91 (s, 3H), 3.20-3.13 (m, 1H), 2.68 (s, 3H), 1.41-1.35 (m, 9H). LC-MS: t$_R$=2.004 minutes (Method C), m/z=406.1 [M+H]$^+$.

Example 23: 2-(2-ethoxy-3-pyridyl)-5-isopropyl-7-methyl-N-[(2-methyltetrazol-5-yl)methyl]imidazo[1,5-b]pyridazin-4-amine

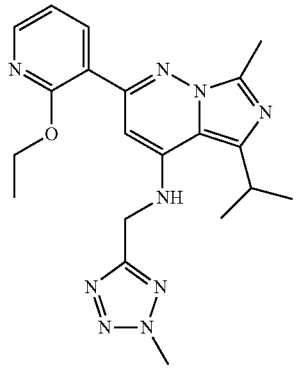 [SMILES: CCOc1ncccc1-c1cc(NCc2nnn(C)n2)c2c(C(C)C)nc(C)n2n1]

Prepared in a way similar to example 19 from 4,6-dichloro-3-isopropyl-1-methyl-1H-pyrazolo[3,4-b]pyridine, (2-ethoxy-3-pyridyl)boronic acid and (2-methyltetrazol-5-yl)methanamine.

$^1$H NMR (CDCl$_3$ 400 MHz): δ 8.23 (dd, J=4.8, 2.0 Hz, 1H), 8.04 (dd, J=7.2, 2.0 Hz, 1H), 7.02-6.99 (m, 1H), 6.17 (s, 1H), 5.75-5.72 (m, 1H), 4.78 (d, J=5.2 Hz, 2H), 4.48 (q, J=7.2 Hz, 2H), 4.38 (s, 3H), 3.41-3.31 (m, 1H), 2.70 (s, 3H), 1.48 (d, J=6.8 Hz, 6H), 1.42 (t, J=7.2 Hz, 3H). LC-MS: t$_R$=2.052 minutes (Method C), m/z=408.1 [M+H]$^+$.

Example 24: 2-(2-ethoxy-3-pyridyl)-5-isopropyl-7-methyl-N-[(1-methylpyrazol-3-yl)methyl]imidazo[1,5-b]pyridazin-4-amine

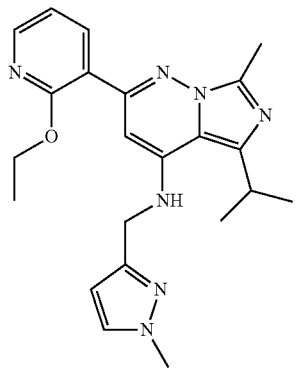 [SMILES: CCOc1ncccc1-c1cc(NCc2ccn(C)n2)c2c(C(C)C)nc(C)n2n1]

Prepared in a way similar to example 19 from 4,6-dichloro-3-isopropyl-1-methyl-1H-pyrazolo[3,4-b]pyridine, (2-ethoxy-3-pyridyl)boronic acid and (1-methylpyrazol-3-yl)methanamine.

$^1$H NMR (CDCl$_3$ 400 MHz): δ 8.22 (dd, J=4.8, 2.0 Hz, 1H), 8.04 (dd, J=7.2, 2.0 Hz, 1H), 7.37 (d, J=2.4 Hz, 1H), 7.00 (dd, J=7.4, 4.8 Hz, 1H), 6.25 (d, J=2.4 Hz, 1H), 6.12 (s, 1H), 5.66 (brs, 1H), 4.44-4.51 (m, 4H), 3.92 (s, 3H), 3.37-3.30 (m, 1H), 2.71 (s, 3H), 1.46 (d, J=6.8 Hz, 6H), 1.40 (t, J=7.2 Hz, 3H). LC-MS: t$_R$=2.069 minutes (Method C), m/z=406.1 [M+H]$^+$.

Example 25: 6-(2-ethoxy-3-pyridyl)-3-isopropyl-N-[(5-methoxy-3-pyridyl)methyl]-1-methyl-pyrazolo[3,4-b]pyridin-4-amine

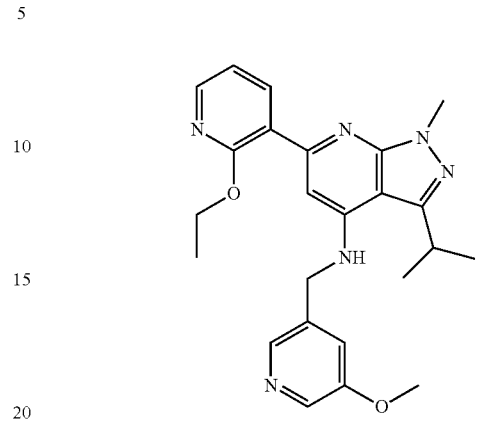

Prepared in a way similar to example 1 from 6-(2-ethoxy-3-pyridyl)-3-isopropyl-1-methyl-pyrazolo[3,4-b]pyridin-4-amine and 5-methoxypyridine-3-carbaldehyde.

$^1$H NMR (CDCl$_3$ 400 MHz): δ 8.31-8.29 (m, 3H), 8.18 (dd, J=2.0, 5.2 Hz, 1H), 7.24 (s, 1H), 7.02 (dd, J=4.8, 7.2 Hz, 1H), 6.95 (s, 1H), 5.20-5.17 (m, 1H), 4.62 (d, J=7.0 Hz, 2H), 4.40 (q, J=7.2 Hz, 2H), 4.06 (s, 3H), 3.85 (s, 3H), 3.33-3.26 (m, 1H), 1.47 (d, J=6.8 Hz, 6H), 1.30 (t, J=7.2 Hz, 3H) LC-MS: t$_R$=1.6 minutes (Method A), m/z=433.1 [M+H]$^+$.

Example 26: 6-(2-ethoxypyridin-3-yl)-3-isopropyl-1-methyl-N-((2-methyl-2H-1,2,3-triazol-4-yl)methyl)-1H-pyrazolo[3,4-b]pyridin-4-amine Preparation of 6-(2-ethoxypyridin-3-yl)-3-isopropyl-N-(4-methoxybenzyl)-1-methyl-N-((2-methyl-2H-1,2,3-triazol-4-yl)methyl)-1H-pyrazolo[3,4-b]pyridin-4-amine

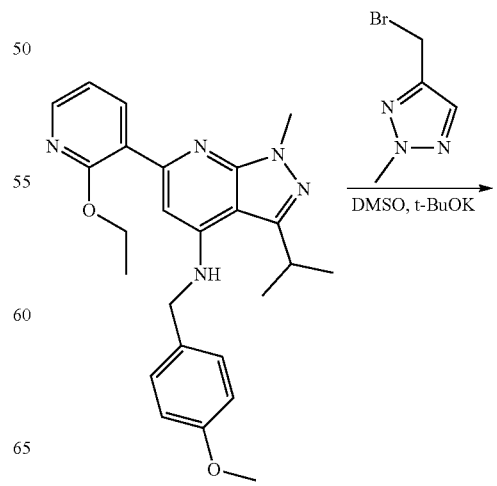

-continued

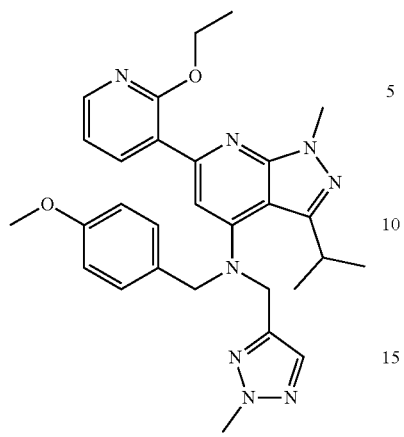

To a solution of 6-(2-ethoxypyridin-3-yl)-3-isopropyl-N-(4-methoxybenzyl)-1-methyl-1H-pyrazolo[3,4-b]pyridin-4-amine (0.1 g, 0.23 mmol) and t-BuOK (52 mg, 0.46 mmol) in DMSO (5 mL) was added 4-(bromomethyl)-2-methyl-2H-1,2,3-triazole (61 mg, 0.35 mmol). The reaction mixture was stirred at 100° C. for 12 hours. The solution was poured into ice-water (40 mL) and extracted with ethyl acetate (20 mL×3). The combined organic phases were washed with brine (20 mL×1), dried with anhydrous Na$_2$SO$_4$, filtered and concentrated in vacuum to afford 6-(2-ethoxypyridin-3-yl)-3-isopropyl-N-(4-methoxybenzyl)-1-methyl-N-((2-methyl-2H-1,2,3-triazol-4-yl)methyl)-1H-pyrazolo[3,4-b]pyridin-4-amine.

Preparation of 6-(2-ethoxypyridin-3-yl)-3-isopropyl-1-methyl-N-((2-methyl-2H-1,2,3-triazol-4-yl)methyl)-1H-pyrazolo[3,4-b]pyridin-4-amine

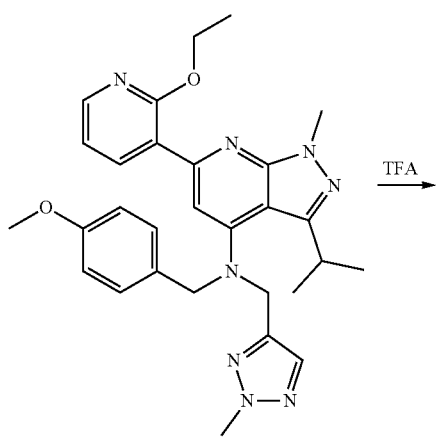

-continued

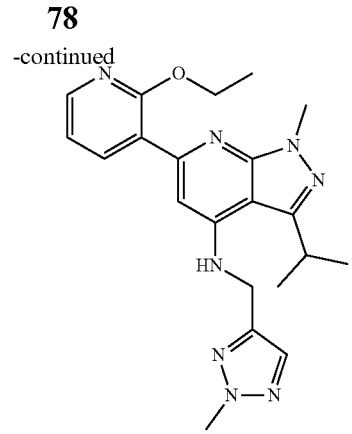

A solution of 6-(2-ethoxypyridin-3-yl)-3-isopropyl-N-(4-methoxybenzyl)-1-methyl-N-((2-methyl-2H-1,2,3-triazol-4-yl)methyl)-1H-pyrazolo[3,4-b]pyridin-4-amine (0.14 g, 0.27 mmol) in TFA (5 mL) was stirred at 60° C. for 12 hours. The solution was concentrated under vacuum, the residue was diluted with dichloromethane (20 mL) and washed with NaHCO$_3$ (aq.) until pH=8. The organic phase was washed with brine (8 mL), dried with anhydrous Na$_2$SO$_4$, filtered and concentrated in vacuum. The residue was purified by preparative HPLC to afford 6-(2-ethoxypyridin-3-yl)-3-isopropyl-1-methyl-N-((2-methyl-2H-1,2,3-triazol-4-yl)methyl)-1H-pyrazolo[3,4-b]pyridin-4-amine. $^1$H NMR (CDCl$_3$ 400 MHz): δ 8.30 (dd, J=7.2, 2.0 Hz, 1H), 8.19 (dd, J=5.2, 2.0 Hz, 1H), 7.58 (s, 1H), 7.03 (dd, J=7.6, 4.8 Hz, 1H), 7.00 (s, 1H), 5.39-5.36 (m, 1H), 4.63 (d, J=5.2 Hz, 2H), 4.48 (q, J=7.2 Hz, 2H), 4.21 (s, 3H), 4.05 (s, 3H), 3.37-3.27 (m, 1H), 1.47 (d, J=6.8 Hz, 6H), 1.40 (t, J=7.2 Hz, 3H). LC-MS: t$_R$=2.05 minutes (Method C), m/z=407.1 [M+H]$^+$.

Example 27: 6-(2-ethoxy-3-pyridyl)-3-isopropyl-1-methyl-N-[(2-methyloxazol-5-yl)methyl]pyrazolo[3,4-b]pyridin-4-amine

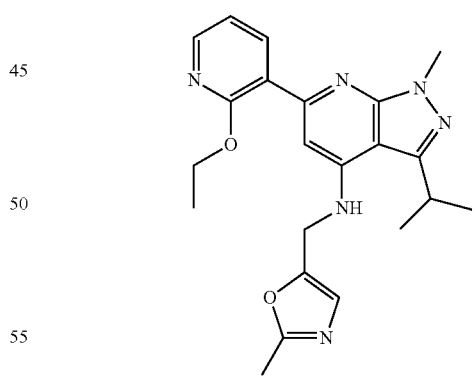

Prepared in a way similar to example 1 from 6-(2-ethoxy-3-pyridyl)-3-isopropyl-1-methyl-pyrazolo[3,4-b]pyridin-4-amine, 2-methyloxazole-5-carbaldehyde.

$^1$H NMR (CDCl$_3$ 400 MHz): δ 8.30 (dd, J=2.0, 7.6 Hz, 1H), 8.20 (dd, J=2.0, 4.8 Hz, 1H), 7.05-7.00 (m, 2H), 6.92 (s, 1H), 5.10 (brs, 1H), 4.58 (d, J=5.6 Hz, 2H), 4.50 (q, J=7.2 Hz, 2H), 4.05 (s, 3H), 3.32-3.26 (m, 1H), 2.46 (s, 3H), 1.47 (d, J=7.2 Hz, 6H), 1.41 (t, J=7.2 Hz, 3H). LC-MS: t$_R$=2.45 minutes (Method B), m/z=407.1 [M+H]$^+$.

Example 28: 6-(2-ethoxy-3-pyridyl)-3-isopropyl-1-methyl-N-[(2-methylthiazol-5-yl)methyl]pyrazolo[3,4-b]pyridin-4-amine

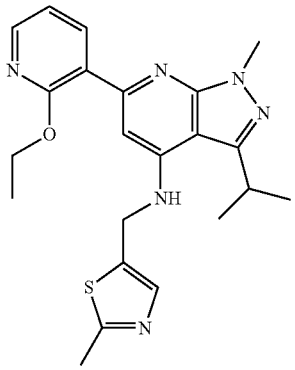 [SMILES: CCOc1ncccc1-c1cc(NCc2cnc(C)s2)c2c(C(C)C)nn(C)c2n1]

Prepared in a way similar to example 1 from 6-(2-ethoxy-3-pyridyl)-3-isopropyl-1-methyl-pyrazolo[3,4-b]pyridin-4-amine and 2-methylthiazole-5-carbaldehyde.

$^1$H NMR (CDCl$_3$ 400 MHz): δ 8.31 (dd, J=2.0, 7.6 Hz, 1H), 8.20 (dd, J=2.0, 5.2 Hz, 1H), 7.60 (s, 1H), 7.06-7.01 (m, 2H), 5.12-5.09 (m, 1H), 4.72 (d, J=5.2 Hz, 2H), 4.48 (q, J=6.8 Hz, 2H), 4.05 (s, 3H), 3.29-3.22 (m, 1H), 2.70 (s, 3H), 1.46 (d, J=6.8 Hz, 6H), 1.39 (t, J=6.8 Hz, 3H). LC-MS: t$_R$=1.99 minutes (Method A), m/z=423 [M+H]$^+$.

Example 29: 6-(2-ethoxy-3-pyridyl)-3-isopropyl-1-methyl-N-[(1-methyltriazol-4-yl)methyl]pyrazolo[3,4-b]pyridin-4-amine

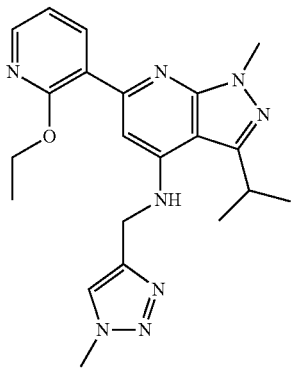 [SMILES: CCOc1ncccc1-c1cc(NCc2cn(C)nn2)c2c(C(C)C)nn(C)c2n1]

Prepared in a way similar to example 26 from 6-(2-ethoxypyridin-3-yl)-3-isopropyl-N-(4-methoxybenzyl)-1-methyl-1H-pyrazolo[3,4-b]pyridin-4-amine and 4-(chloromethyl)-1-methyl-1H-1,2,3-triazole.

$^1$H NMR (CDCl$_3$ 400 MHz): δ 8.33 (dd, J=7.6, 2.0 Hz, 1H), 8.20 (dd, J=4.8, 2.0 Hz, 1H), 7.52 (s, 1H), 7.05-7.03 (m, 1H), 7.02 (s, 1H), 5.53 (brs, 1H), 4.69 (d, J=5.2 Hz, 2H), 4.47 (q, J=7.2 Hz, 2H), 4.10 (s, 3H), 4.05 (s, 3H), 3.37-3.30 (m, 1H), 1.46 (d, J=6.8 Hz, 6H), 1.38 (t, J=7.2 Hz, 3H). LC-MS: t$_R$=1.7 minutes (Method C), m/z=407.1 [M+H]$^+$.

Example 30: 6-(2-ethoxy-3-pyridyl)-3-isopropyl-1-methyl-N-(1H-pyrazol-4-ylmethyl)pyrazolo[3,4-b]pyridin-4-amine

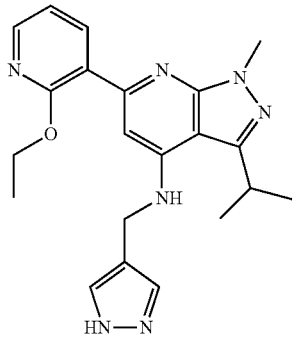 [SMILES: CCOc1ncccc1-c1cc(NCc2cn[nH]c2)c2c(C(C)C)nn(C)c2n1]

Prepared in a way similar to example 1 from 6-(2-ethoxy-3-pyridyl)-3-isopropyl-1-methyl-pyrazolo[3,4-b]pyridin-4-amine and 1H-pyrazole-4-carbaldehyde.

$^1$H NMR (CDCl$_3$ 400 MHz): δ 8.32 (dd, J=2.0, 7.6 Hz, 1H), 8.19 (dd, J=2.0, 4.8 Hz, 1H), 7.68 (s, 2H), 7.05-7.01 (m, 2H), 4.98-4.96 (m, 1H), 4.51-4.45 (m, 4H), 4.05 (s, 3H), 3.25-3.21 (m, 1H), 1.43 (d, J=6.8 Hz, 6H), 1.41-1.40 (m, 3H). LC-MS: t$_R$=2.24 minutes (Method B), m/z=392 [M+H]$^+$.

Example 31: 6-(2-ethoxy-3-pyridyl)-3-isopropyl-1-methyl-N-[(5-methyl-1,3,4-oxadiazol-2-yl)methyl]pyrazolo[3,4-b]pyridin-4-amine

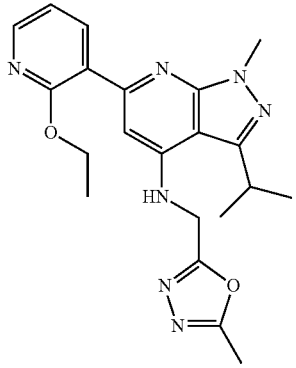 [SMILES: CCOc1ncccc1-c1cc(NCc2nnc(C)o2)c2c(C(C)C)nn(C)c2n1]

Prepared in a way similar to example 19 from 4,6-dichloro-3-isopropyl-1-methyl-1H-pyrazolo[3,4-b]pyridine, (5-methyl-1,3,4-oxadiazol-2-yl)methanamine oxalate and (2-ethoxypyridin-3-yl)boronic acid.

$^1$H NMR (CDCl$_3$ 400 MHz): δ 8.30 (dd, J=7.2, 2.0 Hz, 1H), 8.20 (dd, J=4.8, 2.0 Hz, 1H), 7.05-7.02 (m, 2H), 5.54-5.51 (m, 1H), 4.75 (d, J=5.6 Hz, 2H), 4.51 (q, J=7.2 Hz, 2H), 4.06 (s, 3H), 3.41-3.35 (m, 1H), 2.56 (s, 3H), 1.50 (d, J=6.8 Hz, 6H), 1.44 (t, J=7.2 Hz, 3H). LC-MS: t$_R$=1.98 minutes (Method C), m/z=408.1 [M+H]$^+$.

Example 32: 6-(2-ethoxy-3-pyridyl)-3-isopropyl-1-methyl-N-[(3-methyl-1,2,4-oxadiazol-5-yl)methyl]pyrazolo[3,4-b]pyridin-4-amine

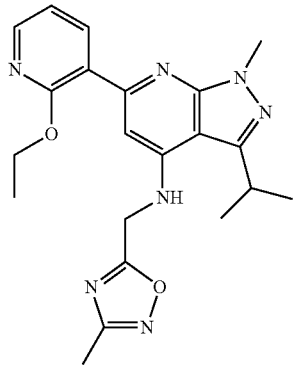 [SMILES: CCOc1ncccc1-c1cc(NCc2nc(C)no2)c2c(C(C)C)nn(C)c2n1]

Prepared in a way similar to example 19 from 4,6-dibromo-3-isopropyl-1-methyl-1H-pyrazolo[3,4-b]pyridine, (3-methyl-1,2,4-oxadiazol-5-yl)methanamine hydrochloride and (2-ethoxypyridin-3-yl)boronic acid.

$^1$H NMR (CDCl$_3$ 400 MHz): δ 8.31 (dd, J=2.0, 7.6 Hz, 1H), 8.20 (dd, J=2.0, 4.8 Hz, 1H), 7.03 (dd, J=4.8, 7.6 Hz, 1H), 6.97 (s, 1H), 5.56 (brs, 1H), 4.78 (d, J=5.6 Hz, 2H), 4.49 (q, J=7.2 Hz, 2H), 4.06 (s, 3H), 3.43-3.36 (m, 1H), 2.44 (s, 3H), 1.51 (d, J=6.8 Hz, 6H), 1.43 (t, J=6.8 Hz, 3H). LC-MS: t$_R$=2.22 minutes (Method C), m/z=408.1 [M+H]$^+$.

Example 33: 3-isopropyl-1-methyl-N-[(1-methyl-1,2,4-triazol-3-yl)methyl]-6-(2-propoxy-3-pyridyl)pyrazolo[3,4-b]pyridin-4-amine

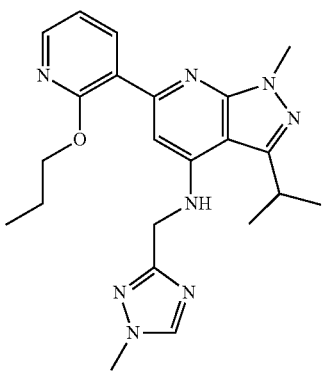 [SMILES: CCCOc1ncccc1-c1cc(NCc2ncn(C)n2)c2c(C(C)C)nn(C)c2n1]

Prepared in a way similar to example 1 from 3-isopropyl-N-(4-methoxybenzyl)-1-methyl-6-(2-propoxypyridin-3-yl)-1H-pyrazolo[3,4-b]pyridin-4-amine and 1-methyl-1,2,4-triazole-3-carbaldehyde.

$^1$H NMR (CDCl$_3$ 400 MHz): δ=8.29 (dd, J=1.9, 7.4 Hz, 1H), 8.20 (dd, J=1.9, 4.9 Hz, 1H), 8.05 (s, 1H), 7.02 (dd, J=5.0, 7.3 Hz, 1H), 6.97 (s, 1H), 5.83 (brs, 1H), 4.61 (d, J=4.5 Hz, 2H), 4.39 (t, J=6.8 Hz, 2H), 4.05 (s, 3H), 3.95 (s, 3H), 3.48-3.37 (m, 1H), 1.86 (sxt, J=7.2 Hz, 2H), 1.50 (d, J=7.0 Hz, 6H), 1.06 (t, J=7.4 Hz, 3H). LC-MS: t$_R$=1.98 minutes (Method C), m/z=421.1 [M+H]$^+$.

Example 34: 3-isopropyl-1-methyl-N-[(1-methyl-imidazol-4-yl)methyl]-6-(2-propoxy-3-pyridyl)pyrazolo[3,4-b]pyridin-4-amine

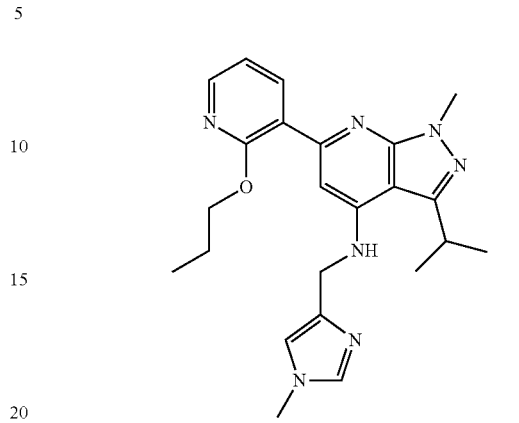

Prepared in a way similar to example 1 from 3-isopropyl-N-(4-methoxybenzyl)-1-methyl-6-(2-propoxypyridin-3-yl)-1H-pyrazolo[3,4-b]pyridin-4-amine and 1-methylimidazole-4-carbaldehyde.

$^1$H NMR (CDCl$_3$ 400 MHz): δ=8.29 (dd, J=1.9, 7.4 Hz, 1H), 8.19 (dd, J=1.9, 4.9 Hz, 1H), 7.45 (s, 1H), 7.02 (dd, J=4.9, 7.4 Hz, 1H), 6.96 (s, 1H), 6.85 (s, 1H), 5.51 (brs, 1H), 4.47 (d, J=5.0 Hz, 2H), 4.37 (t, J=6.8 Hz, 2H), 4.04 (s, 3H), 3.69 (s, 3H), 3.34 (quin, J=6.8 Hz, 1H), 1.82 (sxt, J=7.2 Hz, 2H), 1.46 (d, J=6.8 Hz, 6H), 1.05 (t, J=7.4 Hz, 3H). LC-MS: t$_R$=1.7 minutes (Method C), m/z=420.1 [M+H]$^+$.

Example 35: 6-(2-ethoxy-3-pyridyl)-3-isopropyl-1-methyl-N-[(4-methylpyrimidin-2-yl)methyl]pyrazolo[3,4-b]pyridin-4-amine

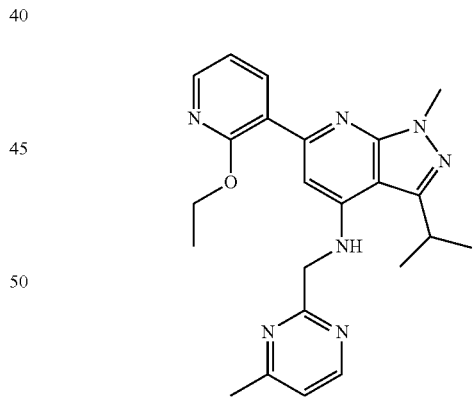

Prepared in a way similar to example 19 from 4,6-dichloro-3-isopropyl-1-methyl-1H-pyrazolo[3,4-b]pyridine, (4-methylpyrimidin-2-yl)methanamine hydrochloride and (2-ethoxypyridin-3-yl)boronic acid.

$^1$H NMR (CDCl$_3$ 400 MHz): δ 8.65 (d, J=4.2 Hz, 1H), 8.30 (d, J=7.6 Hz, 1H), 8.20 (d, J=4.2 Hz, 1H), 7.16 (d, J=5.6 Hz, 1H), 7.05-7.01 (m, 1H), 6.97 (s, 1H), 6.85 (brs, 1H), 4.71 (d, J=4.0 Hz, 2H), 4.51 (q, J=7.2 Hz, 2H), 4.06 (s, 3H), 3.62-3.58 (m, 1H), 2.62 (s, 3H), 1.57 (d, J=6.0 Hz, 6H), 1.47 (t, J=7.2 Hz, 3H). LC-MS: t$_R$=2.19 minutes (Method C), m/z=418.1 [M+H]$^+$.

Example 36: 6-(2-ethoxy-3-pyridyl)-3-isopropyl-1-methyl-N-(pyrimidin-2-ylmethyl)pyrazolo[3,4-b]pyridin-4-amine

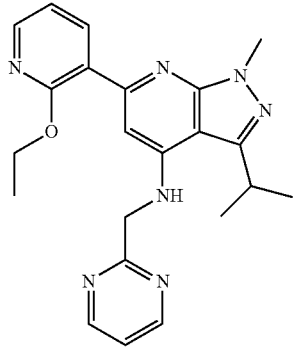 [SMILES: CCOc1ncccc1-c1cc(NCc2ncccn2)c2c(C(C)C)nn(C)c2n1]

Prepared in a way similar to example 19 from 4,6-dichloro-3-isopropyl-1-methyl-1H-pyrazolo[3,4-b]pyridine, pyrimidin-2-ylmethanamine hydrochloride and (2-ethoxypyridin-3-yl)boronic acid.

$^1$H NMR (CDCl$_3$, 400 MHz): δ 8.82 (d, J=4.8 Hz, 2H), 8.31 (dd, J=2.0, 7.6 Hz, 1H), 8.20 (dd, J=2.0, 7.6 Hz, 1H), 7.31 (t, J=4.8 Hz, 1H), 7.05 (dd, J=4.2, 7.6 Hz, 1H), 7.00 (s, 1H), 6.71 (brs, 1H), 4.78 (d, J=4.0 Hz, 2H), 4.51 (q, J=7.2 Hz, 2H), 4.06 (s, 3H), 3.60-3.53 (m, 1H), 1.55 (d, J=6.8 Hz, 6H), 1.48 (t, J=6.8 Hz, 3H). LC-MS: t$_R$=2.16 minutes (Method C), m/z=404.1 [M+H]$^+$.

Example 37: 6-(2-ethoxy-3-pyridyl)-3-isopropyl-N-[(6-methoxy-3-pyridyl)methyl]-1-methyl-pyrazolo[3,4-b]pyridin-4-amine

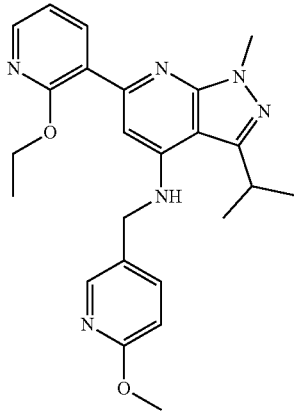 [SMILES: CCOc1ncccc1-c1cc(NCc2ccc(OC)nc2)c2c(C(C)C)nn(C)c2n1]

Prepared in a way similar to example 19 from 4,6-dibromo-3-isopropyl-1-methyl-1H-pyrazolo[3,4-b]pyridine, (6-methoxypyridin-3-yl)methanamine and (2-ethoxypyridin-3-yl)boronic acid.

$^1$H NMR (CDCl$_3$, 400 MHz): δ 8.30 (dd, J=2.0, 7.6 Hz, 1H), 8.22 (d, J=2.0 Hz, 1H), 8.18 (dd, J=2.0, 4.8 Hz, 1H), 7.63 (dd, J=2.4, 8.8 Hz, 1H), 7.02 (dd, J=5.2, 7.4 Hz, 1H), 6.99 (s, 1H), 6.79 (d, J=8.4 Hz, 1H), 5.06 (t, J=4.8 Hz, 1H), 4.51 (d, J=5.2 Hz, 2H), 4.44 (q, J=6.8 Hz, 2H), 4.05 (s, 3H), 3.95 (s, 3H), 3.28-3.21 (m, 1H), 1.44 (d, J=7.2 Hz, 6H), 1.35 (t, J=6.8 Hz, 3H). LC-MS: t$_R$=2.03 minutes (Method A), m/z=433.1 [M+H]$^+$.

Example 38: 6-(2-ethoxy-3-pyridyl)-3-isopropyl-1-methyl-N-[[2-(trifluoromethyl)-3-pyridyl]methyl]pyrazolo[3,4-b]pyridin-4-amine

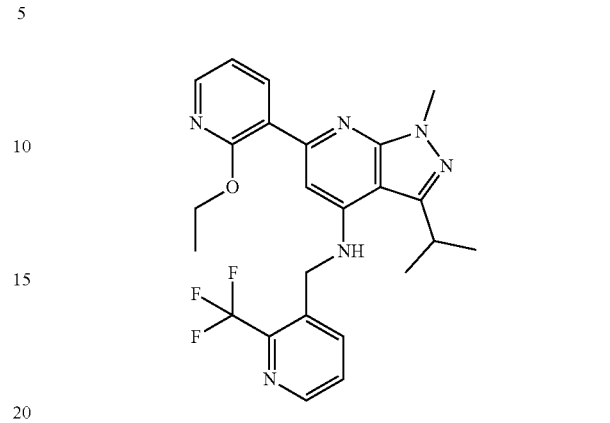

Prepared in a way similar to example 19 from 4,6-dichloro-3-isopropyl-1-methyl-1H-pyrazolo[3,4-b]pyridine, (2-(trifluoromethyl)pyridin-3-yl)methanamine and (2-ethoxypyridin-3-yl)boronic acid.

$^1$H NMR (CDCl$_3$, 400 MHz): δ=8.65 (d, J=4.8 Hz, 1H), 8.29 (dd, J=1.6, 7.6 Hz, 1H), 8.16 (dd, J=2.0, 4.8 Hz, 1H), 7.96 (d, J=7.6 Hz, 1H), 7.49 (dd, J=4.4, 8.0 Hz, 1H), 7.00 (dd, J=5.2, 7.6 Hz, 1H), 6.83 (s, 1H), 5.34 (t, J=6.0 Hz, 1H), 4.90 (d, J=6.0 Hz, 2H), 4.30 (q, J=7.2 Hz, 2H), 4.07 (s, 3H), 3.40-3.28 (m, 1H), 1.51 (d, J=6.4 Hz, 6H), 1.13 (t, J=7.2 Hz, 3H). LC-MS: t$_R$=2.29 minutes (Method A), m/z=471 [M+H]$^+$.

Example 39: 6-(2-ethoxy-3-pyridyl)-3-isopropyl-N-[(4-methoxy-2-pyridyl)methyl]-1-methyl-pyrazolo[3,4-b]pyridin-4-amine

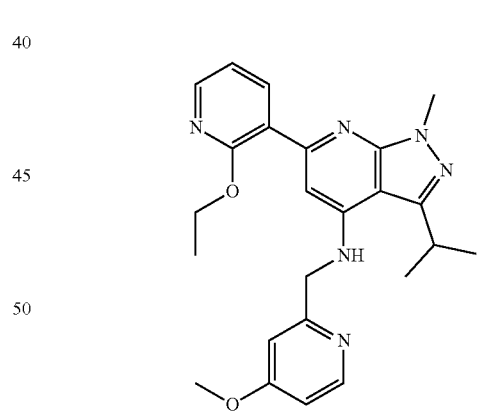

Prepared in a way similar to example 19 from 4,6-dichloro-3-isopropyl-1-methyl-1H-pyrazolo[3,4-b]pyridine, (4-methoxypyridin-2-yl)methanamine and (2-ethoxypyridin-3-yl)boronic acid.

$^1$H NMR (CDCl$_3$, 400 MHz): δ 8.46 (d, J=5.6 Hz, 1H), 8.30 (dd, J=2.0, 7.6 Hz, 1H), 8.18 (dd, J=2.0, 4.8 Hz, 1H), 7.02 (dd, J=4.8, 7.2 Hz, 1H), 6.91 (s, 1H), 6.85 (d, J=1.6 Hz, 1H), 6.79 (d, J=3.2 Hz, 1H), 6.53 (brs, 1H), 4.60 (d, J=4.4 Hz, 2H), 4.46 (q, J=7.2 Hz, 2H), 4.06 (s, 3H), 3.86 (s, 3H), 3.54-3.47 (m, 1H), 1.52 (d, J=6.8 Hz, 6H), 1.40 (t, J=7.2 Hz, 3H). LC-MS: t$_R$=1.58 minutes (Method A), m/z=433.1 [M+H]$^+$.

Example 40: 6-(2-ethoxy-3-pyridyl)-3-isopropyl-1-methyl-N-(2-pyridylmethyl)pyrazolo[3,4-b]pyridin-4-amine

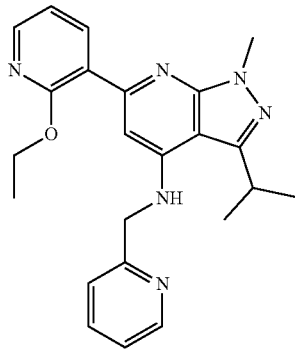 [SMILES: CCOc1ncccc1-c1cc(NCc2ccccn2)c2c(C(C)C)nn(C)c2n1]

Prepared in a way similar to example 1 from 6-(2-ethoxy-3-pyridyl)-3-isopropyl-1-methyl-pyrazolo[3,4-b]pyridin-4-amine and picolinaldehyde.

$^1$H NMR (CDCl$_3$ 400 MHz): δ 8.66-8.65 (m, 1H), 8.32-8.30 (m, 1H), 8.20-8.18 (m, 1H), 7.74-7.70 (m, 1H), 7.36-7.34 (m, 1H), 7.29-7.25 (m, 1H), 7.04-7.01 (m, 1H), 6.94 (s, 1H), 6.62 (brs, 1H), 4.67 (d, J=4.8 Hz, 2H), 4.46 (q, J=6.8 Hz, 2H), 4.06 (s, 3H), 3.56-3.49 (m, 1H), 1.54 (d, J=6.8 Hz, 6H), 1.40 (t, J=7.2 Hz, 3H). LC-MS: $t_R$=1.84 minutes (Method A), m/z=403.1 [M+H]$^+$.

Example 41: 6-(2-ethoxy-3-pyridyl)-3-isopropyl-N-[(6-methoxy-2-pyridyl)methyl]-1-methyl-pyrazolo[3,4-b]pyridin-4-amine

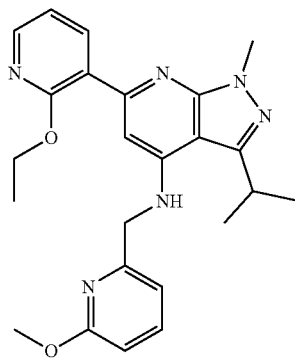 [SMILES: CCOc1ncccc1-c1cc(NCc2cccc(OC)n2)c2c(C(C)C)nn(C)c2n1]

Prepared in a way similar to example 1 from 6-(2-ethoxy-3-pyridyl)-3-isopropyl-1-methyl-pyrazolo[3,4-b]pyridin-4-amine and 6-methoxypicolinaldehyde.

$^1$H NMR (CDCl$_3$ 400 MHz): δ 8.32-8.31 (m, 1H), 8.20-8.19 (m, 1H), 7.62-7.58 (m, 1H), 7.05-7.02 (m, 1H), 6.97 (s, 1H), 6.93-6.91 (m, 1H), 6.72-6.70 (m, 1H), 6.33 (br.s, 1H), 4.60-4.58 (m, 2H), 4.48 (q, J=6.8 Hz, 2H), 4.06 (s, 3H), 4.06 (s, 3H), 3.53-3.49 (m, 1H), 1.51 (d, J=6.8 Hz, 6H), 1.43 (t, J=7.2 Hz, 3H). LC-MS: $t_R$=2.2 minutes (Method A), m/z=433.1 [M+H]$^+$.

Example 42: 6-(2-ethoxy-3-pyridyl)-3-isopropyl-1-methyl-N-[(6-methyl-2-pyridyl)methyl]pyrazolo[3,4-b]pyridin-4-amine

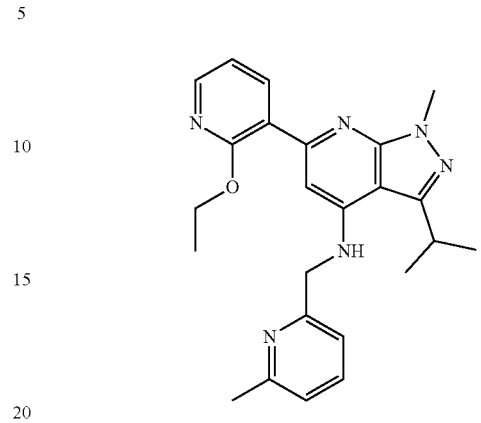

Prepared in a way similar to example 19 from 4,6-dichloro-3-isopropyl-1-methyl-1H-pyrazolo[3,4-b]pyridine, (6-methylpyridin-2-yl)methanamine and (2-ethoxypyridin-3-yl)boronic acid.

$^1$H NMR (CDCl$_3$ 400 MHz): δ 8.32-8.30 (m, 1H), 8.20-8.19 (m, 1H), 7.62 (t, J=7.6 Hz, 1H), 7.15-7.12 (m, 2H), 7.05-7.02 (m, 1H), 6.93 (s, 1H), 6.90 (br.s, 1H), 4.62-4.61 (m, 2H), 4.48 (q, J=6.8 Hz, 2H), 4.06 (s, 3H), 3.61-3.58 (m, 1H), 2.63 (s, 3H), 1.56 (d, J=7.2 Hz, 6H), 1.43 (t, J=7.2 Hz, 3H). LC-MS: $t_R$=1.8 minutes (Method A), m/z=417.1 [M+H]$^+$.

Example 43: 2-(2-ethoxy-3-pyridyl)-5-isopropyl-7-methyl-N-(1,2,4-oxadiazol-3-ylmethyl)imidazo[1,5-b]pyridazin-4-amine

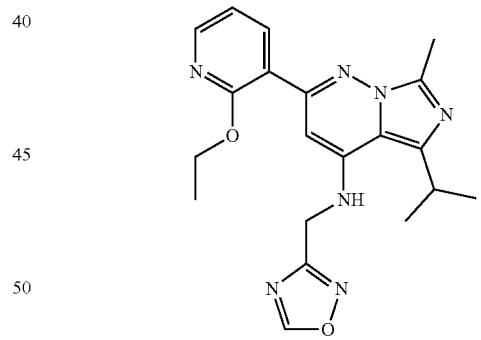

Preparation of 2-((2-chloro-5-isopropyl-7-methyl-imidazo[1,5-b]pyridazin-4-yl)amino)acetonitrile

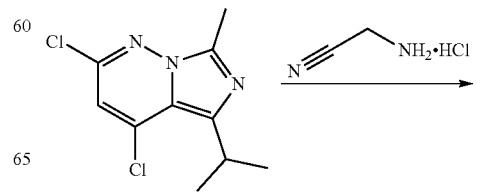

-continued

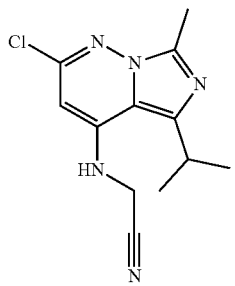

To a solution of 2,4-dichloro-5-isopropyl-7-methylimidazo[1,5-b]pyridazine (430 mg, 1.76 mmol) in NMP (5 mL) was added 2-aminoacetonitrile hydrochloride (326 mg, 3.52 mmol) and triethylamine (535 mg, 5.28 mmol). The mixture was heated at 120° C. for 16 hours. The mixture was cooled to 20° C. and ethyl acetate (20 mL) was added. The organic layer was washed with $H_2O$ (20 mL×2), brine (20 mL), dried over $Na_2SO_4$, filtered and concentrated. The residue was purified by flash chromatography on silica gel (0%~30% ethyl acetate in petroleum ether) to give 2-((2-chloro-5-isopropyl-7-methylimidazo[1,5-b]pyridazin-4-yl)amino)acetonitrile.

Preparation of 2-((2-(2-ethoxypyridin-3-yl)-5-isopropyl-7-methylimidazo[1,5-b]pyridazin-4-yl)amino)acetonitrile

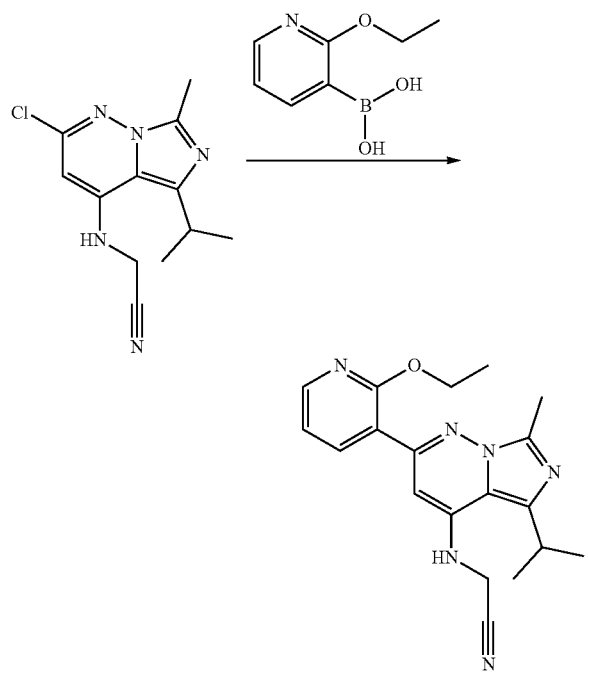

To a solution of 2-((2-chloro-5-isopropyl-7-methylimidazo[1,5-b]pyridazin-4-yl)amino)acetonitrile (50 mg, 0.19 mmol) in dioxane (2 mL) was added (2-ethoxypyridin-3-yl) boronic acid (47 mg, 0.28 mmol), $Cs_2CO_3$ (124 mg, 0.38 mmol) and [1,1'-bis(di-tert-butylphosphino)ferrocene]dichloropalladium(II) (12 mg, 0.02 mol). The mixture was degassed with $N_2$ and heated at 80° C. for 2 hours. The mixture was cooled to 20° C. and extracted with ethyl acetate (20 mL×2). The combined organic phases were washed with $H_2O$ (20 mL), brine (20 mL), dried over $Na_2SO_4$, filtered and concentrated to give the crude product. The residue was purified by flash chromatography on silica gel (10%~50% ethyl acetate in petroleum ether) to give 2-((2-(2-ethoxypyridin-3-yl)-5-isopropyl-7-methylimidazo[1,5-b]pyridazin-4-yl)amino)acetonitrile.

Preparation of 2-((2-(2-ethoxypyridin-3-yl)-5-isopropyl-7-methylimidazo[1,5-b]pyridazin-4-yl)amino)-N'-hydroxyacetimidamide

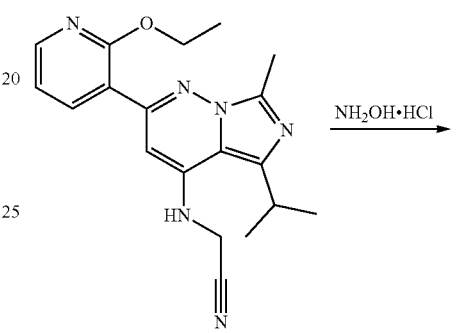

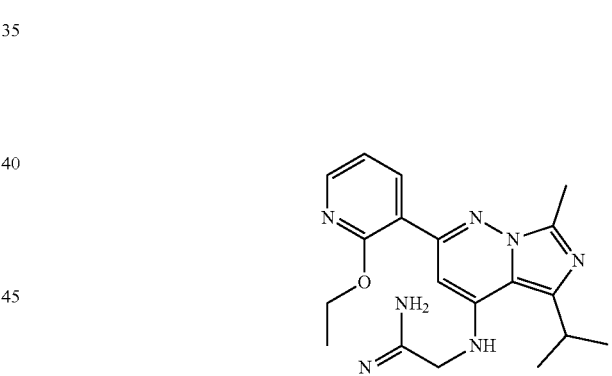

To a solution of 2-((2-(2-ethoxypyridin-3-yl)-5-isopropyl-7-methylimidazo[1,5-b]pyridazin-4-yl)amino)acetonitrile (40 mg, 0.11 mmol) in EtOH (2 mL) was added $NH_2OH \cdot HCl$ (16 mg, 0.23 mmol) and diisopropylethylamine (30 mg, 0.23 mmol). The mixture was heated at 90° C. for 16 hours. The mixture was concentrated and the residue was dissolved in dichloromethane (20 mL) and $NaHCO_3$ (10 mL). The aqueous layer was extracted with dichloromethane (20 mL). The combined organic layers was dried over $Na_2SO_4$, filtered and concentrated. The residue was purified by flash chromatography on silica gel (10%~100% ethyl acetate in petroleum ether) to give 2-((2-(2-ethoxypyridin-3-yl)-5-isopropyl-7-methylimidazo[1,5-b]pyridazin-4-yl)amino)-N-hydroxyacetimidamide.

Preparation of N-((1,2,4-oxadiazol-3-yl)methyl)-2-(2-ethoxypyridin-3-yl)-5-isopropyl-7-methylimidazo[1,5-b]pyridazin-4-amine

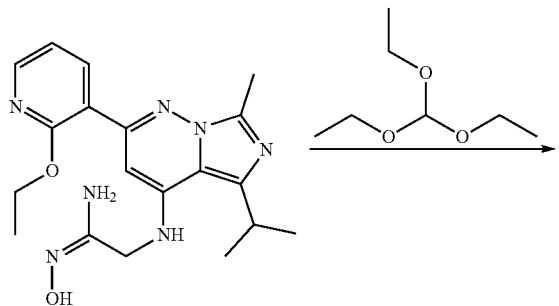

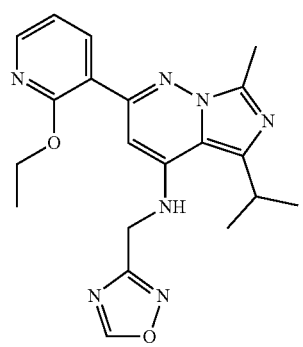 [SMILES: CCOc1ncccc1-c1cc(NCc2ncon2)c2c(C(C)C)nc(C)n2n1]

A solution of 2-((2-(2-ethoxypyridin-3-yl)-5-isopropyl-7-methylimidazo[1,5-b]pyridazin-4-yl)amino)-N-hydroxyacetimidamide (50 mg, 0.13 mmol), triethoxymethane (2 mL, 12.01 mmol) and BF$_3$.Et$_2$O (0.1 mL, 0.8 mmol) was heated at 90° C. for 2 hours. The mixture was concentrated and the residue was dissolved in ethyl acetate (20 mL). The organic layer was washed with saturated aqueous NaHCO$_3$ solution (10 mL), H$_2$O (10 mL), brine (10 mL), dried over Na$_2$SO$_4$, filtered and concentrated. The residue was purified by flash chromatography on silica gel (10%~100% ethyl acetate in petroleum ether). Then the residue was purified by SFC to give N-((1,2,4-oxadiazol-3-yl)methyl)-2-(2-ethoxypyridin-3-yl)-5-isopropyl-7-methylimidazo[1,5-b]pyridazin-4-amine.

$^1$H NMR (CDCl$_3$ 400 MHz): δ 8.78 (s, 1H), 8.23 (dd, J=2.0, 4.2 Hz, 1H), 7.95 (dd, J=1.6, 7.6 Hz, 1H), 7.00 (dd, J=4.2, 7.6 Hz, 1H), 6.17 (s, 1H), 5.65 (br. s, 1H), 4.71 (d, J=4.2 Hz, 2H), 4.48 (q, J=7.2 Hz, 2H), 3.38-3.32 (m, 1H), 2.70 (s, 3H), 1.48 (d, J=6.8 Hz, 6H), 1.42 (t, J=6.8 Hz, 3H). LC-MS: t$_R$=2.09 minutes (Method C), m/z=394 [M+H]$^+$.

Example 44: 2-(2-ethoxy-3-pyridyl)-5-isopropyl-7-methyl-N-[(2-methyltriazol-4-yl)methyl]imidazo[1,5-b]pyridazin-4-amine

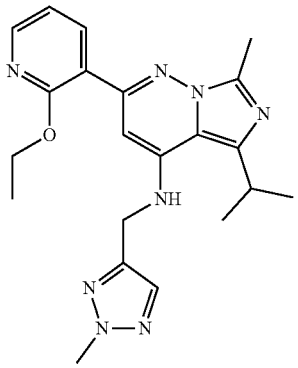

Prepared in a way similar to example 26 from 2-(2-ethoxypyridin-3-yl)-5-isopropyl-N-(4-methoxybenzyl)-7-methylimidazo[1,5-b]pyridazin-4-amine and 4-(bromomethyl)-2-methyl-2H-1,2,3-triazole.

$^1$H NMR (CDCl$_3$ 400 MHz): δ 8.23 (dd, J=4.8, 2.0 Hz, 1H), 8.04 (dd, J=7.6, 2.0 Hz, 1H), 7.58 (s, 1H), 7.01 (dd, J=7.2, 4.8 Hz, 1H), 6.11 (s, 1H), 5.49-5.47 (m, 1H), 4.58 (d, J=5.6 Hz, 2H), 4.46 (q, J=7.2 Hz, 2H), 4.22 (s, 3H), 3.33-3.26 (m, 1H), 2.70 (s, 3H), 1.46 (d, J=7.2 Hz, 6H), 1.38 (t, J=7.2 Hz, 3H). LC-MS: t$_R$=2.05 minutes (Method C), m/z=407.1 [M+H]$^+$.

Example 45: 2-(2-ethoxy-3-pyridyl)-5-isopropyl-7-methyl-N-[(5-methyl-1,3,4-oxadiazol-2-yl)methyl]imidazo[1,5-b]pyridazin-4-amine

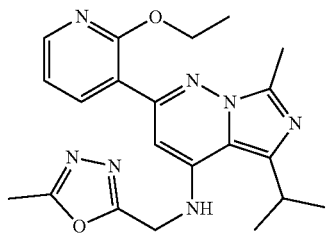 [SMILES: CCOc1ncccc1-c1cc(NCc2nnc(C)o2)c2c(C(C)C)nc(C)n2n1]

Prepared in a way similar to example 19 from 2,4-dichloro-5-isopropyl-7-methylimidazo[1,5-b]pyridazine, (5-methyl-1,3,4-oxadiazol-2-yl)methanamine oxalate and (2-ethoxypyridin-3-yl)boronic acid.

$^1$H NMR (CDCl$_3$ 400 MHz): δ 8.23 (dd, J=4.8, 2.0 Hz, 1H), 8.03 (dd, J=7.2, 2.0 Hz, 1H), 7.02-6.99 (m, 1H), 6.16 (s, 1H), 5.61-5.58 (m, 1H), 4.71 (d, J=5.6 Hz, 2H), 4.48 (q, J=7.2 Hz, 2H), 3.37-3.30 (m, 1H), 2.70 (s, 3H), 2.57 (s, 3H), 1.47 (d, J=6.8 Hz, 6H), 1.41 (t, J=7.2 Hz, 3H). LC-MS: t$_R$=2.05 minutes (Method C), m/z=408 [M+H]$^+$.

Example 46: 2-(2-ethoxy-3-pyridyl)-5-isopropyl-7-methyl-N-[(3-methyl-1,2,4-oxadiazol-5-yl)methyl]imidazo[1,5-b]pyridazin-4-amine

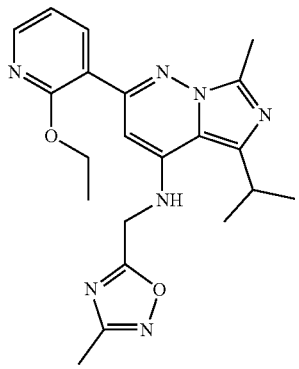 [SMILES: CCOc1ncccc1-c1cc(NCc2nc(C)no2)c2c(C(C)C)nc(C)n2n1]

Preparation of ethyl 2-((2-(2-ethoxypyridin-3-yl)-5-isopropyl-7-methylimidazo[1,5-b]pyridazin-4-yl)(4-methoxybenzyl)amino)acetate

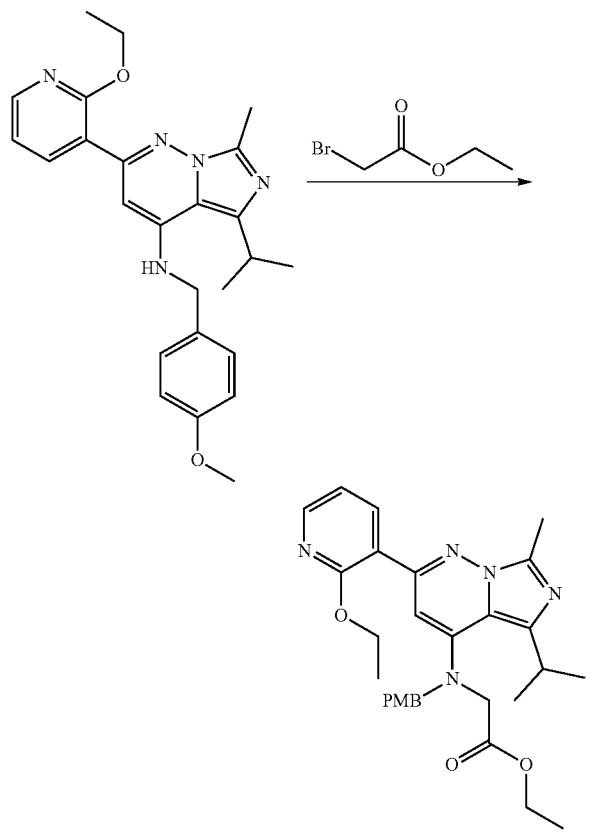

To a solution of 2-(2-ethoxypyridin-3-yl)-5-isopropyl-N-(4-methoxybenzyl)-7-methylimidazo[1,5-b]pyridazin-4-amine (50 mg, 0.12 mmol) in DMSO (2 mL) was added ethyl 2-bromoacetate (39 mg, 0.23 mmol), NaI (35 mg, 0.23 mmol) and t-BuOK (39 mg, 0.35 mmol). The mixture was heated at 100° C. for 16 hours. The mixture was cooled to 20° C. ethyl acetate (20 mL) and H₂O (10 mL) were added. The organic layer was washed with H₂O (10 ml×2), brine (10 mL), dried over Na₂SO₄, filtered and concentrate. The crude was purified by preparative TLC (SiO₂, petroleum ether/ethyl acetate=2/1) to give ethyl 2-((2-(2-ethoxypyridin-3-yl)-5-isopropyl-7-methylimidazo[1,5-b]pyridazin-4-yl)(4-methoxybenzyl)amino)acetate.

Preparation of ethyl 2-(2-ethoxypyridin-3-yl)-5-isopropyl-N-(4-methoxybenzyl)-7-methyl-N-((3-methyl-1,2,4-oxadiazol-5-yl)methyl)imidazo[1,5-b]pyridazin-4-amine

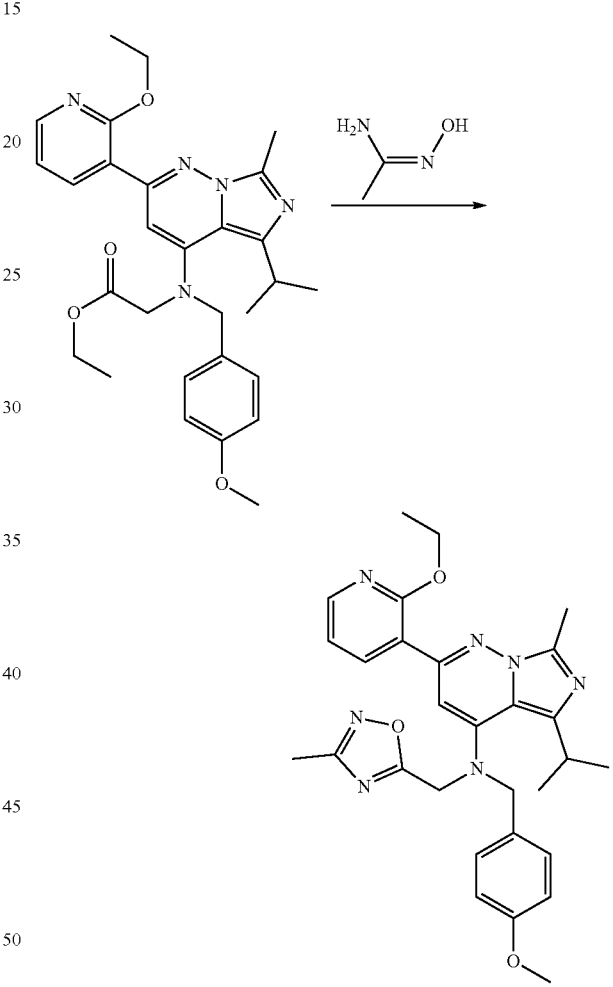

Molecular sieves 4 Å (100 mg) were added to a solution of (Z)—N-hydroxyacetimidamide (17 mg, 0.23 mmol) in THF (3 mL). The mixture was stirred at 20° C. for 30 minutes. Then NaH (9 mg, 0.23 mmol) (60% in mineral oil) was added and the mixture was heated at 50° C. for 30 minutes. Then the mixture was cooled to 20° C. and a solution of ethyl 2-((2-(2-ethoxypyridin-3-yl)-5-isopropyl-7-methylimidazo[1,5-b]pyridazin-4-yl)(4-methoxybenzyl)amino)acetate (40 mg, 0.08 mmol) in THF (2 mL) was added. The mixture was heated at 80° C. for 2 hours. Water (1 mL) was added. The mixture was extracted with ethyl acetate (20 mL×2). The combined organic phases were washed with H₂O (50 mL), brine (50 mL), dried over Na₂SO₄, filtered and concentrated. The residue was purified by preparative TLC (SiO$_2$, petroleum ether/ethyl acetate=2/1) to give 2-(2-ethoxypyridin-3-yl)-5-isopropyl-N-(4-methoxybenzyl)-7-methyl-N-((3-methyl-1,2,4-oxadiazol-5-yl)methyl)imidazo[1,5-b]pyridazin-4-amine.

Preparation of ethyl 2-(2-ethoxypyridin-3-yl)-5-isopropyl-7-methyl-N-((3-methyl-1,2,4-oxadiazol-5-yl)methyl)imidazo[1,5-b]pyridazin-4-amine

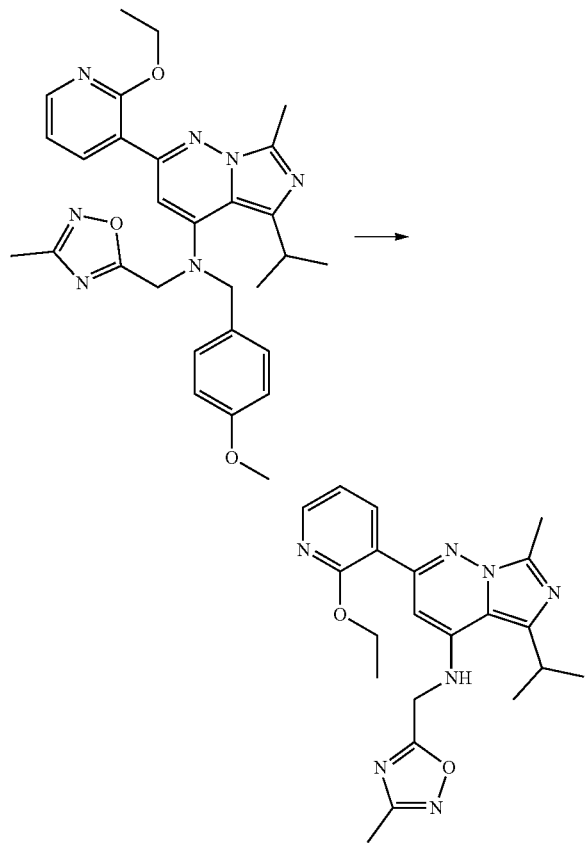

A solution of 2-(2-ethoxypyridin-3-yl)-5-isopropyl-N-(4-methoxybenzyl)-7-methyl-N-((3-methyl-1,2,4-oxadiazol-5-yl)methyl)imidazo[1,5-b]pyridazin-4-amine (40 mg, 0.07 mmol) in TFA (5 mL) was heated at 60° C. for 16 hours. The mixture was concentrated. H$_2$O (2 mL) was added to the residue. The mixture was adjusted to pH=7 by sat.aq.NaHCO$_3$ and extracted with ethyl acetate (10 mL×2). The combined organic phases were washed with H$_2$O (10 mL), brine (10 mL), dried over Na$_2$SO$_4$, filtered and concentrated. The crude was purified by preparative TLC (SiO$_2$, petroleum ether/ethyl acetate=1/1) to give 2-(2-ethoxypyridin-3-yl)-5-isopropyl-7-methyl-N-((3-methyl-1,2,4-oxadiazol-5-yl)methyl)imidazo[1,5-b]pyridazin-4-amine.

$^1$H NMR (CDCl$_3$ 400 MHz): δ 8.24 (dd, J=2.0, 4.8 Hz, 1H), 7.61 (d, J=2.4, 1H), 7.00 (dd, J=4.2, 7.6 Hz, 1H), 6.10 (s, 1H), 5.66-5.63 (m, 1H), 4.72 (d, J=5.6 Hz, 2H), 4.47 (q, J=7.2 Hz, 2H), 3.40-3.33 (m, 1H), 2.72 (s, 3H), 2.44 (s, 3H), 1.50 (d, J=7.2 Hz, 6H), 1.40 (t, J=7.2 Hz, 3H). LC-MS: t$_R$=1.97 minutes (Method C), m/z=408.1 [M+H]$^+$.

Example 47: (−)-2-(2-ethoxy-3-pyridyl)-7-methyl-N-[(1-methylpyrazol-4-yl)methyl]-5-[1-methylpropyl]imidazo[1,5-b]pyridazin-4-amine

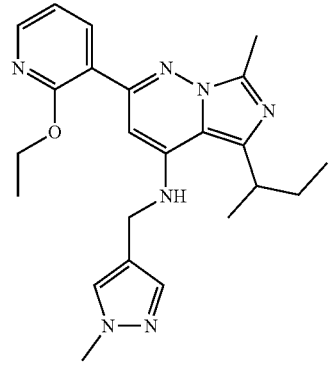 [SMILES: CCOc1ncccc1-c1cc(NCc2cnn(C)c2)c2c(C(C)CC)nc(C)n2n1]

Prepared in a way similar to example 1 from (−)-5-(sec-butyl)-2-(2-ethoxypyridin-3-yl)-N-(4-methoxybenzyl)-7-methylimidazo[1,5-b]pyridazin-4-amine and 1-methyl-1H-pyrazole-4-carbaldehyde.

$^1$H NMR (CDCl$_3$ 400 MHz): δ 8.23 (dd, J=2.0, 5.2 Hz, 1H), 8.06 (dd, J=2.0, 7.2 Hz, 1H), 7.54 (s, 1H), 7.42 (s, 1H), 7.00 (dd, J=5.6, 7.6 Hz, 1H), 6.13 (s, 1H), 5.02-5.00 (m, 1H), 4.46 (q, J=7.2 Hz, 2H), 4.37 (d, J=4.8 Hz, 2H), 3.93 (s, 3H), 2.86-2.80 (m, 1H), 2.70 (s, 3H), 1.92-1.87 (m, 1H), 1.73-1.71 (m, 1H), 1.41-1.37 (m, 6H), 0.87 (t, J=7.2 Hz, 3H). LC-MS: t$_R$=1.76 minutes (Method A), m/z=420.1 [M+H]$^+$. [α]$_D^{20}$-5.6 (c=0.4, MeOH)

Example 48: (+)-2-(2-ethoxy-3-pyridyl)-7-methyl-N-[(1-methylpyrazol-4-yl)methyl]-5-[1-methylpropyl]imidazo[1,5-b]pyridazin-4-amine

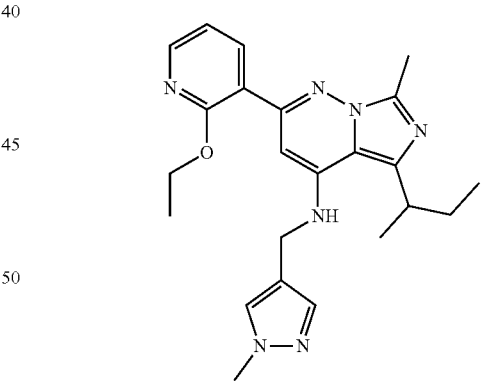

Prepared in a way similar to example 1 from (+)-5-(sec-butyl)-2-(2-ethoxypyridin-3-yl)-N-(4-methoxybenzyl)-7-methylimidazo[1,5-b]pyridazin-4-amine and 1-methyl-1H-pyrazole-4-carbaldehyde.

$^1$H NMR (CDCl$_3$ 400 MHz): δ 8.23 (dd, J=2.0, 5.2 Hz, 1H), 8.06 (dd, J=2.0, 7.2 Hz, 1H), 7.54 (s, 1H), 7.42 (s, 1H), 7.00 (dd, J=4.8, 7.6 Hz, 1H), 6.13 (s, 1H), 5.02-5.00 (m, 1H), 4.46 (q, J=7.2 Hz, 2H), 4.37 (d, J=4.8 Hz, 2H), 3.93 (s, 3H), 2.86-2.80 (m, 1H), 2.70 (s, 3H), 1.92-1.89 (m, 1H), 1.73-1.69 (m, 1H), 1.41-1.37 (m, 6H), 0.87 (t, J=7.2 Hz, 3H). LC-MS: t$_R$=1.76 minutes (Method A), m/z=420.1 [M+H]$^+$. [α]$_D^{20}$+6.0 (c=0.4, MeOH)

Example 49: (−)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine

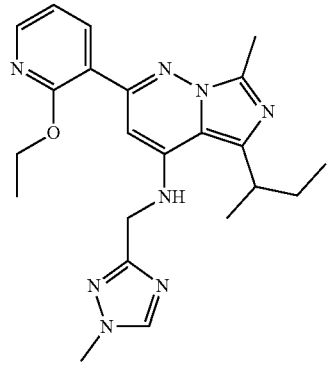 [SMILES: CCOc1ncccc1-c1cc(NCc2ncn(C)n2)c2c(C(C)CC)nc(C)n2n1]

Prepared in a way similar to example 26 from (−)-5-(sec-butyl)-2-(2-ethoxypyridin-3-yl)-N-(4-methoxybenzyl)-7-methylimidazo[1,5-b]pyridazin-4-amine and 3-(chloromethyl)-1-methyl-1H-1,2,4-triazole.

$^1$H NMR (CDCl$_3$ 400 MHz): δ 8.23 (dd, J=2.0, 5.2 Hz, 1H), 8.07-8.05 (m, 2H), 7.00 (dd, J=4.8, 7.2 Hz, 1H), 6.13 (s, 1H), 5.95 (brs, 1H), 4.56 (d, J=4.4 Hz, 2H), 4.47 (q, J=7.2 Hz, 2H), 3.95 (s, 3H), 3.13-3.07 (m, 1H), 2.71 (s, 3H), 1.98-1.93 (m, 1H), 1.79-1.75 (m, 1H), 1.48-1.42 (m, 6H), 0.97 (t, J=7.2 Hz, 3H). LC-MS: t$_R$=1.89 minutes (Method C), m/z=421.1 [M+H]$^+$. [α]$_D^{20}$−2.2 (c=0.5, CHCl$_3$)

Example 50: (+)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine

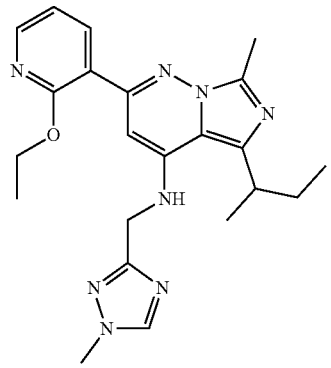 [SMILES: CCOc1ncccc1-c1cc(NCc2ncn(C)n2)c2c(C(C)CC)nc(C)n2n1]

Prepared in a way similar to example 26 from (+)-5-(sec-butyl)-2-(2-ethoxypyridin-3-yl)-N-(4-methoxybenzyl)-7-methylimidazo[1,5-b]pyridazin-4-amine and 3-(chloromethyl)-1-methyl-1H-1,2,4-triazole.

$^1$H NMR (CDCl$_3$ 400 MHz): δ 8.23 (dd, J=2.0, 5.2 Hz, 1H), 8.08-8.05 (m, 2H), 7.01 (dd, J=4.8, 7.2 Hz, 1H), 6.13 (s, 1H), 5.95 (brs, 1H), 4.56 (d, J=4.4 Hz, 2H), 4.47 (q, J=7.2 Hz, 2H), 3.95 (s, 3H), 3.13-3.07 (m, 1H), 2.71 (s, 3H), 1.98-1.95 (m, 1H), 1.79-1.75 (m, 1H), 1.48-1.42 (m, 6H), 0.97 (t, J=7.2 Hz, 3H). LC-MS: t$_R$=1.89 minutes (Method C), m/z=421.1 [M+H]$^+$. [α]$_D^{20}$+4.6 (c=0.5, CHCl$_3$)

Example 51: (+)-2-(2-ethoxy-3-pyridyl)-7-methyl-N-(1H-pyrazol-3-ylmethyl)-5-[1-methylpropyl]imidazo[1,5-b]pyridazin-4-amine

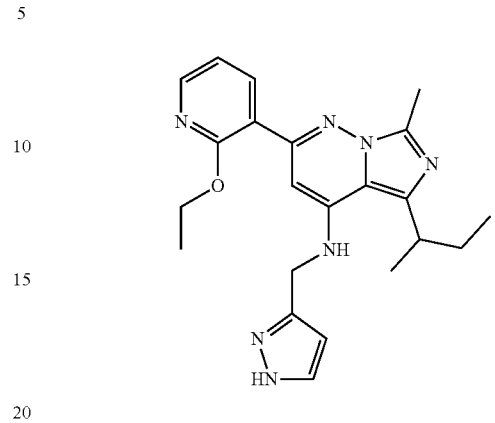

Prepared in a way similar to example 1 from (+)-5-(sec-butyl)-2-(2-ethoxypyridin-3-yl)-N-(4-methoxybenzyl)-7-methylimidazo[1,5-b]pyridazin-4-amine and 1H-pyrazole-3-carbaldehyde.

$^1$H NMR (CDCl$_3$ 400 MHz): δ 8.23 (dd, J=2.0, 4.8 Hz, 1H), 8.05 (dd, J=2.0, 7.6 Hz, 1H), 7.61 (d, J=2.4 Hz, 1H), 7.00 (dd, J=4.8, 7.2 Hz, 1H), 6.35 (d, J=2.4 Hz, 1H), 6.14 (s, 1H), 5.72 (brs, 1H), 4.56 (d, J=4.8 Hz, 2H), 4.47 (q, J=7.2 Hz, 2H), 3.04-2.99 (m, 1H), 2.72 (s, 3H), 1.95-1.93 (m, 1H), 1.77-1.72 (m, 1H), 1.44 (d, J=6.8 Hz, 3H), 1.41 (t, J=7.2 Hz, 3H), 0.92 (t, J=7.2 Hz, 3H). LC-MS: t$_R$=1.71 minutes (Method A), m/z=406.1 [M+H]$^+$. [α]$_D^{20}$+3.3 (c=0.4, MeOH)

Example 52: (−)-2-(2-ethoxy-3-pyridyl)-7-methyl-N-(1H-pyrazol-3-ylmethyl)-5-[1-methylpropyl]imidazo[1,5-b]pyridazin-4-amine

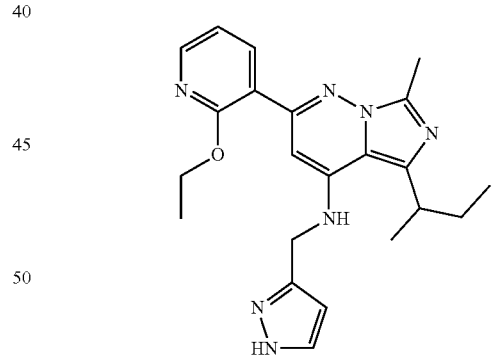

Prepared in a way similar to example 1 from (−)-5-(sec-butyl)-2-(2-ethoxypyridin-3-yl)-N-(4-methoxybenzyl)-7-methylimidazo[1,5-b]pyridazin-4-amine and 1H-pyrazole-3-carbaldehyde.

$^1$H NMR (CDCl$_3$ 400 MHz): δ 8.23 (dd, J=2.0, 4.8 Hz, 1H), 8.05 (dd, J=2.0, 7.6 Hz, 1H), 7.61 (d, J=2.4 Hz, 1H), 7.00 (dd, J=4.8, 7.2 Hz, 1H), 6.35 (d, J=2.4 Hz, 1H), 6.14 (s, 1H), 5.72 (brs, 1H), 4.56 (d, J=4.8 Hz, 2H), 4.47 (q, J=7.2 Hz, 2H), 3.04-2.97 (m, 1H), 2.71 (s, 3H), 1.95-1.93 (m, 1H), 1.77-1.72 (m, 1H), 1.44 (d, J=6.8 Hz, 3H), 1.41 (t, J=7.2 Hz, 3H), 0.92 (t, J=7.2 Hz, 3H). LC-MS: t$_R$=1.71 minutes (Method A), m/z=406.1 [M+H]$^+$. [α]$_D^{20}$−3.4 (c=0.4, MeOH)

Example 53: (+)-2-(2-ethoxy-3-pyridyl)-N-[(2-methoxy-4-pyridyl)methyl]-7-methyl-5-[1-methylpropyl]imidazo[1,5-b]pyridazin-4-amine

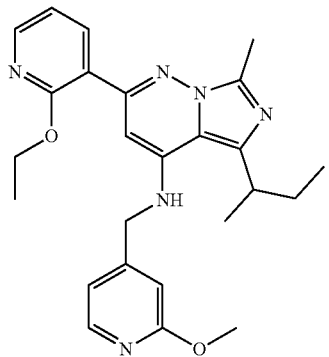 [SMILES: CCOc1ncccc1-c1cc(NCc2ccnc(OC)c2)c2c(C(C)CC)nc(C)n2n1]

Prepared in a way similar to example 26 from (+)-5-(sec-butyl)-2-(2-ethoxypyridin-3-yl)-N-(4-methoxybenzyl)-7-methylimidazo[1,5-b]pyridazin-4-amine and 4-(chloromethyl)-2-methoxy-pyridine.

$^1$H NMR (CDCl$_3$ 400 MHz): δ 8.20 (dd, J=2.0, 5.2 Hz, 1H), 8.16 (d, J=5.2 Hz, 1H), 8.02 (dd, J=2.0, 7.6 Hz, 1H), 6.97 (dd, J=5.2, 7.6 Hz, 1H), 6.87 (dd, J=1.6, 5.2 Hz, 1H), 6.74 (d, J=1.6 Hz, 1H), 5.96 (s, 1H), 5.35 (brt, J=6.0 Hz, 1H), 4.53 (d, J=6.0 Hz, 2H), 4.33 (q, J=7.2 Hz, 2H), 3.94 (s, 3H), 2.98-2.93 (m, 1H), 2.71 (s, 3H), 1.99-1.94 (m, 1H), 1.80-1.76 (m, 1H), 1.46 (d, J=6.8 Hz, 3H), 1.21 (t, J=7.2 Hz, 3H), 0.94 (t, J=7.2 Hz, 3H). LC-MS: $t_R$=1.88 minutes (Method A), m/z=447.1 [M+H]$^+$. [α]$_D^{20}$+4.0 (C=0.6, CHCl$_3$)

Example 54: (−)-2-(2-ethoxy-3-pyridyl)-N-[(2-methoxy-4-pyridyl)methyl]-7-methyl-5-[1-methylpropyl]imidazo[1,5-b]pyridazin-4-amine

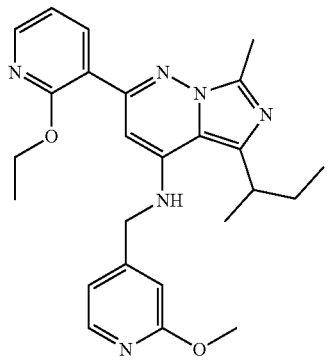 [SMILES: CCOc1ncccc1-c1cc(NCc2ccnc(OC)c2)c2c(C(C)CC)nc(C)n2n1]

Prepared in a way similar to example 26 from (−)-5-(sec-butyl)-2-(2-ethoxypyridin-3-yl)-N-(4-methoxybenzyl)-7-methylimidazo[1,5-b]pyridazin-4-amine and 4-(chloromethyl)-2-methoxy-pyridine.

$^1$H NMR (CDCl$_3$ 400 MHz): δ 8.20 (dd, J=2.0, 5.2 Hz, 1H), 8.16 (d, J=5.2 Hz, 1H), 8.02 (dd, J=2.0, 7.6 Hz, 1H), 6.97 (dd, J=5.2, 7.6 Hz, 1H), 6.87 (dd, J=1.6, 5.2 Hz, 1H), 6.74 (d, J=1.6 Hz, 1H), 5.96 (s, 1H), 5.35 (brt, J=6.0 Hz, 1H), 4.53 (d, J=6.0 Hz, 2H), 4.33 (q, J=7.2 Hz, 2H), 3.94 (s, 3H), 3.00-2.91 (m, 1H), 2.71 (s, 3H), 2.01-1.94 (m, 1H), 1.80-1.78 (m, 1H), 1.46 (d, J=6.8 Hz, 3H), 1.21 (t, J=7.2 Hz, 3H), 0.94 (t, J=7.2 Hz, 3H). LC-MS: $t_R$=1.88 minutes (Method A), m/z=447.1 [M+H]$^+$. [t]$_D^{20}$−4.3 (c=0.6, CHCl$_3$)

Example 55: 3-isopropyl-6-(2-methoxy-3-pyridyl)-1-methyl-N-[(1-methyl-1,2,4-triazol-3-yl)methyl]pyrazolo[3,4-b]pyridin-4-amine

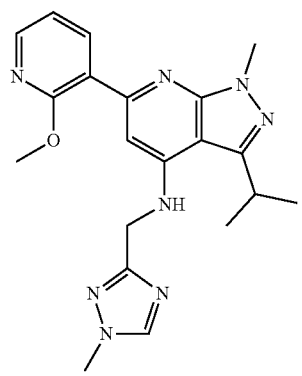 [SMILES: COc1ncccc1-c1cc(NCc2ncn(C)n2)c2c(C(C)C)nn(C)c2n1]

Prepared in a way similar to example 19 from 4,6-dibromo-3-isopropyl-1-methyl-1H-pyrazolo[3,4-b]pyridine, (1-methyl-1H-1,2,4-triazol-3-yl)methanamine and (2-methoxypyridin-3-yl)boronic acid.

$^1$H NMR (CDCl$_3$ 400 MHz): δ 8.23-8.21 (m, 2H), 8.05 (s, 1H), 7.06-7.03 (m, 1H), 6.87 (s, 1H), 5.83 (brs, 1H), 4.63 (d, J=4.8 Hz, 2H), 4.04 (s, 3H), 4.04 (s, 3H), 3.95 (s, 3H), 3.46-3.39 (m, 1H). 1.50 (d, J=6.8 Hz, 6H). LC-MS: $t_R$=1.82 minutes (Method B), m/z=393.1 [M+H]$^+$.

Example 56: 3-(3-isopropyl-1-methyl-4-(((1-methyl-1H-1,2,4-triazol-3-yl)methyl)amino)-1H-pyrazolo[3,4-b]pyridin-6-yl)-1-methyl pyridin-2(1H)-one

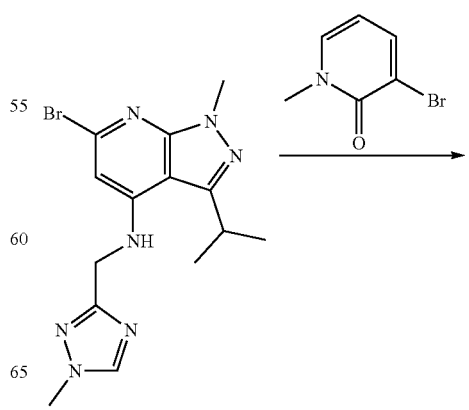

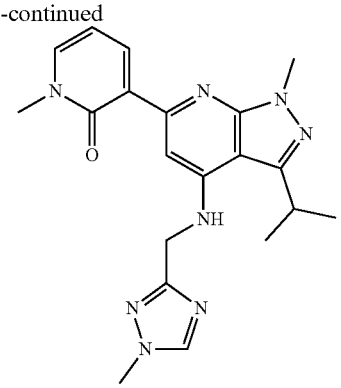

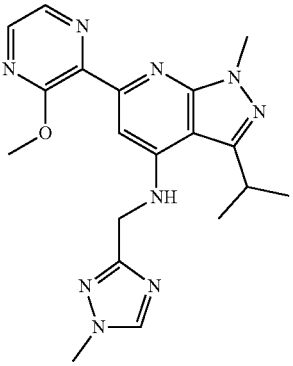

6-Bromo-3-isopropyl-1-methyl-N-[(1-methyl-1,2,4-triazol-3-yl)methyl]pyrazolo[3,4-b]pyridin-4-amine (prepared in a way similar to 6-chloro-3-isopropyl-1-methyl-N-((1-methyl-1H-pyrazol-4-yl)methyl)-1H-pyrazolo[3,4-b]pyridin-4-amine in example 19 from 4,6-dibromo-3-isopropyl-1-methyl-1H-pyrazolo[3,4-b]pyridine and (1-methyl-1H-1,2,4-triazol-3-yl)methanamine) (50 mg, 0.14 mmol), 4,4,5,5-tetramethyl-2-(4,4,5,5-tetramethyl-1,3,2-dioxaborolan-2-yl)-1,3-2-dioxaborolane (70 mg, 0.28 mmol), 3-bromo-1-methyl-pyridin-2-one (52 mg, 0.28 mmol), $Cs_2CO_3$ (112 mg, 0.34 mmol) and Pd(dppf)$Cl_2$ (25 mg, 0.034 mmol) were taken up into a microwave tube in dioxane (1 mL) and $H_2O$ (0.25 mL). The sealed tube was heated at 100° C. for 1 hour under microwave. The reaction mixture was partitioned between ethyl acetate (20 mL) and $H_2O$ (20 mL). The organic phase was separated, washed with $H_2O$ (10 mL×2), dried over anhydrous $Na_2SO_4$, filtered and concentrated under reduced pressure to give a residue. The residue was purified by flash silica gel chromatography (SiO$_2$, Dichloromethane: Methanol=1/0 to 10:1) and lyophilized to give 3-[3-isopropyl-1-methyl-4-[(1-methyl-1,2,4-triazol-3-yl)methylamino]pyrazolo[3,4-b]pyridin-6-yl]-1-methyl-pyridin-2-one.

$^1$H NMR (CDCl$_3$ 400 MHz): δ 8.45 (dd, J=2.0, 6.8 Hz, 1H), 8.03 (s, 1H), 7.59 (s, 1H), 7.41 (dd, J=2.0, 6.8 Hz, 1H), 6.36 (d, J=6.8, 6.8 Hz, 1H), 5.80 (brs, 1H), 4.68 (d, J=4.8 Hz, 2H), 4.03 (s, 3H), 3.93 (s, 3H), 3.67 (s, 3H), 3.44-3.36 (m, 1H), 1.48 (d, J=6.8 Hz, 6H). LC-MS: t$_R$=1.57 minutes (Method B), m/z=393.1 [M+H]$^+$.

Example 57: 3-isopropyl-6-(3-methoxypyrazin-2-yl)-1-methyl-N-((1-methyl-1H-1,2,4-triazol-3-yl)methyl)-1H-pyrazolo[3,4-b]pyridin-4-amine

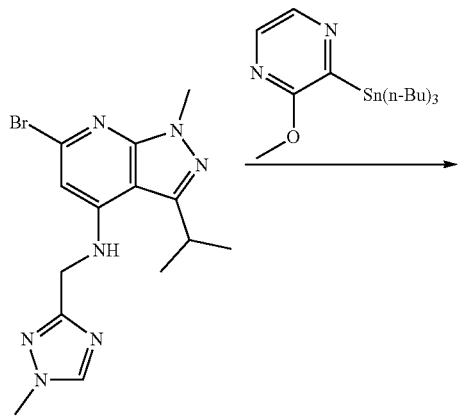

To a solution of 6-bromo-3-isopropyl-1-methyl-N-((1-methyl-1H-1,2,4-triazol-3-yl)methyl)-1H-pyrazolo[3,4-b]pyridin-4-amine (100 mg, 0.27 mmol) in dioxane (2 mL) was added 2-methoxy-3-(tributylstannyl)pyrazine (164 mg, 0.41 mmol), CsF (83 mg, 0.55 mmol), Pd-PEPPSI precatalyst (dichloro[1,3-bis(2,6-di-3-pentylphenyl)imidazol-2-ylidene](3-chloropyridyl)palladium(II)) (11 mg, 0.01 mmol) and 4 Å molecular sieves (50 mg). The mixture was degassed with $N_2$ and heated at 100° C. for 16 hours. The mixture was filtered and the filter cake was washed with 10% MeOH in dichloromethane (20 mL). The filtrate was concentrated. The residue was purified by flash silica gel chromatography (SiO$_2$, 0~10% MeOH/dichloromethane) to give the crude product. The crude product was purified by preparative HPLC to give 3-isopropyl-6-(3-methoxypyrazin-2-yl)-1-methyl-N-((1-methyl-1H-1,2,4-triazol-3-yl)methyl)-1H-pyrazolo[3,4-b]pyridin-4-amine.

$^1$H NMR (CDCl$_3$ 400 MHz): δ 8.32 (d, J=2.4 Hz, 1H), 8.17 (d, J=2.8 Hz, 1H), 8.04 (s, 1H), 6.78 (s, 1H), 5.92-5.90 (m, 1H), 4.62 (d, J=4.8 Hz, 2H), 4.07 (s, 3H), 4.04 (s, 3H), 3.94 (s, 3H), 3.46-3.40 (m, 1H), 1.50 (d, J=6.8 Hz, 6H). LC-MS: t$_R$=1.59 minutes (Method B), m/z=394.1 [M+H]$^+$.

Example 58: 3-isopropyl-1-methyl-6-(2-methyl-3-thienyl)-N-[(1-methyl-1,2,4-triazol-3-yl)methyl]pyrazolo[3,4-b]pyridin-4-amine

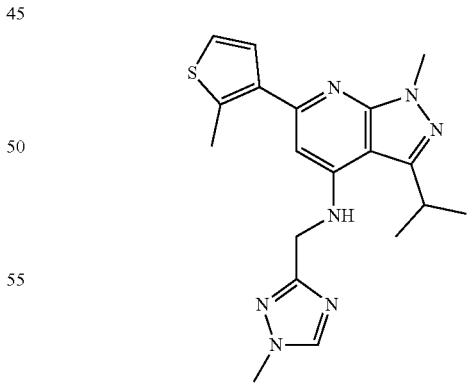

Prepared in a way similar to example 19 from 4,6-dibromo-3-isopropyl-1-methyl-1H-pyrazolo[3,4-b]pyridine, (1-methyl-1H-1,2,4-triazol-3-yl)methanamine and 4,4,5,5-tetramethyl-2-(2-methylthiophen-3-yl)-1,3,2-dioxaborolane.

$^1$H NMR (CDCl$_3$ 400 MHz): δ 8.04 (s, 1H), 7.35 (d, J=5.2 Hz, 1H), 7.11 (d, J=5.2 Hz, 1H), 6.42 (s, 1H), 5.78 (brs, 1H), 4.61 (d, J=5.2 Hz, 2H), 4.03 (s, 3H), 3.94 (s, 3H), 3.44-3.37 (m, 1H), 2.74 (s, 3H), 1.50 (d, J=6.8 Hz, 6H). LC-MS: $t_R$=2.14 minutes (Method B), m/z=382 [M+H]$^+$.

Example 59: 3-isopropyl-1-methyl-N-((1-methyl-1H-1,2,4-triazol-3-yl)methyl)-6-(4-methyloxazol-2-yl)-1H-pyrazolo[3,4-b]pyridin-4-amine

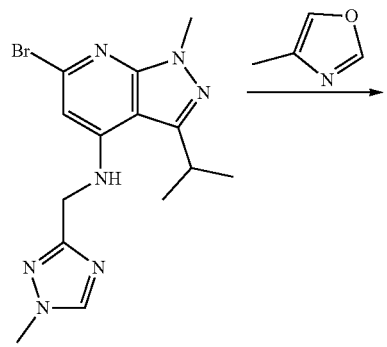

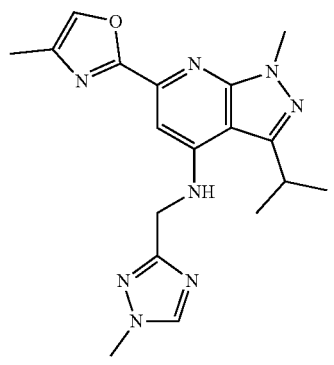

A mixture of 6-bromo-3-isopropyl-1-methyl-N-((1-methyl-1H-1,2,4-triazol-3-yl)methyl)-1H-pyrazolo[3,4-b]pyridin-4-amine (0.1 g, 0.27 mmol), 4-methyloxazole (46 mg, 0.55 mmol), XPHOS-Pd-G3 ((2-dicyclohexylphosphino-2',4',6'-triisopropyl-1,1'-biphenyl)[2-(2'-amino-1,1'-biphenyl)]palladium(II) methanesulfonate) (12 mg, 0.013 mmol), t-BuOK (92 mg, 0.82 mmol) in DMA (4 mL) was stirred at 100° C. for 12 hours under N$_2$. The mixture was concentrated under vacuum and the residue was purified by silica gel chromatography (petroleum ether/ethyl acetate=1/0, 0/1) to afford 3-isopropyl-1-methyl-N-((1-methyl-1H-1,2,4-triazol-3-yl)methyl)-6-(4-methyloxazol-2-yl)-1H-pyrazolo[3,4-b]pyridin-4-amine.

$^1$H NMR (CDCl$_3$; 400 MHz): δ 8.05 (s, 1H), 7.54 (d, J=0.8 Hz, 1H), 7.08 (s, 1H), 5.95 (brs, 1H), 4.68 (d, J=4.8 Hz, 2H), 4.09 (s, 3H), 3.95 (s, 3H), 3.44-3.37 (m, 1H), 2.31 (d, J=0.8 Hz, 3H), 1.49 (d, J=6.8 Hz, 6H). LC-MS: $t_R$=1.73 minutes (Method B), m/z=367.1 [M+H]$^+$.

Example 60: 3-isopropyl-1-methyl-6-(4-methylthiazol-2-yl)-N-[(1-methyl-1,2,4-triazol-3-yl)methyl]pyrazolo[3,4-b]pyridin-4-amine

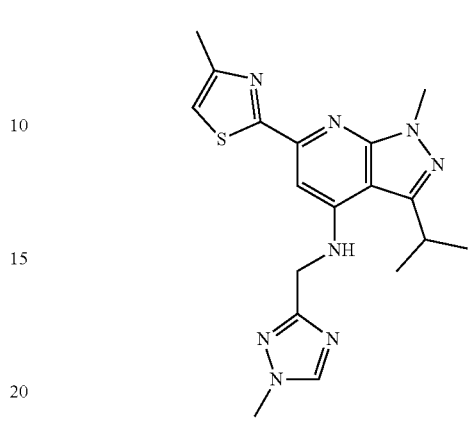

Prepared in a way similar to example 56 from 4,6-dibromo-3-isopropyl-1-methyl-1H-pyrazolo[3,4-b]pyridine, (1-methyl-1H-1,2,4-triazol-3-yl)methanamine and 2-bromo-4-methylthiazole.

$^1$H NMR (CDCl$_3$ 400 MHz): δ 8.05 (s, 1H), 7.17 (s, 1H), 6.99 (d, J=0.8 Hz, 1H), 5.90 (brt, J=4 Hz, 1H), 4.71 (d, J=4.4 Hz, 2H), 4.05 (s, 3H), 3.95 (s, 3H), 3.42-3.39 (m, 1H), 2.56 (d, J=0.8 Hz, 3H), 1.49 (d, J=7.2 Hz, 6H). LC-MS: $t_R$=2.34 minutes (Method C), m/z=383 [M+H]$^+$.

Example 61: 3-isopropyl-1-methyl-N-((1-methyl-1H-1,2,4-triazol-3-yl)methyl)-6-(4-methylthiazol-5-yl)-1H-pyrazolo[3,4-b]pyridin-4-amine

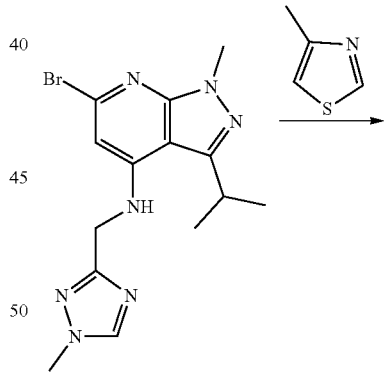

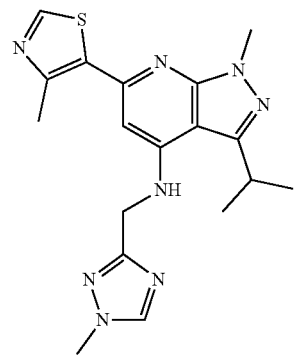 [SMILES: Cc1sccc1-c1cc(NCc2ncn(C)n2)c2c(C(C)C)nn(C)c2n1]

A mixture of 6-bromo-3-isopropyl-1-methyl-N-((1-methyl-1H-1,2,4-triazol-3-yl)methyl)-1H-pyrazolo[3,4-b]pyridin-4-amine (50 mg, 0.14 mmol), 4-methylthiazole (41 mg, 0.41 mmol), dicyclohexyl-[2-(2,6-diisopropoxyphenyl)phenyl]phosphane (6.4 mg, 0.014 mmol), 2,2-dimethylpropanoic acid (5.6 mg, 0.055 mmol), $K_2CO_3$ (57 mg, 0.41 mmol) and $Pd(OAc)_2$ (1.5 mg, 0.007 mmol) in toluene (3 mL) was degassed with $N_2$ and stirred at 110° C. for 12 hours.

The solution was concentrated under vacuum. The residue was purified by flash silica gel chromatography ($SiO_2$, 010% MeOH/dichloromethane). Then the residue was further purified by preparative HPLC to afford 3-isopropyl-1-methyl-N-((1-methyl-1H-1,2,4-triazol-3-yl)methyl)-6-(4-methylthiazol-5-yl)-1H-pyrazolo[3,4-b]pyridin-4-amine.

$^1$H NMR (CDCl$_3$ 400 MHz): δ 8.71 (s, 1H), 8.04 (s, 1H), 6.51 (s, 1H), 5.87-5.84 (brt, J=5.2 Hz, 1H), 4.63 (d, J=4.8 Hz, 2H), 4.02 (s, 3H), 3.94 (s, 3H), 3.43-3.36 (m, 1H), 2.79 (s, 3H), 1.49 (d, J=6.8 Hz, 6H). LC-MS: $t_R$=1.88 minutes (Method C), m/z=383 [M+H]$^+$.

Example 62: 3-isopropyl-1-methyl-6-(5-methylthiazol-2-yl)-N-[(1-methyl-1,2,4-triazol-3-yl)methyl]pyrazolo[3,4-b]pyridin-4-amine

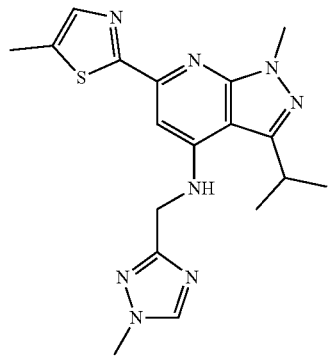 [SMILES: Cc1cnc(-c2cc(NCc3ncn(C)n3)c3c(C(C)C)nn(C)c3n2)s1]

Prepared in a way similar to example 57 from 4,6-dibromo-3-isopropyl-1-methyl-1H-pyrazolo[3,4-b]pyridine, (1-methyl-1H-1,2,4-triazol-3-yl)methanamine and 5-methyl-2-(tributylstannyl)thiazole.

$^1$H NMR (CDCl$_3$ 400 MHz): δ 8.04 (s, 1H), 7.57 (s, 1H), 7.13 (s, 1H), 5.88-5.87 (m, 1H), 4.68 (d, J=4.8 Hz, 2H), 4.04 (s, 3H), 3.94 (s, 3H), 3.43-3.36 (m, 1H), 2.54 (s, 3H), 1.48 (d, J=6.8 Hz, 6H). LC-MS: $t_R$=2.35 minutes (Method C), m/z=383 [M+H]$^+$.

Example 63: 3-isopropyl-1-methyl-N-[(1-methyl-1,2,4-triazol-3-yl)methyl]-6-phenyl-pyrazolo[3,4-b]pyridin-4-amine

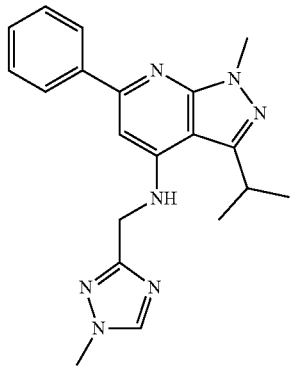 [SMILES: CC(C)c1nn(C)c2nc(-c3ccccc3)cc(NCc3ncn(C)n3)c12]

Prepared in a way similar to example 19 from 4,6-dibromo-3-isopropyl-1-methyl-1H-pyrazolo[3,4-b]pyridine, (1-methyl-1H-1,2,4-triazol-3-yl)methanamine and phenylboronic acid.

$^1$H NMR (CDCl$_3$ 400 MHz): δ 8.08-8.04 (m, 3H), 7.51-7.40 (m, 3H), 6.69 (s, 1H), 5.82-5.79 (m, 1H), 4.66 (d, J=5.2 Hz, 2H), 4.07 (s, 3H), 3.94 (s, 3H), 3.45-3.38 (m, 1H), 1.50 (d, J=6.8 Hz, 6H). LC-MS: $t_R$=1.77 minutes (Method C), m/z=362.1 [M+H]$^+$.

Example 64: 3-isopropyl-6-(4-methoxypyrimidin-5-yl)-1-methyl-N-[(1-methyl-1,2,4-triazol-3-yl)methyl]pyrazolo[3,4-b]pyridin-4-amine

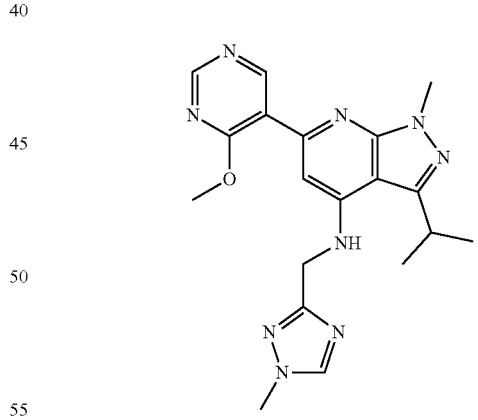

Prepared in a way similar to example 56 from 4,6-dibromo-3-isopropyl-1-methyl-1H-pyrazolo[3,4-b]pyridine, (1-methyl-1H-1,2,4-triazol-3-yl)methanamine and 5-bromo-4-methoxypyrimidine.

$^1$H NMR (CDCl$_3$ 400 MHz): δ 9.08 (s, 1H), 8.82 (s, 1H), 8.05 (s, 1H), 6.81 (s, 1H), 5.88-5.87 (m, 1H), 4.62 (d, J=5.2 Hz, 2H), 4.11 (s, 3H), 4.04 (s, 3H), 3.95 (s, 3H), 3.45-3.38 (m, 1H), 1.50 (d, J=7.2 Hz, 6H). LC-MS: $t_R$=1.65 minutes (Method B), m/z=394 [M+H]$^+$.

Example 65: 3-isopropyl-1-methyl-N-[(1-methyl-1,2,4-triazol-3-yl)methyl]-6-(2-thienyl)pyrazolo[3,4-b]pyridin-4-amine

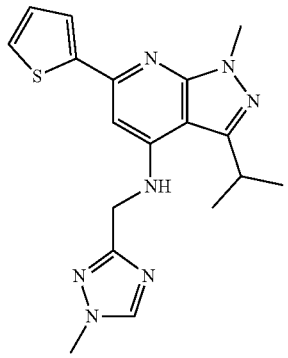 [SMILES: CC(C)c1nn(C)c2nc(-c3cccs3)cc(NCc3ncn(C)n3)c12]

Prepared in a way similar to example 57 from 4,6-dibromo-3-isopropyl-1-methyl-1H-pyrazolo[3,4-b]pyridine, (1-methyl-1H-1,2,4-triazol-3-yl)methanamine and tributyl(thiophen-2-yl)stannane.

$^1$H NMR (CDCl$_3$ 400 MHz): δ 8.04 (s, 1H), 7.67-7.66 (m, 1H), 7.39-7.37 (m, 1H), 7.13-7.11 (m, 1H), 6.65 (s, 1H), 5.79-5.77 (m, 1H), 4.64 (d, J=5.2 Hz, 2H), 4.03 (s, 3H), 3.94 (s, 3H), 3.41-3.35 (m, 1H), 1.48 (d, J=6.8 Hz, 6H). LC-MS: t$_R$=2.05 minutes (Method C), m/z=368 [M+H]$^+$.

Example 66: 6-(3-ethoxypyridazin-4-yl)-3-isopropyl-1-methyl-N-[(1-methyl-1,2,4-triazol-3-yl)methyl]pyrazolo[3,4-b]pyridin-4-amine

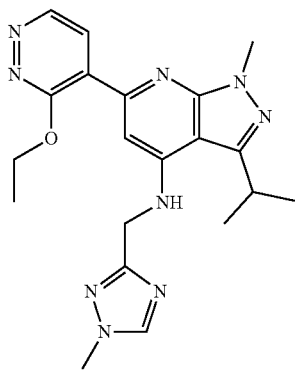 [SMILES: CCOc1nnccc1-c1cc(NCc2ncn(C)n2)c2c(C(C)C)nn(C)c2n1]

Prepared in a way similar to example 57 from 4,6-dibromo-3-isopropyl-1-methyl-1H-pyrazolo[3,4-b]pyridine, (1-methyl-1H-1,2,4-triazol-3-yl)methanamine and 3-ethoxy-4-(tributylstannyl)pyridazine.

$^1$H NMR (CDCl$_3$ 400 MHz): δ 8.96 (d, J=4.8 Hz, 1H), 8.16 (d, J=4.8 Hz, 1H), 8.05 (s, 1H), 7.15 (s, 1H), 5.92-5.90 (m, 1H), 4.75 (q, J=6.8 Hz, 2H), 4.63 (d, J=4.4 Hz, 2H), 4.05 (s, 3H), 3.95 (s, 3H), 3.44-3.40 (m, 1H), 1.55 (t, J=7.2 Hz, 3H), 1.50 (d, J=7.2 Hz, 6H) LC-MS: t$_R$=1.74 minutes (Method B), m/z=408.1 [M+H]$^+$.

Example 67: 3-isopropyl-1-methyl-N-[(1-methyl-1,2,4-triazol-3-yl)methyl]-6-(3-propoxypyridazin-4-yl)pyrazolo[3,4-b]pyridin-4-amine

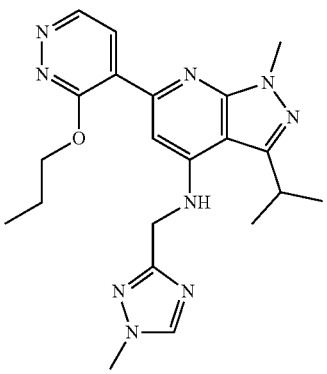 [SMILES: CCCOc1nnccc1-c1cc(NCc2ncn(C)n2)c2c(C(C)C)nn(C)c2n1]

Prepared in a way similar to example 57 from 4,6-dibromo-3-isopropyl-1-methyl-1H-pyrazolo[3,4-b]pyridine, (1-methyl-1H-1,2,4-triazol-3-yl)methanamine and 3-ethoxy-4-(tributylstannyl)pyridazine.

$^1$H NMR (CDCl$_3$ 400 MHz): δ 8.96 (d, J=4.8 Hz, 1H), 8.14 (d, J=4.8 Hz, 1H), 8.05 (s, 1H), 7.11 (s, 1H), 5.91 (br t, J=4.4 Hz, 1H), 4.65-4.61 (m, 4H), 4.04 (s, 3H), 3.94 (s, 3H), 3.45-3.38 (m, 1H), 1.99-1.90 (m, 2H), 1.49 (d, J=6.8 Hz, 6H), 1.10 (t, J=7.2 Hz, 3H) LC-MS: t$_R$=1.88 minutes (Method E), m/z=422.1 [M+H]$^+$.

Example 68: 6-(3-ethoxy-4-pyridyl)-3-isopropyl-1-methyl-N-[(1-methyl-1,2,4-triazol-3-yl)methyl]pyrazolo[3,4-b]pyridin-4-amine

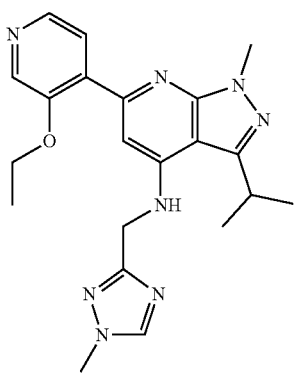

Prepared in a way similar to example 19 from 4,6-dibromo-3-isopropyl-1-methyl-1H-pyrazolo[3,4-b]pyridine, (1-methyl-1H-1,2,4-triazol-3-yl)methanamine and 3-ethoxy-4-(4,4,5,5-tetra methyl-1,3,2-dioxaborolan-2-yl)pyridine.

$^1$H NMR (CDCl$_3$ 400 MHz): δ 8.42-8.35 (m, 2H), 8.05 (s, 1H), 7.91 (d, J=4.0 Hz, 1H), 6.97 (s, 1H), 5.87 (br t, J=4.8 Hz, 1H), 4.61 (d, J=4.8 Hz, 2H), 4.24 (q, J=6.8 Hz, 2H), 4.06 (s, 3H), 3.95 (s, 3H), 3.45-3.39 (m, 1H), 1.52-1.46 (m, 9H) LC-MS: t$_R$=1.64 minutes (Method E), m/z=407.1 [M+H]$^+$.

Example 69: 2-(3-ethoxypyridazin-4-yl)-5-isopropyl-7-methyl-N-[(1-methylpyrazol-4-yl)methyl]imidazo[1,5-b]pyridazin-4-amine

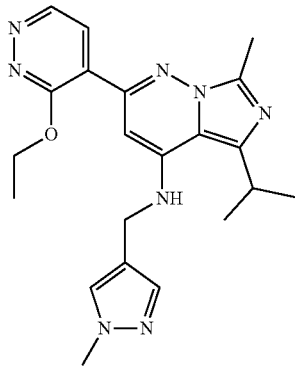 [SMILES: CCOc1nnccc1-c1cc(NCc2cnn(C)c2)c2c(C(C)C)nc(C)n2n1]

Prepared in a way similar to example 57 from 2,4-dichloro-5-isopropyl-7-methylimidazo[1,5-b]pyridazine, (1-methyl-1H-pyrazol-4-yl)methanamine and 3-ethoxy-4-(tributylstannyl)pyridazine.

$^1$H NMR (CDCl$_3$ 400 MHz): δ 8.97 (d, J=4.8 Hz, 1H), 7.87 (d, J=4.8 Hz, 1H), 7.55 (s, 1H), 7.43 (s, 1H), 6.18 (s, 1H), 5.14 (t, J=4.8 Hz, 1H), 4.73 (q, J=6.8 Hz, 2H), 4.40 (d, J=4.8 Hz, 2H), 3.94 (s, 3H), 3.21-3.14 (m, 1H), 2.71 (s, 3H), 1.47 (t, J=6.8 Hz, 3H), 1.44 (d, J=6.4 Hz, 6H) LC-MS: t$_R$=1.64 minutes (Method E), m/z=407.1 [M+H]$^+$.

Example 70: 2-(3-ethoxy-4-pyridyl)-5-isopropyl-7-methyl-N-[(1-methylpyrazol-4-yl)methyl]imidazo[1,5-b]pyridazin-4-amine

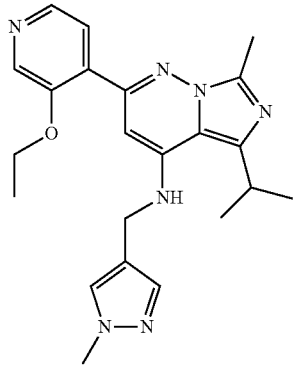 [SMILES: CCOc1cnccc1-c1cc(NCc2cnn(C)c2)c2c(C(C)C)nc(C)n2n1]

Prepared in a way similar to example 19 from 2,4-dichloro-5-isopropyl-7-methylimidazo[1,5-b]pyridazine, (1-methyl-1H-pyrazol-4-yl)methanamine and 3-ethoxy-4-(4,4,5,5-tetramethyl-1,3,2-dioxaborolan-2-yl)pyridine.

$^1$H NMR (CDCl$_3$ 400 MHz): δ 8.41 (s, 1H), 8.36 (d, J=4.8 Hz, 1H), 7.64 (d, J=4.8 Hz, 1H), 7.54 (s, 1H), 7.42 (s, 1H), 6.07 (s, 1H), 5.07 (brs, 1H), 4.37 (d, J=5.2 Hz, 2H), 4.21 (q, J=6.8 Hz, 2H), 3.93 (s, 3H), 3.21-3.14 (m, 1H), 2.71 (s, 3H), 1.42 (d, J=6.8 Hz, 6H), 1.41 (t, J=6.8 Hz, 3H) LC-MS: t$_R$=1.49 minutes (Method E), m/z=406.1 [M+H]$^+$.

Example 71: 5-isopropyl-7-methyl-N-[(1-methylpyrazol-4-yl)methyl]-2-(2-propoxy-3-pyridyl)imidazo[1,5-b]pyridazin-4-amine

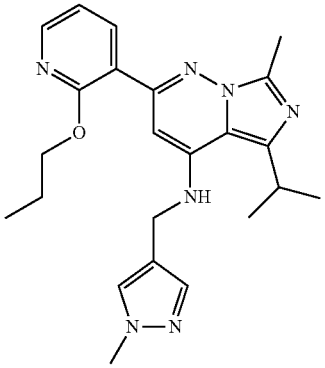 [SMILES: CCCOc1ncccc1-c1cc(NCc2cnn(C)c2)c2c(C(C)C)nc(C)n2n1]

Prepared in a way similar to example 19 from 2,4-dichloro-5-isopropyl-7-methylimidazo[1,5-b]pyridazine, (1-methyl-1H-pyrazol-4-yl)methanamine and 2-propoxy-3-(4,4,5,5-tetramethyl-1,3,2-dioxaborolan-2-yl)pyridine.

$^1$H NMR (CDCl$_3$ 400 MHz): δ 8.23 (dd, J=2.0, 5.2 Hz, 1H), 8.05 (dd, J=2.0, 7.2 Hz, 1H), 7.54 (s, 1H), 7.42 (s, 1H), 7.28 (dd, J=4.8, 7.2 Hz, 1H), 6.12 (s, 1H), 4.99 (brs, 1H), 4.37 (d, J=6.4 Hz, 2H), 4.36 (t, J=7.2 Hz, 2H), 3.93 (s, 3H), 3.20-3.14 (m, 1H), 2.70 (s, 3H), 1.84-1.75 (m, 2H), 1.42 (d, J=6.8 Hz, 6H), 1.04 (t, J=7.2 Hz, 3H) LC-MS: t$_R$=1.83 minutes (Method F), m/z=420.1 [M+H]$^+$.

Example 72: 5-isopropyl-7-methyl-N-[(1-methyl-1,2,4-triazol-3-yl)methyl]-2-(2-propoxy-3-pyridyl)imidazo[1,5-b]pyridazin-4-amine

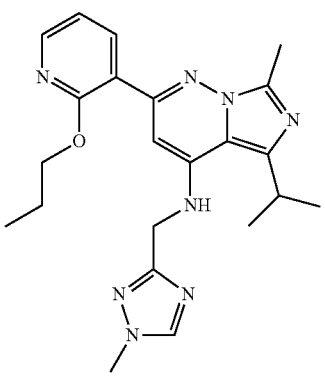 [SMILES: CCCOc1ncccc1-c1cc(NCc2ncn(C)n2)c2c(C(C)C)nc(C)n2n1]

Prepared in a way similar to example 19 from 2,4-dichloro-5-isopropyl-7-methylimidazo[1,5-b]pyridazine, (1-methyl-1H-1,2,4-triazol-3-yl)methanamine and 2-propoxy-3-(4,4,5,5-tetramethyl-1,3,2-dioxaborolan-2-yl)pyridine.

$^1$H NMR (CDCl$_3$ 400 MHz): δ 8.24 (dd, J=2.0, 4.8 Hz, 1H), 8.06-8.03 (m, 2H), 7.02 (dd, J=4.8, 8.0 Hz, 1H), 6.11 (s, 1H), 5.94 (brs, 1H), 4.56 (d, J=4.8 Hz, 2H), 4.39 (q, J=6.8 Hz, 2H), 3.95 (s, 3H), 3.45-3.38 (m, 1H), 2.72 (s, 3H), 1.88-1.79 (m, 2H), 1.50 (d, J=6.8 Hz, 6H), 1.07 (t, J=7.2 Hz, 3H) LC-MS: t$_R$=1.71 minutes (Method E), m/z=421.2 [M+H]$^+$.

Example 73: 2-(2-ethoxy-3-pyridyl)-N-[(2-fluoro-3-pyridyl)methyl]-5-isopropyl-7-methyl-imidazo[1,5-b]pyridazin-4-amine

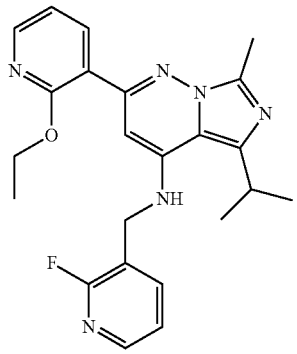 [SMILES: CCOc1ncccc1-c1cc(NCc2cccnc2F)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and 2-fluoronicotinaldehyde.

$^1$H NMR (CDCl$_3$ 400 MHz): δ 8.21-8.17 (m, 2H), 8.01-7.99 (m, 1H), 7.99-7.78 (m, 1H), 7.21-7.19 (m, 1H), 6.99-6.95 (m, 1H), 6.10 (s, 1H), 5.46 (br.s, 1H), 4.63 (d, J=6.0 Hz, 2H), 4.34 (q, J=6.8 Hz, 2H), 3.36-3.30 (m, 1H), 2.74 (s, 3H), 1.48 (d, J=6.8 Hz, 6H), 1.21 (t, J=6.8 Hz, 3H). LC-MS: t$_R$=1.88 minutes (Method F), m/z=421 [M+H]$^+$.

Example 74: 2-(2-ethoxy-3-pyridyl)-5-isopropyl-7-methyl-N-(2-pyridylmethyl)imidazo[1,5-b]pyridazin-4-amine

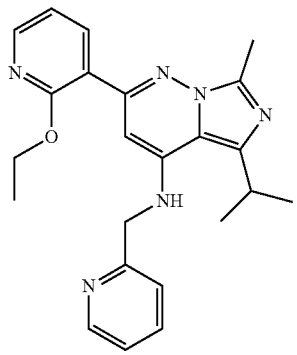 [SMILES: CCOc1ncccc1-c1cc(NCc2ccccn2)c2c(C(C)C)nc(C)n2n1]

Prepared in a way similar to example 1 from 2-(2-ethoxypyridin-3-yl)-5-isopropyl-7-methylimidazo[1,5-b]pyridazin-4-amine and nicotinaldehyde.

$^1$H NMR (CDCl$_3$ 400 MHz): δ 8.65 (d, J=4.8 Hz, 1H), 8.27-8.25 (m, 1H), 8.06-8.04 (m, 1H), 7.77-7.76 (m, 1H), 7.36-7.34 (m, 2H), 7.17 (br.s, 1H), 7.04-7.01 (m, 1H), 6.23 (s, 1H), 4.61 (d, J=4.0 Hz, 2H), 4.48 (q, J=7.2 Hz, 2H), 3.68-361 (m, 1H), 2.84 (s, 3H), 1.58 (d, J=6.8 Hz, 6H), 1.41 (t, J=7.2 Hz, 3H). LC-MS: t$_R$=2.29 minutes (Method D), m/z=403 [M+H]$^+$.

Example 75: 2-(2-ethoxy-3-pyridyl)-5-isopropyl-7-methyl-N-(pyrimidin-2-ylmethyl)imidazo[1,5-b]pyridazin-4-amine

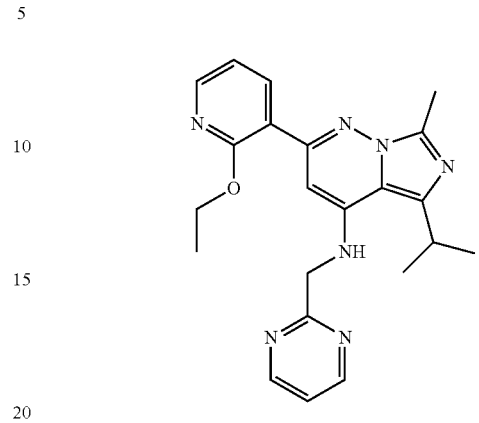

Prepared in a way similar to example 19 from 2,4-dichloro-5-isopropyl-7-methylimidazo[1,5-b]pyridazine, pyrimidin-5-ylmethanamine hydrochloride and (2-ethoxy-pyridin-3-yl)boronic acid.

$^1$H NMR (CDCl$_3$ 400 MHz): δ 8.83 (d, J=5.2 Hz, 2H), 8.24 (dd, J=2.0, 5.2 Hz, 1H), 8.07 (dd, J=2.0, 7.2 Hz, 1H), 7.34 (t, J=5.2 Hz, 1H), 7.03 (dd, J=5.2, 7.2 Hz, 1H), 6.84 (brs, 1H), 6.12 (s, 1H), 4.73 (d, J=4.0 Hz, 2H), 4.52 (q, J=7.2 Hz, 2H), 3.62-3.55 (m, 1H), 2.72 (s, 3H), 1.54 (d, J=6.8 Hz, 6H), 1.46 (t, J=7.2 Hz, 3H). LC-MS: t$_R$=1.98 minutes (Method E), m/z=404.1 [M+H]$^+$.

Example 76: 2-(2-ethoxy-3-pyridyl)-N-[(5-fluoropyrimidin-2-yl)methyl]-5-isopropyl-7-methyl-imidazo[1,5-b]pyridazin-4-amine

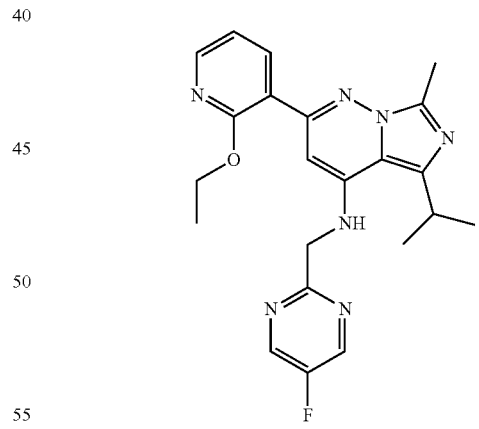

Prepared in a way similar to example 19 from 2,4-dichloro-5-isopropyl-7-methylimidazo[1,5-b]pyridazine, (2-fluoropyrimidin-5-yl)methanamine hydrochloride and (2-ethoxypyridin-3-yl)boronic acid.

$^1$H NMR (CDCl$_3$ 400 MHz): δ 8.70 (s, 2H), 8.24 (dd, J=2.0, 5.2 Hz, 1H), 8.07 (dd, J=2.0, 7.6 Hz, 1H), 7.03 (dd, J=5.2, 7.6 Hz, 1H), 6.62 (brs, 1H), 6.11 (s, 1H), 4.73 (d, J=3.2 Hz, 2H), 4.51 (q, J=7.2 Hz, 2H), 3.57-3.50 (m, 1H), 2.72 (s, 3H), 1.53 (d, J=7.2 Hz, 6H), 1.45 (t, J=7.2 Hz, 3H). LC-MS: t$_R$=2.12 minutes (Method E), m/z=422 [M+H]$^+$.

Example 77: 2-(2-ethoxy-3-pyridyl)-5-isopropyl-N-[(2-methoxy-3-pyridyl)methyl]-7-methyl-imidazo[1,5-b]pyridazin-4-amine

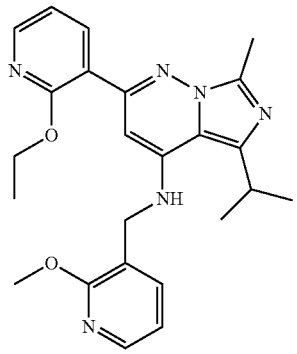 [SMILES: CCOc1ncccc1-c1cc(NCc2cccnc2OC)c2c(C(C)C)nc(C)n2n1]

Prepared in a way similar to example 19 from 2,4-dichloro-5-isopropyl-7-methylimidazo[1,5-b]pyridazine, (2-methoxypyridin-3-yl)methanamine and (2-ethoxypyridin-3-yl)boronic acid.

$^1$H NMR (CDCl$_3$ 400 MHz): δ 8.21 (dd, J=2.0, 2.0 Hz, 1H), 8.13 (dd, J=1.6, 1.6 Hz, 1H), 8.02 (dd, J=2.0, 2.0 Hz, 1H), 7.56 (dd, J=1.6, 1.6 Hz, 1H), 7.00-6.97 (m, 1H), 6.91-6.89 (m, 1H), 6.04 (s, 1H), 5.55 (br.s, 1H), 4.50 (d, J=5.6 Hz, 2H), 4.39 (q, J=7.2 Hz, 2H), 4.03 (s, 3H), 3.34-3.27 (m, 1H), 2.69 (s, 3H), 1.47 (d, J=6.8 Hz, 6H), 1.29 (t, J=7.2 Hz, 3H). LC-MS: t$_R$=1.96 minutes (Method F), m/z=433.1 [M+H]$^+$.

Example 78: 2-(2-ethoxy-3-pyridyl)-N-(imidazo[1,5-a]pyridin-5-ylmethyl)-5-isopropyl-7-methyl-imidazo[1,5-b]pyridazin-4-amine

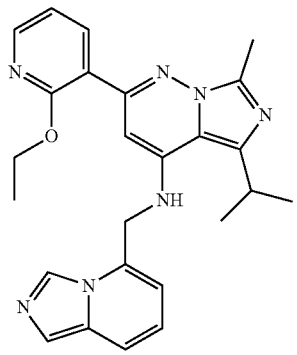 [SMILES: CCOc1ncccc1-c1cc(NCc2cccc3cncn23)c2c(C(C)C)nc(C)n2n1]

Prepared in a way similar to example 19 from 2,4-dichloro-5-isopropyl-7-methylimidazo[1,5-b]pyridazine, imidazo[1,5-a]pyridin-5-ylmethanamine and (2-ethoxypyridin-3-yl)boronic acid.

$^1$H NMR (CDCl$_3$ 400 MHz): δ 8.19 (d, J=2.0 Hz, J=2.0 Hz 1H), 8.15 (s, 1H), 8.06 (dd, J=1.6 Hz, J=2.0 Hz, 1H), 7.61 (s, 1H), 7.52 (d, J=9.2 Hz, 1H), 6.99-6.96 (m, 1H), 6.80-6.78 (m, 1H), 6.70 (d, J=6.4 Hz, 1H), 6.13 (s, 1H), 5.38 (br. s, 1H), 4.79 (d, J=5.6 Hz, 2H), 4.28 (q, J=7.2 Hz, 2H), 3.29-3.26 (m, 1H), 2.76 (s, 3H), 1.47 (d, J=6.8 Hz, 6H), 1.08 (t, J=6.8 Hz, 3H). LC-MS: t$_R$=1.35 minutes (Method F), m/z=442.1 [M+H]$^+$.

Example 79: 2-(2-ethoxy-3-pyridyl)-N-(imidazo[1,2-a]pyridin-5-ylmethyl)-5-isopropyl-7-methyl-imidazo[1,5-b]pyridazin-4-amine

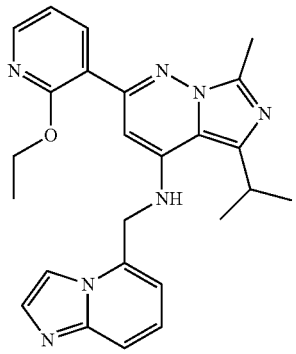 [SMILES: CCOc1ncccc1-c1cc(NCc2cccc3nccn23)c2c(C(C)C)nc(C)n2n1]

Prepared in a way similar to example 19 from 2,4-dichloro-5-isopropyl-7-methylimidazo[1,5-b]pyridazine, imidazo[1,2-a]pyridin-5-ylmethanamine and (2-ethoxypyridin-3-yl)boronic acid.

$^1$H NMR (CDCl$_3$ 400 MHz): δ 8.19 (dd, J=4.8, 1.6 Hz, 1H), 8.06 (dd, J=7.6, 2.0 Hz, 1H), 7.80 (s, 1H), 7.71 (d, J=9.2 Hz, 1H), 7.61 (s, 1H), 7.29-7.25 (m, 1H), 6.98 (dd, J=7.6, 4.8 Hz, 1H), 6.94 (d, J=6.8 Hz, 1H), 6.14 (s, 1H), 5.41 (br s, 1H), 4.80 (d, J=5.6 Hz, 2H), 4.27 (q, J=7.2 Hz, 2H), 3.31-3.24 (m, 1H), 2.75 (s, 3H), 1.47 (d, J=6.8 Hz, 6H), 1.06 (t, J=7.2 Hz, 3H). LC-MS: t$_R$=1.27 minutes (Method F), m/z=442.1 [M+H]$^+$.

Example 80: 2-(2-ethoxy-3-pyridyl)-5-isopropyl-7-methyl-N-[[2-(trifluoromethyl)-3-pyridyl]methyl]imidazo[1,5-b]pyridazin-4-amine Prepared in a way similar to example 19 from 2,4-dichloro-5-isopropyl-7-methylimidazo[1,5-b]pyridazine, (2-(trifluoromethyl)pyridin-3-yl)methanamine and (2-ethoxypyridin-3-yl)boronic acid.

$^1$H NMR (CDCl$_3$ 400 MHz): δ 8.65 (d, J=4.4 Hz, 1H), 8.19 (dd, J=1.6, 4.8 Hz, 1H), 8.02 (dd, J=1.6, 7.2 Hz, 1H), 7.95 (d, J=7.6 Hz, 1H), 7.52 (dd, J=4.4, 7.6 Hz, 1H), 6.97 (dd, J=4.8, 7.2 Hz, 1H), 5.95 (s, 1H), 5.45 (brt, J=5.6 Hz, 1H), 4.86 (d, J=5.6 Hz, 2H), 4.29 (q, J=7.2 Hz, 2H), 3.36-3.26 (m, 1H), 2.71 (s, 3H), 1.49 (d, J=6.8 Hz, 6H), 1.13 (t, J=7.2 Hz, 3H). LC-MS: t$_R$=1.8 minutes (Method F), m/z=471.1 [M+H]$^+$.

Example 81: 2-(1,3-benzoxazol-7-yl)-5-isopropyl-7-methyl-N-[(1-methyl-1,2,4-triazol-3-yl)methyl]imidazo[1,5-b]pyridazin-4-amine

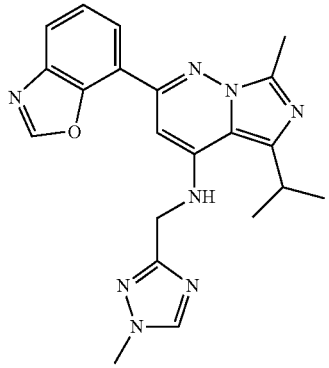 [SMILES: Cc1nc(C(C)C)c2c(NCc3ncn(C)n3)cc(-c3cccc4ncoc34)nn12]

Prepared in a way similar to example 56 from 2,4-dichloro-5-isopropyl-7-methylimidazo[1,5-b]pyridazine, (1-methyl-1H-1,2,4-triazol-3-yl)methanamine and 7-bromobenzo[d]oxazole.

$^1$H NMR (CDCl$_3$ 400 MHz) δ 8.23 (s, 1H), 8.09 (d, J=8.0 Hz, 1H), 8.07 (s, 1H), 7.88 (d, J=7.2 Hz, 1H), 7.53-7.49 (m, 1H), 6.33 (s, 1H), 6.05 (br s, 1H), 4.68 (d, J=4.8 Hz, 2H), 3.96 (s, 3H), 3.48-3.36 (m, 1H), 2.76 (s, 3H), 1.50 (d, J=6.8 Hz, 6H). LC-MS: $t_R$=1.68 minutes (Method E), m/z=403.1 [M+H]$^+$.

In Vitro Testing

PDE1 Inhibition Assay

PDE1A, PDE1B and PDE1C assays were performed as follows: the assays were performed in 60 μL samples containing a fixed amount of the PDE1 enzyme (sufficient to convert 20-25% of the cyclic nucleotide substrate), a buffer (50 mM HEPES (4-(2-hydroxyethyl)-1-piperazineethane-sulfonic acid) pH 7.6; 10 mM MgCl$_2$; 0.02% Tween20), 0.1 mg/ml BSA (bovine serum albumin), 15 nM tritium labelled cAMP and varying amounts of inhibitors. Reactions were initiated by addition of the cyclic nucleotide substrate, and reactions were allowed to proceed for 1 hr at room temperature before being terminated through mixing with 20 μL (0.2 mg) yttrium silicate SPA beads (PerkinElmer). The beads were allowed to settle for 1 hr in the dark before the plates were counted in a Wallac 1450 Microbeta counter. The measured signals were converted to activity relative to an uninhibited control (100%) and IC$_{50}$ values were calculated using XlFit (model 205, IDBS).

The invention claimed is:

1. A method for the treatment of a neurodegenerative disorder selected from the group consisting of Alzheimer's Disease, Parkinson's Disease and Huntington's Disease; or for the treatment of a psychiatric disorder selected from the group consisting of Attention Deficit Hyperactivity Disorder (ADHD), depression, anxiety, narcolepsy, cognitive impairment and cognitive impairment associated with schizophrenia (CIAS), or for the treatment of restless leg syndrome, which method comprises the administration of a therapeutically effective amount of a compound of formula (I)

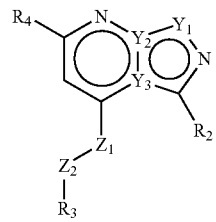

wherein
$Y_1$=N—$R_1$, $Y_2$=C and $Y_3$=C, or
$Y_1$=C—$R_1$, $Y_2$=N and $Y_3$=C;
$Z_1$ is selected from NH, CH$_2$, O and S;
$Z_2$ is selected from NH, CH$_2$, O and S;
with the proviso that at least one of $Z_1$ and $Z_2$ is CH$_2$;
$R_1$ is selected from the group consisting of hydrogen, linear or branched C$_{1-4}$ alkyl and saturated monocyclic C$_{3-4}$ cycloalkyl, wherein said linear or branched C$_{1-4}$ alkyl and saturated monocyclic C$_{3-4}$ cycloalkyl can be optionally substituted with one or more halogen;
$R_2$ is selected from the group consisting of linear or branched C$_{1-6}$ alkyl, saturated monocyclic C$_{3-6}$ cycloalkyl, oxetanyl, tetrahydrofuranyl and tetrahydropyranyl, all of which can optionally be substituted with one or more halogen;
$R_3$ is a 5- or 6-membered heteroaryl, which can optionally be substituted with one or more substituents selected from linear or branched C$_{1-4}$ alkyl, linear or branched C$_{1-4}$alkoxy and halogen, wherein said linear or branched C$_{1-4}$ alkyl and linear or branched C$_{1-4}$ alkoxy can be optionally substituted with one or more halogen, or
$R_3$ is a 9-membered bicyclic heteroaryl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$alkoxy can be optionally substituted with one or more halogen;
$R_4$ is a 5- or 6-membered heteroaryl, which can optionally be substituted with one or more substituents selected from linear or branched C$_{1-4}$ alkyl, linear or branched C$_{1-4}$alkoxy and halogen, wherein said linear or branched C$_{1-4}$ alkyl and linear or branched C$_{1-4}$alkoxy can be optionally substituted with one or more halogen, or
$R_4$ is a phenyl, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$alkoxy can be optionally substituted with one or more halogen, or
$R_4$ is a pyridinone, which can optionally be substituted with one or more substituents selected from linear or branched C$_{1-4}$ alkyl, linear or branched C$_{1-4}$ alkoxy and halogen, wherein said linear or branched C$_{1-4}$ alkyl and linear or branched C$_{1-4}$alkoxy can be optionally substituted with one or more halogen; or
$R_4$ is a 9-membered bicyclic heteroaryl, which can optionally be substituted with one or more substituents selected from linear or branched C$_{1-4}$ alkyl, linear or branched C$_{1-4}$ alkoxy and halogen, wherein said linear or branched $C_{1-4}$ alkyl and linear or branched $C_{1-4}$ alkoxy can be optionally substituted with one or more halogen;

or a pharmaceutically acceptable salt thereof, to a patient in need thereof.

2. The method of claim 1, wherein the compound of formula (I) is of formula (Ia)

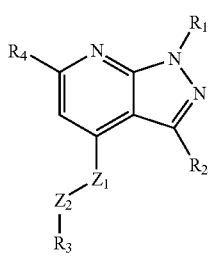

(Ia)

wherein $Z_1$, $Z_2$, $R_1$, $R_2$, $R_3$ and $R_4$ are as defined in claim 1.

3. The method of claim 1, wherein the compound of formula (I) is of formula (Ib)

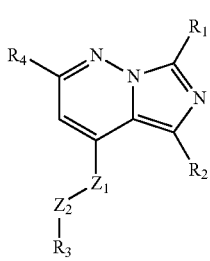

(Ib)

wherein $Z_1$, $Z_2$, $R_1$, $R_2$, $R_3$ and $R_4$ are as defined in claim 1.

4. The method of claim 1, wherein $Z_1$ is NH.
5. The method of claim 1, wherein $Z_2$ is $CH_2$.
6. The method of claim 1, wherein $Z_1$ is NH and $Z_2$ is $CH_2$.
7. The method of claim 1, wherein $R_1$ is a linear or branched $C_{1-4}$ alkyl.
8. The method of claim 1, wherein $R_2$ is linear or branched $C_{1-6}$ alkyl.
9. The method of claim 1, wherein:
$R_3$ is a 5-membered heteroaryl selected from pyrazolyl, imidazolyl, oxazolyl, oxadiazolyl, triazolyl, tetrazolyl, thiazolyl and thiophenyl, all of which can optionally be substituted with a methyl; or
$R_3$ is a 6-membered heteroaryl, which can optionally be substituted with a substituent selected from methyl, trifluoromethyl or a linear or branched $C_{1-4}$alkoxy; wherein said 6-membered heteroaryl is selected from pyridyl, pyrimidinyl, pyrazinyl and pyridazinyl; or
$R_3$ is a 9-membered bicyclic heteroaryl, which is optionally substituted with one or more methyl.

10. The method of claim 1, wherein:
$R_4$ is a 5-membered heteroaryl selected from pyrazolyl, imidazolyl, oxazolyl, oxadiazolyl, triazolyl, tetrazolyl, thiazolyl and thiophenyl wherein said 5-membered heteroaryl can be optionally substituted with a methyl; or
$R_4$ is a 6-membered heteroaryl, which can optionally be substituted with a linear or branched $C_{1-4}$alkoxy; wherein said 6-membered heteroaryl is selected from pyridyl, pyrimidinyl, pyrazinyl and pyridazinyl; or
$R_4$ is a phenyl, which can optionally be substituted with one or more methyl; or
$R_4$ is a pyridinone, which can optionally be substituted with one or more methyl; or
$R_4$ is a 9-membered bicyclic heteroaryl, which can optionally be substituted with one or more methyl.

11. The method of claim 1, wherein the compound, or pharmaceutically acceptable salt thereof, is selected from the group consisting of:
6-(2-ethoxy-3-pyridyl)-3-isopropyl-1-methyl-N-[(1-methylimidazol-4-yl)methyl]pyrazolo[3,4-b]pyridin-4-amine;
6-(2-ethoxy-3-pyridyl)-3-isopropyl-1-methyl-N-[(2-methyloxazol-4-yl)methyl]pyrazolo[3,4-b]pyridin-4-amine;
6-(2-ethoxy-3-pyridyl)-3-isopropyl-1-methyl-N-(1H-pyrazol-3-ylmethyl)pyrazolo[3,4-b]pyridin-4-amine;
6-(2-ethoxy-3-pyridyl)-3-isopropyl-1-methyl-N-[(1-methyl-1,2,4-triazol-3-yl)methyl]pyrazolo[3,4-b]pyridin-4-amine;
6-(2-ethoxy-3-pyridyl)-3-isopropyl-1-methyl-N-[(5-methyl-1,2,4-oxadiazol-3-yl)methyl]pyrazolo[3,4-b]pyridin-4-amine;
6-(2-ethoxy-3-pyridyl)-3-isopropyl-1-methyl-N-[(5-methyl-1H-pyrazol-3-yl)methyl]pyrazolo[3,4-b]pyridin-4-amine;
6-(2-ethoxy-3-pyridyl)-3-isopropyl-N-[(2-methoxy-4-pyridyl)methyl]-1-methyl-pyrazolo[3,4-b]pyridin-4-amine;
2-(2-ethoxy-3-pyridyl)-5-isopropyl-7-methyl-N-[(1-methylimidazol-4-yl)methyl]imidazo[1,5-b]pyridazin-4-amine;
2-(2-ethoxy-3-pyridyl)-5-isopropyl-7-methyl-N-[(2-methyloxazol-4-yl)methyl]imidazo[1,5-b]pyridazin-4-amine;
2-(2-ethoxy-3-pyridyl)-5-isopropyl-7-methyl-N-(1H-pyrazol-3-ylmethyl)imidazo[1,5-b]pyridazin-4-amine;
2-(2-ethoxy-3-pyridyl)-5-isopropyl-7-methyl-N-[(1-methyl-1,2,4-triazol-3-yl)methyl]imidazo[1,5-b]pyridazin-4-amine;
2-(2-ethoxy-3-pyridyl)-5-isopropyl-7-methyl-N-[(5-methyl-1,2,4-oxadiazol-3-yl)methyl]imidazo[1,5-b]pyridazin-4-amine;
2-(2-ethoxy-3-pyridyl)-5-isopropyl-7-methyl-N-[(5-methyl-1H-pyrazol-3-yl)methyl]imidazo[1,5-b]pyridazin-4-amine;
2-(2-ethoxy-3-pyridyl)-5-isopropyl-N-[(5-methoxy-3-pyridyl)methyl]-7-methyl-imidazo[1,5-b]pyridazin-4-amine;
2-(2-ethoxy-3-pyridyl)-5-isopropyl-N-[(2-methoxy-4-pyridyl)methyl]-7-methyl-imidazo[1,5-b]pyridazin-4-amine;
2-(2-ethoxy-3-pyridyl)-5-isopropyl-7-methyl-N-[(2-methyloxazol-5-yl)methyl]imidazo[1,5-b]pyridazin-4-amine;
2-(2-ethoxy-3-pyridyl)-5-isopropyl-7-methyl-N-[(2-methylthiazol-5-yl)methyl]imidazo[1,5-b]pyridazin-4-amine;
2-(2-ethoxy-3-pyridyl)-5-isopropyl-7-methyl-N-(1H-pyrazol-4-ylmethyl)imidazo[1,5-b]pyridazin-4-amine;
6-(2-ethoxy-3-pyridyl)-3-isopropyl-1-methyl-N-[(1-methylpyrazol-4-yl)methyl]pyrazolo[3,4-b]pyridin-4-amine;

6-(2-ethoxy-3-pyridyl)-3-isopropyl-1-methyl-N-[(2-methyltetrazol-5-yl)methyl]pyrazolo[3,4-b]pyridin-4-amine;

6-(2-ethoxy-3-pyridyl)-3-isopropyl-1-methyl-N-[(1-methylpyrazol-3-yl)methyl]pyrazolo[3,4-b]pyridin-4-amine;

2-(2-ethoxy-3-pyridyl)-5-isopropyl-7-methyl-N-[(1-methylpyrazol-4-yl)methyl]imidazo[1,5-b]pyridazin-4-amine;

2-(2-ethoxy-3-pyridyl)-5-isopropyl-7-methyl-N-[(2-methyltetrazol-5-yl)methyl]imidazo[1,5-b]pyridazin-4-amine;

2-(2-ethoxy-3-pyridyl)-5-isopropyl-7-methyl-N-[(1-methylpyrazol-3-yl)methyl]imidazo[1,5-b]pyridazin-4-amine;

6-(2-ethoxy-3-pyridyl)-3-isopropyl-N-[(5-methoxy-3-pyridyl)methyl]-1-methyl-pyrazolo[3,4-b]pyridin-4-amine;

6-(2-ethoxypyridin-3-yl)-3-isopropyl-1-methyl-N-((2-methyl-2H-1,2,3-triazol-4-yl)methyl)-1H-pyrazolo[3,4-b]pyridin-4-amine;

6-(2-ethoxy-3-pyridyl)-3-isopropyl-1-methyl-N-[(2-methyloxazol-5-yl)methyl]pyrazolo[3,4-b]pyridin-4-amine;

6-(2-ethoxy-3-pyridyl)-3-isopropyl-1-methyl-N-[(2-methylthiazol-5-yl)methyl]pyrazolo[3,4-b]pyridin-4-amine;

6-(2-ethoxy-3-pyridyl)-3-isopropyl-1-methyl-N-[(1-methyltriazol-4-yl)methyl]pyrazolo[3,4-b]pyridin-4-amine;

6-(2-ethoxy-3-pyridyl)-3-isopropyl-1-methyl-N-(1H-pyrazol-4-ylmethyl)pyrazolo[3,4-b]pyridin-4-amine;

6-(2-ethoxy-3-pyridyl)-3-isopropyl-1-methyl-N-[(5-methyl-1,3,4-oxadiazol-2-yl)methyl]pyrazolo[3,4-b]pyridin-4-amine;

6-(2-ethoxy-3-pyridyl)-3-isopropyl-1-methyl-N-[(3-methyl-1,2,4-oxadiazol-5-yl)methyl]pyrazolo[3,4-b]pyridin-4-amine;

3-isopropyl-1-methyl-N-[(1-methyl-1,2,4-triazol-3-yl)methyl]-6-(2-propoxy-3-pyridyl)pyrazolo[3,4-b]pyridin-4-amine;

3-isopropyl-1-methyl-N-[(1-methylimidazol-4-yl)methyl]-6-(2-propoxy-3-pyridyl)pyrazolo[3,4-b]pyridin-4-amine;

6-(2-ethoxy-3-pyridyl)-3-isopropyl-1-methyl-N-[(4-methylpyrimidin-2-yl)methyl]pyrazolo[3,4-b]pyridin-4-amine;

6-(2-ethoxy-3-pyridyl)-3-isopropyl-1-methyl-N-(pyrimidin-2-ylmethyl)pyrazolo[3,4-b]pyridin-4-amine;

6-(2-ethoxy-3-pyridyl)-3-isopropyl-N-[(6-methoxy-3-pyridyl)methyl]-1-methyl-pyrazolo[3,4-b]pyridin-4-amine;

6-(2-ethoxy-3-pyridyl)-3-isopropyl-1-methyl-N-[[2-(trifluoromethyl)-3-pyridyl]methyl]pyrazolo[3,4-b]pyridin-4-amine;

6-(2-ethoxy-3-pyridyl)-3-isopropyl-N-[(4-methoxy-2-pyridyl)methyl]-1-methyl-pyrazolo[3,4-b]pyridin-4-amine;

6-(2-ethoxy-3-pyridyl)-3-isopropyl-1-methyl-N-(2-pyridylmethyl)pyrazolo[3,4-b]pyridin-4-amine;

6-(2-ethoxy-3-pyridyl)-3-isopropyl-N-[(6-methoxy-2-pyridyl)methyl]-1-methyl-pyrazolo[3,4-b]pyridin-4-amine;

6-(2-ethoxy-3-pyridyl)-3-isopropyl-1-methyl-N-[(6-methyl-2-pyridyl)methyl]pyrazolo[3,4-b]pyridin-4-amine;

2-(2-ethoxy-3-pyridyl)-5-isopropyl-7-methyl-N-(1,2,4-oxadiazol-3-ylmethyl)imidazo[1,5-b]pyridazin-4-amine;

2-(2-ethoxy-3-pyridyl)-5-isopropyl-7-methyl-N-[(2-methyltriazol-4-yl)methyl]imidazo[1,5-b]pyridazin-4-amine;

2-(2-ethoxy-3-pyridyl)-5-isopropyl-7-methyl-N-[(5-methyl-1,3,4-oxadiazol-2-yl)methyl]imidazo[1,5-b]pyridazin-4-amine;

2-(2-ethoxy-3-pyridyl)-5-isopropyl-7-methyl-N-[(3-methyl-1,2,4-oxadiazol-5-yl)methyl]imidazo[1,5-b]pyridazin-4-amine;

(−)-2-(2-ethoxy-3-pyridyl)-7-methyl-N-[(1-methylpyrazol-4-yl)methyl]-5-[1-methylpropyl]imidazo[1,5-b]pyridazin-4-amine;

(+)-2-(2-ethoxy-3-pyridyl)-7-methyl-N-[(1-methylpyrazol-4-yl)methyl]-5-[1-methylpropyl]imidazo[1,5-b]pyridazin-4-amine;

(−)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine;

(+)-2-(2-ethoxy-3-pyridyl)-7-methyl-N-[(1-methyl-1,2,4-triazol-3-yl)methyl]-5-[1-methylpropyl]imidazo[1,5-b]pyridazin-4-amine;

(+)-2-(2-ethoxy-3-pyridyl)-7-methyl-N-(1H-pyrazol-3-ylmethyl)-5-[1-methylpropyl]imidazo[1,5-b]pyridazin-4-amine;

(−)-2-(2-ethoxy-3-pyridyl)-7-methyl-N-(1H-pyrazol-3-ylmethyl)-5-[1-methylpropyl]imidazo[1,5-b]pyridazin-4-amine;

(+)-2-(2-ethoxy-3-pyridyl)-N-[(2-methoxy-4-pyridyl)methyl]-7-methyl-5-[1-methylpropyl]imidazo[1,5-b]pyridazin-4-amine;

(−)-2-(2-ethoxy-3-pyridyl)-N-[(2-methoxy-4-pyridyl)methyl]-7-methyl-5-[1-methylpropyl]imidazo[1,5-b]pyridazin-4-amine;

3-isopropyl-6-(2-methoxy-3-pyridyl)-1-methyl-N-[(1-methyl-1,2,4-triazol-3-yl)methyl]pyrazolo[3,4-b]pyridin-4-amine;

3-(3-isopropyl-1-methyl-4-(((1-methyl-1H-1,2,4-triazol-3-yl)methyl)amino)-1H-pyrazolo[3,4-b]pyridin-6-yl)-1-methylpyridin-2(1H)-one;

3-isopropyl-6-(3-methoxypyrazin-2-yl)-1-methyl-N-((1-methyl-1H-1,2,4-triazol-3-yl)methyl)-1H-pyrazolo[3,4-b]pyridin-4-amine;

3-isopropyl-1-methyl-6-(2-methyl-3-thienyl)-N-[(1-methyl-1,2,4-triazol-3-yl)methyl]pyrazolo[3,4-b]pyridin-4-amine;

3-isopropyl-1-methyl-N-((1-methyl-1H-1,2,4-triazol-3-yl)methyl)-6-(4-methyloxazol-2-yl)-1H-pyrazolo[3,4-b]pyridin-4-amine;

3-isopropyl-1-methyl-6-(4-methylthiazol-2-yl)-N-[(1-methyl-1,2,4-triazol-3-yl)methyl]pyrazolo[3,4-b]pyridin-4-amine;

3-isopropyl-1-methyl-N-((1-methyl-1H-1,2,4-triazol-3-yl)methyl)-6-(4-methylthiazol-5-yl)-1H-pyrazolo[3,4-b]pyridin-4-amine;

3-isopropyl-1-methyl-6-(5-methylthiazol-2-yl)-N-[(1-methyl-1,2,4-triazol-3-yl)methyl]pyrazolo[3,4-b]pyridin-4-amine;

3-isopropyl-1-methyl-N-[(1-methyl-1,2,4-triazol-3-yl)methyl]-6-phenyl-pyrazolo[3,4-b]pyridin-4-amine;

3-isopropyl-6-(4-methoxypyrimidin-5-yl)-1-methyl-N-[(1-methyl-1,2,4-triazol-3-yl)methyl]pyrazolo[3,4-b]pyridin-4-amine;

3-isopropyl-1-methyl-N-[(1-methyl-1,2,4-triazol-3-yl)methyl]-6-(2-thienyl)pyrazlo[3,4-b]pyridin-4-amine;

6-(3-ethoxypyridazin-4-yl)-3-isopropyl-1-methyl-N-[(1-methyl-1,2,4-triazol-3-yl)methyl]pyrazolo[3,4-b]pyridin-4-amine;

3-isopropyl-1-methyl-N-[(1-methyl-1,2,4-triazol-3-yl)methyl]-6-(3-propoxypyridazin-4-yl)pyrazolo[3,4-b]pyridin-4-amine;

6-(3-ethoxy-4-pyridyl)-3-isopropyl-1-methyl-N-[(1-methyl-1,2,4-triazol-3-yl)methyl]pyrazolo[3,4-b]pyridin-4-amine;

2-(3-ethoxypyridazin-4-yl)-5-isopropyl-7-methyl-N-[(1-methylpyrazol-4-yl)methyl]imidazo[1,5-b]pyridazin-4-amine;

2-(3-ethoxy-4-pyridyl)-5-isopropyl-7-methyl-N-[(1-methylpyrazol-4-yl)methyl]imidazo[1,5-b]pyridazin-4-amine;

5-isopropyl-7-methyl-N-[(1-methylpyrazol-4-yl)methyl]-2-(2-propoxy-3-pyridyl)imidazo[1,5-b]pyridazin-4-amine;

5-isopropyl-7-methyl-N-[(1-methyl-1,2,4-triazol-3-yl)methyl]-2-(2-propoxy-3-pyridyl)imidazo[1,5-b]pyridazin-4-amine;

2-(2-ethoxy-3-pyridyl)-N-[(2-fluoro-3-pyridyl)methyl]-5-isopropyl-7-methyl-imidazo[1,5-b]pyridazin-4-amine;

2-(2-ethoxy-3-pyridyl)-5-isopropyl-7-methyl-N-(2-pyridylmethyl)imidazo[1,5-b]pyridazin-4-amine;

2-(2-ethoxy-3-pyridyl)-5-isopropyl-7-methyl-N-(pyrimidin-2-ylmethyl)imidazo[1,5-b]pyridazin-4-amine;

2-(2-ethoxy-3-pyridyl)-N-[(5-fluoropyrimidin-2-yl)methyl]-5-isopropyl-7-methyl-imidazo[1,5-b]pyridazin-4-amine;

2-(2-ethoxy-3-pyridyl)-5-isopropyl-N-[(2-methoxy-3-pyridyl)methyl]-7-methyl-imidazo[1,5-b]pyridazin-4-amine;

2-(2-ethoxy-3-pyridyl)-N-(imidazo[1,5-a]pyridin-5-ylmethyl)-5-isopropyl-7-methyl-imidazo[1,5-b]pyridazin-4-amine;

2-(2-ethoxy-3-pyridyl)-N-(imidazo[1,2-a]pyridin-5-ylmethyl)-5-isopropyl-7-methyl-imidazo[1,5-b]pyridazin-4-amine;

2-(2-ethoxy-3-pyridyl)-5-isopropyl-7-methyl-N-[[2-(trifluoromethyl)-3-pyridyl]methyl]imidazo[1,5-b]pyridazin-4-amine;

2-(1,3-benzoxazol-7-yl)-5-isopropyl-7-methyl-N-[(1-methyl-1,2,4-triazol-3-yl)methyl]imidazo[1,5-b]pyridazin-4-amine;

and pharmaceutically acceptable salts of any of these compounds.

12. The method of claim 1, wherein the method is for the treatment of a neurodegenerative disorder selected from the group consisting of Alzheimer's Disease, Parkinson's Disease and Huntington's Disease.

13. The method of claim 1, wherein the method is for the treatment of a psychiatric disorder selected from the group consisting of Attention Deficit Hyperactivity Disorder (ADHD), depression, anxiety, narcolepsy, cognitive impairment and cognitive impairment associated with schizophrenia (CIAS).

14. The method of claim 1, wherein the method is a method for the treatment of restless leg syndrome.

* * * * *